(12) United States Patent
Carlyon

(10) Patent No.: US 11,458,197 B2
(45) Date of Patent: *Oct. 4, 2022

(54) **AIPA, OMPA, AND ASP14 IN VACCINE COMPOSITIONS AND DIAGNOSTIC TARGETS FOR *ANAPLASMA PHAGOCYTOPHILUM* INFECTION**

(71) Applicant: VIRGINIA COMMONWEALTH UNIVERSITY, Richmond, VA (US)

(72) Inventor: Jason Carlyon, Richmond, VA (US)

(73) Assignee: Virginia Commonwealth University, Richmond, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/071,385

(22) Filed: Oct. 15, 2020

(65) Prior Publication Data

US 2021/0038707 A1    Feb. 11, 2021

Related U.S. Application Data

(62) Division of application No. 16/105,048, filed on Aug. 20, 2018, now Pat. No. 10,842,860, which is a division of application No. 15/115,954, filed as application No. PCT/US2015/013715 on Jan. 30, 2015, now Pat. No. 10,086,058.

(60) Provisional application No. 61/935,012, filed on Feb. 3, 2014.

(51) Int. Cl.
| | |
|---|---|
| *A61K 39/02* | (2006.01) |
| *A61K 31/7088* | (2006.01) |
| *G01N 33/569* | (2006.01) |
| *C07K 14/29* | (2006.01) |
| *A61K 39/00* | (2006.01) |

(52) U.S. Cl.
CPC ...... *A61K 39/0233* (2013.01); *A61K 31/7088* (2013.01); *C07K 14/29* (2013.01); *G01N 33/56911* (2013.01); *A61K 2039/70* (2013.01); *C07K 2319/00* (2013.01); *C07K 2319/03* (2013.01); *C07K 2319/21* (2013.01); *C07K 2319/23* (2013.01); *C07K 2319/40* (2013.01); *C07K 2319/70* (2013.01); *G01N 2333/195* (2013.01); *Y02A 50/30* (2018.01)

(58) Field of Classification Search
None
See application file for complete search history.

(56) References Cited

U.S. PATENT DOCUMENTS

| | | | | |
|---|---|---|---|---|
| 9,248,174 B2* | 2/2016 | Carlyon | ............. | A61K 39/0233 |
| 9,945,851 B2* | 4/2018 | Carlyon | ............. | C07K 16/1203 |
| 10,039,815 B2* | 8/2018 | Carlyon | ................. | A61K 39/40 |
| 10,086,058 B2* | 10/2018 | Carlyon | ........... | G01N 33/56911 |
| 10,364,435 B1* | 7/2019 | Bermudes | ............... | A61K 39/07 |
| 10,376,570 B2* | 8/2019 | Carlyon | ............. | A61K 39/0233 |
| 10,495,639 B2* | 12/2019 | Carlyon | ............. | C07K 16/1246 |
| 10,736,951 B2* | 8/2020 | Carlyon | ............. | C07K 16/1246 |
| 10,842,860 B2* | 11/2020 | Carlyon | ............. | G01N 33/56911 |
| 11,273,213 B2* | 3/2022 | Marconi | ............ | A61K 39/0233 |
| 2003/0138866 A1* | 7/2003 | Mathiesen | ............. | C07K 14/20 |
| | | | | 435/7.32 |
| 2011/0008380 A1* | 1/2011 | Liu | .................. | G01N 33/56911 |
| | | | | 536/23.7 |
| 2012/0207779 A1* | 8/2012 | Liu | ........................ | A61P 37/04 |
| | | | | 424/278.1 |
| 2015/0174226 A1* | 6/2015 | Carlyon | ............. | C07K 16/1246 |
| | | | | 435/7.1 |
| 2016/0146811 A1* | 5/2016 | Carlyon | ............. | C07K 16/1246 |
| | | | | 435/7.32 |
| 2017/0165342 A1* | 6/2017 | Carlyon | ........... | G01N 33/56911 |
| 2017/0202941 A1* | 7/2017 | Carlyon | ................. | A61P 33/02 |
| 2017/0252422 A1* | 9/2017 | Marconi | .......... | G01N 33/56911 |
| 2017/0269080 A1* | 9/2017 | Carlyon | ............. | C07K 16/1246 |
| 2018/0264097 A1* | 9/2018 | Carlyon | ........... | G01N 33/56911 |
| 2018/0369354 A1* | 12/2018 | Carlyon | ............. | A61K 39/0233 |
| 2019/0117753 A1* | 4/2019 | Carlyon | ........... | G01N 33/56911 |
| 2019/0234946 A1* | 8/2019 | Carlyon | ................. | A61K 39/40 |
| 2019/0336592 A1* | 11/2019 | Carlyon | ............. | A61K 39/0233 |
| 2021/0038707 A1* | 2/2021 | Carlyon | ................. | C07K 14/29 |
| 2021/0170006 A1* | 6/2021 | Marconi | ............ | C07K 16/1246 |

FOREIGN PATENT DOCUMENTS

| | | | | |
|---|---|---|---|---|
| EP | 3102234 A1 * | 12/2016 | ......... | A61K 31/7088 |
| EP | 3781195 A1 * | 2/2021 | ......... | A61K 39/0233 |
| WO | WO-2009070507 A2 * | 6/2009 | ............. | C07K 14/29 |
| WO | WO-2014004378 A1 * | 1/2014 | ......... | A61K 39/0233 |
| WO | WO-2015116907 A1 * | 8/2015 | ......... | A61K 31/7088 |
| WO | WO-2016182847 A1 * | 11/2016 | ........... | C07K 14/195 |
| WO | WO-2019204460 A1 * | 10/2019 | ......... | A61K 39/0233 |

OTHER PUBLICATIONS

De la Fuente et al, Trends in Microbiology, Mar. 2016, 24/3:173-180 (Year: 2016).*
Woldehiwet, Veterinary Parasitology, 2010, 167:108-122 (Year: 2010).*
Seidman et al, Cell Microbiology, Aug. 2014, 16/8:1133-1145 (Year: 2014).*
Hotopp et al, PLoS Genetics, Feb. 2006, 2/2:e21, 16 pages. published Feb. 17, 2006 (Year: 2006).*

(Continued)

*Primary Examiner* — Nita M. Minnifield
(74) *Attorney, Agent, or Firm* — WCF IP

(57) ABSTRACT

*Anaplasma phagocytophilum* surface protein AipA and/or fragments thereof which comprise an invasin domain are used in compositions suitable to elicit an immune response to treat or prevent infections caused by tick-born bacteria of the Anaplasmatacaea family. AipA proteins and protein fragments or antibodies directed to AipA proteins and protein fragments are also used in diagnostic assays to detect exposure to and/or infection with Anaplasmatacaea. AipA and/or fragments thereof are also used for these purposes in combination with one or both of Asp14 and OmpA proteins and/or fragments thereof which comprise an invasin domain. Homologs of these proteins are also used in the compositions and assays.

3 Claims, 18 Drawing Sheets

Specification includes a Sequence Listing.

(56) References Cited

OTHER PUBLICATIONS

Barbet et al, Pathogens, 2013, 2:544-555 (Year: 2013).*
Futse et al, bioRxiv, 2019. pp. 1-19. Abstract only (Year: 2019).*
Green et al, mBio. Jan./Feb. 2020, 11/1, e03141-19, 16 pages. published Jan. 28, 2020 (Year: 2020).*
Kahlon et al, Infection and Immunity, Jan. 2013, 81/1:65-79. published ahead of print: Oct. 15, 2012 (Year: 2013).*
Naimi et al, Infection and Immunity, Oct. 2020. 88/10:e00106-20. published: Sep. 18, 2020 (Year: 2020).*
Ojogun et al, Infection and immunity, Nov. 2012, 80/11:3748-3760. published online: Aug. 20, 2012 (Year: 2012).*

\* cited by examiner

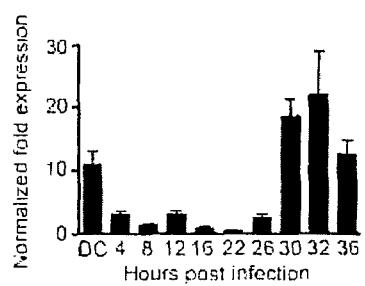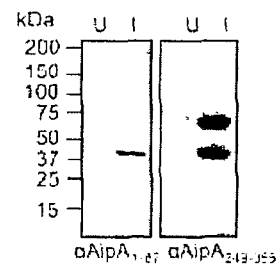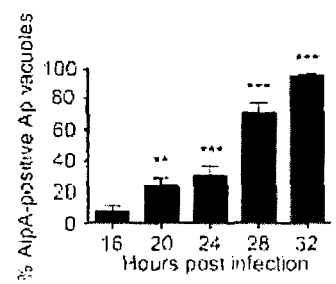
Figure 2A　　　　　　　Figure 2B　　　　　　　Figure 2C
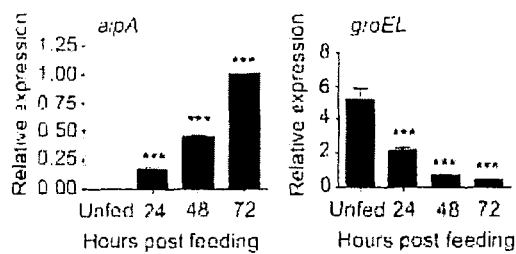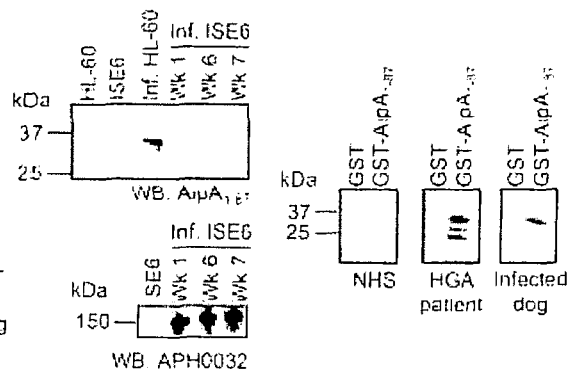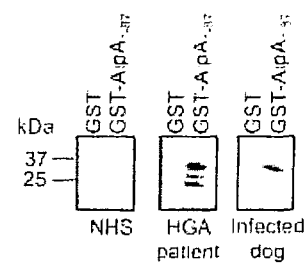
Figure 2D　　　　　　　Figure 2E　　　　　　　Figure 2F

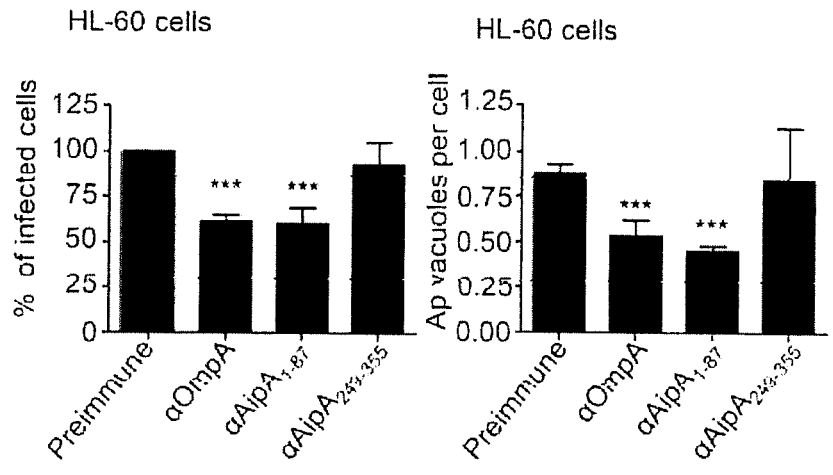
Figure 5A
Figure 5B
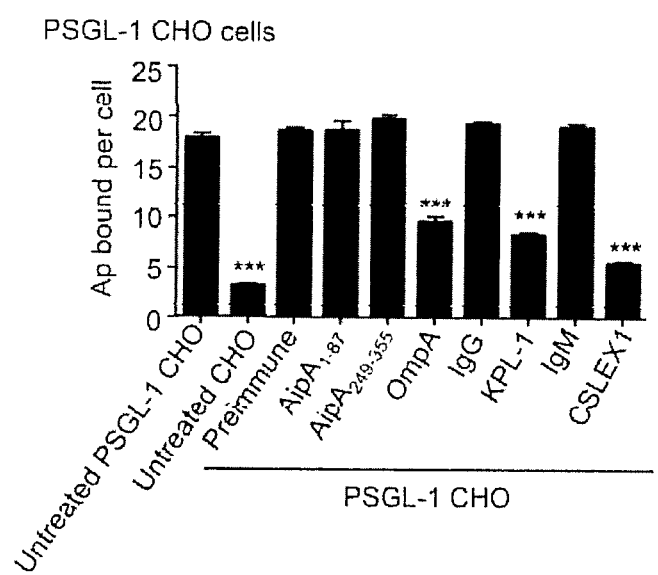
Figure 5C

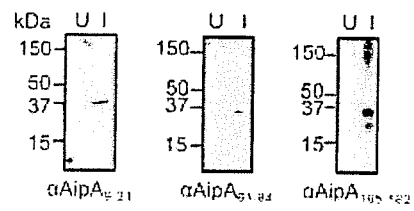
Figure 7A
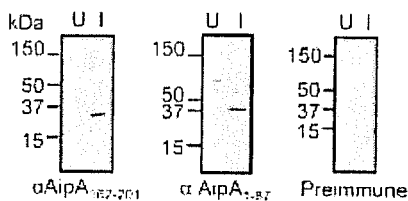
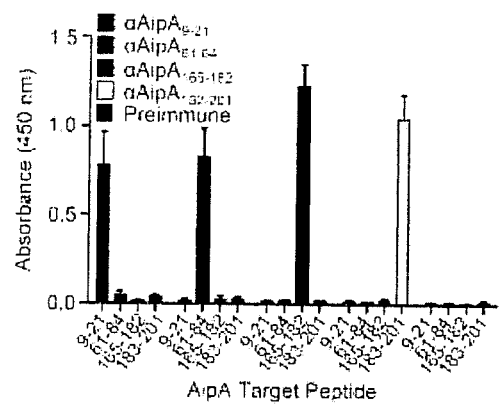
Figure 7B
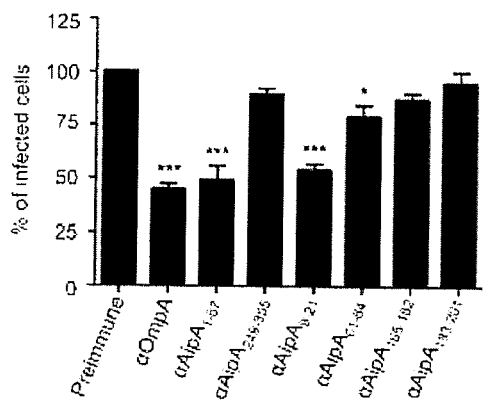
Figure 7C

```
                         10        20        30        40        50        60 ↓  ↓   70        80
                 ----------+---------+---------+---------+---------+---------+---------+---------+
SEQ ID NO: 77 NCH-1   MLRRSSFFCLLALLSVTSCGTLLPDSNVGVGRHDLGSHRSVAFAKKVEKVYFDIGKYDLKQPGFRVILDLVIQLRQDDSM
SEQ ID NO: 78 HZ     ********************************************************************************
SEQ ID NO: 79 HGE1   ********************************************************************************
SEQ ID NO: 80 Dog    ********************************************************************************
SEQ ID NO: 81 JM     ********************************************************************************
SEQ ID NO: 82 MRK    ********************************************************************************
SEQ ID NO: 83 CRT35  ********************************************************************************
SEQ ID NO: 84 CRT38  ********************************************************************************
SEQ ID NO: 85 NorV2  ******************************************************************K*****

90       100       110       120       130       140       150       160
                 ----------+---------+---------+---------+---------+---------+---------+---------+
SEQ ID NO: 77 NCH-1   YLVVIGHADATGTEEYSLALGEKRANAVKQFIIGCDKSLAFRVFTQSRGKAEPEVLVYSTDAQEVEKANAQHRRAVIVVE
SEQ ID NO: 78 HZ     ********************************************************************************
SEQ ID NO: 79 HGE1   ********************************************************************************
SEQ ID NO: 80 Dog    ********************************************************************************
SEQ ID NO: 81 JM     ********************************************************************************
SEQ ID NO: 82 MRK    ********************************************************************************
SEQ ID NO: 83 CRT35  ********************************************************************************
SEQ ID NO: 84 CRT38  ********************************************************************************
SEQ ID NO: 85 NorV2  ********************************************************************************

170       180       190       200
                 ----------+---------+---------+---------+------
SEQ ID NO: 77 NCH-1   FAHIPRSGVADMHAPVASSITSENSNASAEGEDMEASEFSSAIAN
SEQ ID NO: 78 HZ     ********************************************
SEQ ID NO: 79 HGE1   ********************************************
SEQ ID NO: 80 Dog    ********************************************
SEQ ID NO: 81 JM     ********************************************
SEQ ID NO: 82 MRK    ********************************************
SEQ ID NO: 83 CRT35  ********************************************
SEQ ID NO: 84 CRT38  ********************************************
SEQ ID NO: 85 NorV2  ***********************************E**K
```

Figure 10A

```
                               20        30        40        50        60 ↓  ↓   70
                         -+---------+---------+------  ---+---------+---------+----
              NCH-1       CGTLLPDSNVGVGRHDLGSHRSVAFAK-KVEKVYFDIGKYDLKQPGFRVILDLVIQL  SEQ ID NO: 77
              AM854       **-*FSKEK**M---*IVG---*P*SAGR*****FNEIS**L*G***RM  SEQ ID NO: 86
A. marginale  AMF640      **-*FSKEK**M---*IVG---*P*SAGR*****FNEIS**L*G***RM  SEQ ID NO: 87
              ACIS00486   *E-*FNKEK*NI---*I*G---*P*SAGR*****FNEIS**L*G***RM  SEQ ID NO: 88
              ECH0462     *L**NGCHFNSKHVPLVNVDHVFSNT*-TIIGF**ATIEDSD*TILEKVMQKA  SEQ ID NO: 89
Ehrlichia spp. Ecaj0563   LSSCKTTDH*----PLVNTDHVFSNM*-TII*F**ATIGDSD*AILEKVIQKA  SEQ ID NO: 90
              Erum5620    *H--FNSKH*----PLVNV*NLFSNI*-AID*****LD*TVI*DSD*VLLEK**QKA  SEQ ID NO: 91
```

Figure 10B

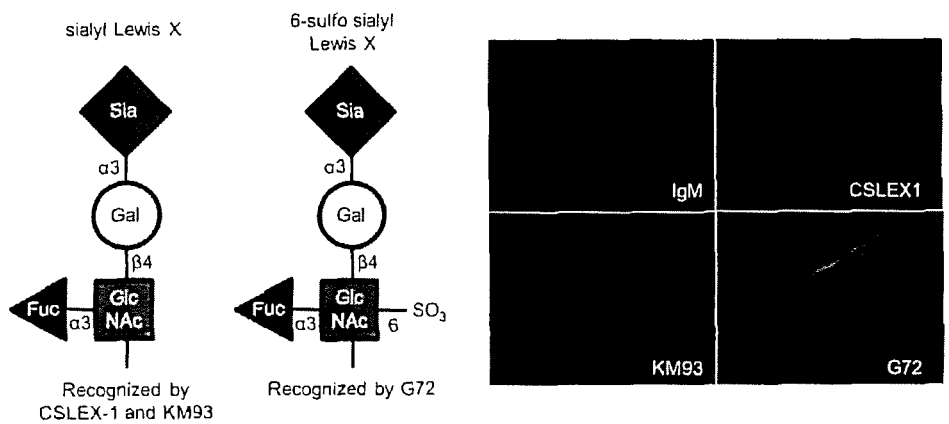
Figure 14A
Figure 14B
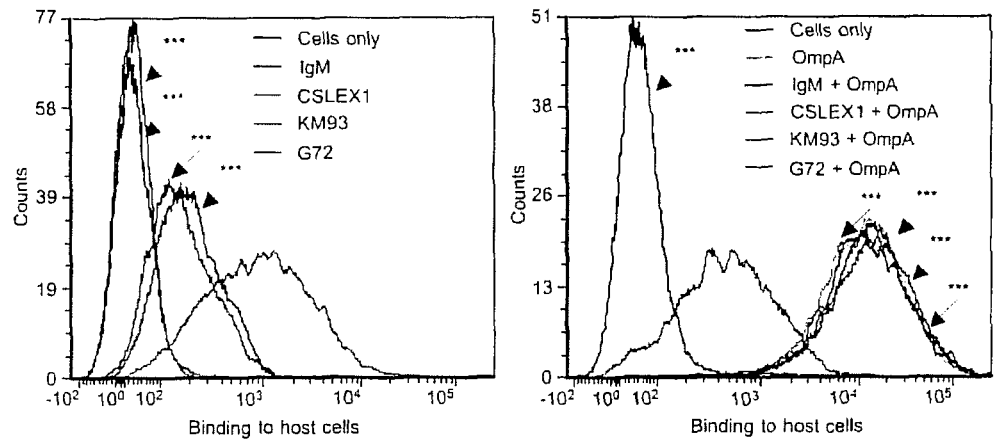
Figure 14C
Figure 14D

Figure 15A
Figure 15B
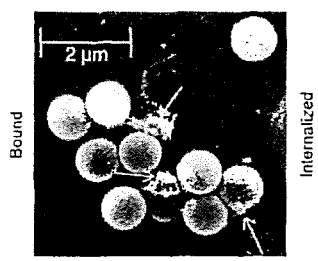
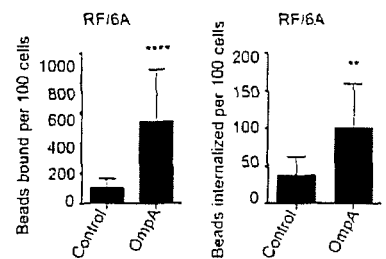
Figure 15C
Figure 15D

Figure 16A
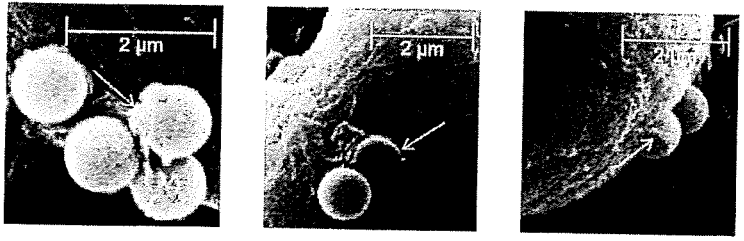
Figure 16B
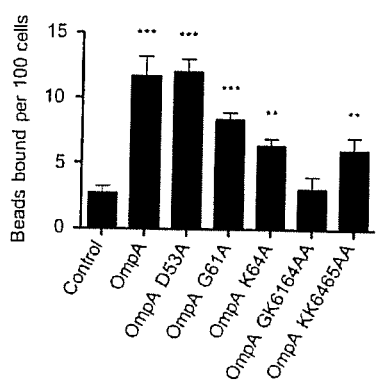
Figure 16C
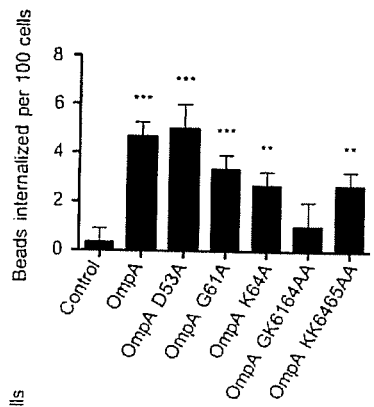
Figure 16D
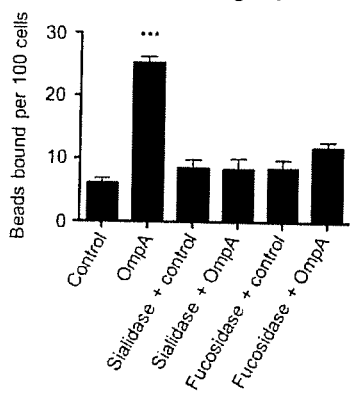
Figure 16E
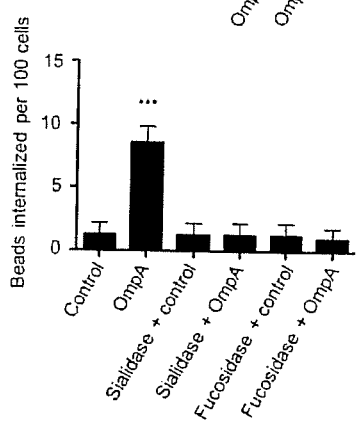
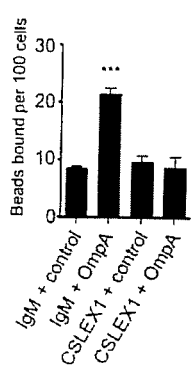
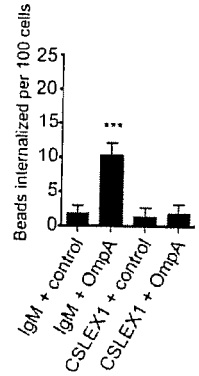
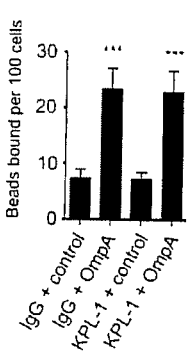
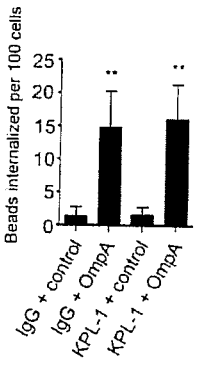
Figure 16F   Figure 16G   Figure 16H   Figure 16I

AIPA, OMPA, AND ASP14 IN VACCINE COMPOSITIONS AND DIAGNOSTIC TARGETS FOR *ANAPLASMA PHAGOCYTOPHILUM* INFECTION

PRIORITY

This application claims the benefit of U.S. application 61/935,012, filed Feb. 3, 2014. This application is incorporated herein by reference in its entirety.

FIELD OF THE INVENTION

The invention generally relates to a vaccine or immunogen and diagnostic for anaplasmosis in mammals. In particular, the invention provides *Anaplasma phagocytophilum* (AipA) protein and fragments thereof comprising an invasin domain for these purposes, used alone or in combination with one or both of *Anaplasma phagocytophilum* outer surface protein A (OmpA) and/or antigenic fragments thereof, and *Anaplasma phagocytophilum* surface protein 14 (Asp14) and/or antigenic fragments thereof.

SEQUENCE LISTING

This document incorporates by reference an electronic sequence listing text file, which was electronically submitted along with this document. The text file is named 02940981TA_ST25.txt, is 108 kilobytes, and was created on Jan. 30, 2015.

BACKGROUND OF THE INVENTION

*Anaplasma phagocytophilum* (Aph) is a tick-transmitted obligate intracellular bacterium of the family Anaplasmataceae that can infect humans, livestock, companion animals, and wild animals. In addition to Aph, the Anaplasmataceae family members include *Anaplasma marginale, Anaplasma platys, Ehrlichia chaffeensis, Ehrlichia canis*, and *Ehrlichia ruminatium*, among others, and all of these cause similar infections known collectively as ehrlichiosis or anaplasmosis. When humans contract an Aph infection, it is more specifically known as human granulocytic anaplasmosis (HGA) and is marked by fever and increased susceptibility to potentially fatal opportunistic infections. Other possible disease manifestations include leukopenia, thrombocytopenia, and elevated serum transaminase levels.

Unfortunately, no vaccines against these infectious agents are currently available. Instead, antibiotic treatments with doxycycline or tetracycline are currently the frontline treatments for anaplasmosis/ehrlichiosis and can be effective. However, the overuse of antibiotics is currently of great concern, and many individuals, such as those that are allergic to the drug, pregnant women, and small children, either cannot or are not advised to take doxycycline. Also troubling is the lack of tools for rapid and definitive diagnosis of anaplasmosis/ehrlichiosis in any species other than dogs.

HGA is an emerging and potentially fatal disease transmitted by the same vectors that transmit Lyme Disease, primarily ticks and deer, but other animal and human hosts can complete the vector cycle and therefore extend the spread of disease. In the U.S., HGA occurs primarily in the Northeast, Upper Midwest, and Northern California. Since HGA became a reportable disease in the U.S. in 1999, the number of cases has risen annually, reaching 2,037 in 2013. Since diagnostic tools for HGA are lacking, the number of actual cases is likely to be much higher. HGA is increasingly recognized in Europe and Asia, and Aph infection is now the most widespread tick-transmitted disease of animals in Europe. Domestic animals, such as dogs and cats, and livestock, such as sheep can be become infected.

As the name implies, an obligate intracellular bacterium must enter a target cell in its human or animal host to survive, replicate, and move to the next host. When an *Anaplasma* spp. or *Ehrlichia* spp. infected tick bites a subject, the bacteria is transferred from the tick salivary glands into the tissues of the host or into the bloodstream where they bind to the surface of host cells (especially neutrophils) and are internalized by being taken up into vacuoles that form around each bacterium. For *A. phagocytophilum*, optimal invasion of mammalian host cells is known to involve multiple cell surface proteins (various adhesins and invasins) which function cooperatively. Within the cell, a resident bacterium prevents the vacuole from merging with lysosomes, which would otherwise destroy the bacterium. In doing so, the bacterium converts the cell into a protective niche that favors bacterial survival and completion of its zoonotic cycle. For example, *A. phagocytophilum* undergoes a biphasic developmental cycle within neutrophils in which it transitions between an infectious morphotype (dense-cored cell; DC) and a non-infectious, replicative morphotype (reticulate cell; RC). Subsequently, if the Aph infected host is bitten by a tick, DC cells from the host can be ingested by the tick during the blood meal, and the disease is then transferred to new hosts when the infected tick takes another blood meal. However, HGA can also be transmitted perinatally and by blood transfusion, and possibly nosocomially.

While the hallmark of Aph infection is Aph colonization of neutrophils, Aph has also been detected in the microvascular endothelium of heart and liver in experimentally infected severe combined immunodeficiency mice. For experimental purposes, promyelocytic and endothelial cell lines are also useful as in vitro models for studying Aph-host cell interactions. It has been shown that when naïve neutrophils or HL-60 cells are overlaid on Aph-infected endothelial cells, the bacterium rapidly transmigrates into the myeloid cells, demonstrating that Aph infects endothelial cells in vitro and suggesting that the bacterium may transmigrate between endothelial cells and neutrophils during the course of mammalian in vivo infections.

As noted above, humans are not the only species that are infected by members of the Anaplasmataceae family. For example, *A. marginale* infects bovine erythrocytes. Bovine anaplasmosis causes severe economic loss in many countries, mainly due to the high morbidity and mortality in susceptible cattle herds. Several parameters contribute to the losses due to anaplasmosis and include: low weight gain, reduction in milk production, abortion, the cost of anaplasmosis treatments, and mortality. The losses incurred by the U.S. cattle industry as a result of anaplasmosis are estimated to be $300 million per year whereas in Latin America, losses are calculated to be approximately $800 million per year.

Proteins which mediate the infection of endothelial cells and/or the dissemination of bacteria into the microvasculature of heart and liver are attractive targets for preventing disease caused by Anaplasmataceae bacteria such as Aph. In particular, targeting Aph proteins that are conserved among related Anaplasmataceae family members may also reduce or block transmission of disease caused by a broad spectrum of Anaplasmataceae species. In addition, it would be advantageous to have available a rapid and highly accurate diagnostic test for detecting Anaplasmataceae species infection, especially one that allowed detection early in infection. Unfortunately, no FDA-approved vaccines against Anaplasmataceae species having purified antigens are currently available.

The current gold standard serologic test for diagnosis of anaplasmosis in humans is indirect immunofluorescence assays (IFA) performed as timed pairs over a period of a few weeks, only available in specialized reference laboratories. This assay measures non-specific increases in IgM and IgG antibody levels. However, IgM antibodies, which usually rise at the same time as IgG near the end of the first week of illness and remain elevated for months or longer, are even less specific than IgG antibodies and more likely to result in a false positive. Serologic tests based on enzyme immunoassay (EIA) technology are available from some commercial laboratories. However, EIA tests are qualitative rather than quantitative, meaning they only provide a positive/negative result, and are less useful to measure changes in antibody titers between paired specimens. Furthermore, some EIA assays rely on the evaluation of IgM antibody alone, which again may have a higher frequency of false positive results. Between 5-10% of currently healthy people in some areas may have elevated antibody titers due to past exposure to Aph or to other Anaplasmataceae family members. If only one sample is tested, it can be difficult to interpret. A four-fold rise in antibody titer is needed to achieve significance in paired samples taken weeks apart. Thus, tools for a rapid and definitive diagnosis in any species other than dogs are lacking.

U.S. Pat. No. 7,906,296 B2 to Beall et al teaches polynucleotide sequences from major outer surface protein P44 of *Anaplasma platys* (Apl), which causes tick-born anaplasmosis in dogs. P44 and peptides from the translated protein can be used for detection of Apl and Aph infection and/or to elicit an immune response in vivo and confer resistance to anaplasmosis caused by Apl or Aph.

U.S. Pat. Nos. 8,158,370; 8,303,959 and US 2013/0064842, all to Liu et al, teach the use of P44 surface proteins from various strain variants of Aph to diagnose and protect against anaplasmosis.

U.S. Pat. No. 8,609,350 B2 to Liu et al. teaches polypeptides from Aph to diagnose and protect against anaplasmosis. The Aph sequences were derived from APH_0915, which encodes a hypothetical open reading frame of a protein of unknown function.

PCT/US2013/047325 to Carlyon, which is herein incorporated by reference, relates to the invasin proteins OmpA and Asp14, and fragments thereof comprising conserved invasin domains. The proteins and fragments are used as therapeutic and diagnostic agents for *A. phagocytophilum* infection.

Nelson, C. M., et al. (*BMC Genomics* 9, 364; 2008) used a whole genome transcriptional profiling tiling array analysis to detect *A. phagocytophilum* genes that are upregulated in vitro during infection of mammalian versus tick cell lines. Many of the proteins encoded by the identified genes were assigned a designation of "hypothetical protein" and of these, several had a predicted cellular location of "outer membrane", among them APH0915. However, no further information about this putative protein was provided, and no confirmation of its status as an outer membrane protein or possible significance was shown.

A need remains in the art for immunogenic compositions and vaccines to combat Anaplasmataceae infections and for methods to rapidly and accurately diagnose new cases of these diseases, especially with respect to Anaplasmataceae infections that cause anaplasmosis and HGA.

SUMMARY OF THE INVENTION

Obligate intracellular bacteria such as Anaplasmataceae use outer membrane proteins called invasins to enter and infect eukaryotic host cells. Since these organisms are incapable of extracellular survival, blocking this internalization step prevents infection and transmission of diseases caused by Anaplasmataceae. Thus, the identification and characterization of Anaplasmataceae invasin proteins provides a path forward for the development of therapies to treat and/or prevent Anaplasmataceae infections. In addition, the discovery and characterization of such invasins also leads to improved diagnostic methods for detecting exposure to and/or infection with Anaplasmataceae, so that proper therapeutic measures can be undertaken.

Provided herein is a newly characterized invasin protein from *A. phagocytophilum*, denoted AipA (*Anaplasma phagocytophilum* invasion protein A) (SEQ ID NO: 13). This protein corresponds to protein APH0915 identified by Nelson et al. (2008). The studies presented in Example 1 below demonstrate that AipA is in fact an outer membrane protein, and further that AipA is, surprisingly, an *A. phagocytophilum* invasin protein that is useful as a therapeutic and diagnostic agent. In addition, the detailed characterization of AipA presented herein has identified particular fragments of AipA which constitute domains required for the protein to function as an invasion, so-called effector or invasin domains, that are also useful as therapeutic and diagnostic agents. Further, AipA is unique to *A. phagocytophilum* i.e. homologs of AipA are not present in other Anaplasmataceae species. Accordingly, certain aspects of this disclosure provide AipA and/or one or more functional fragments thereof for use as components of vaccines and/or immunogenic compositions to prevent or treat *A. phagocytophilum* infections. Other aspects provide AipA protein and fragments thereof comprising invasin domains, and antibodies thereto, as diagnostic targets to detect exposure to and/or infection with *A. phagocytophilum*. Exemplary functional domains of AipA include but are not limited to fragments which include a linear amino acid sequence encompassing amino acids 1-87 inclusive, and amino acids 9-21 (SEQ ID NO: 13), inclusive.

In other aspects, AipA and/or one or more of the identified functional fragments thereof are used for these purposes in combination with one or more additional invasins and/or functional domains of the additional invasins. Exemplary additional invasins include but are not limited to Asp14 (14-kDa *A. phagocytophilum* surface protein; APH0248) and OmpA (Outer membrane protein A; APH0338 in the annotated *A. phagocytophilum* proteome), and homologs thereof from other species, e.g. other Anaplasmataceae species. Exemplary functional domains of Asp 14 include but are not limited to fragments which include the linear amino acid sequence from amino acids: 19-60, 101-112, 101-124, and 113-124, all of which are inclusive. In some aspects, the sequence is that which encompasses amino acids 113-124. Exemplary functional domains of OmpA include but are not limited to fragments which include the amino acid sequence from amino acids: 19-74, 59-74, 48-56, 86-101, 135-155, and 24-121, all of which are inclusive. In some aspects, the sequence is that which encompasses amino acids 59-74. Accordingly, in some aspects, what is provided herein are various combinations of these three *A. phagocytophilum* surface proteins and/or invasion domain-containing fragments thereof, as well as antibodies to one or more of these proteins or fragments, as protective/therapeutic/diagnostic agents or targets to treat or detect Anaplasmataceae infection.

Significantly, it has been discovered that these three invasins work together synergistically to promote infection of host cells, and that combinations of two of AipA, Asp14 and OmpA proteins (or peptides comprising invasin domains thereof) promote infection more effectively than any one alone, and, in some aspects, the most effective combination utilizes all three. Conversely, to prevent infection of host cells from infection, some aspects of the invention provide therapeutic agents which are or which are based on combinations of at least two and usually all three of the proteins or relevant fragments thereof. For example, linear peptide domains of each protein that mediate invasin and combinations of linear peptide domains, are encompassed, as are antibodies targeting one, two, or all three domains. Such agents are shown herein to simultaneously work synergistically to nearly abolish *A. phagocytophilum* invasion of host cells. For example, antisera combinations targeting two of the three invasins together more effectively inhibited infection than an antiserum targeting an individual protein, and the most effective blocking of *A. phagocytophilum* infection was achieved using antisera against all three invasins.

An embodiment of the invention is a composition comprising one or more polypeptides which include one copy or more than one copy of SEQ ID NO:14 together with one copy or more than one copy of either or both of SEQ ID NO: 3 and SEQ ID NO: 06. For example, a single polypeptide might include 1, 2, or 3 copies of SEQ ID NO: 14 together with 0, 1, 2 or 3 copies of SEQ ID NO. 3 and/or 0, 1, 2 or 3 copies of SEQ ID NO. 6, and may include additional amino acid sequences of interest (e.g. linkers, etc.). Or the composition may include two or more polypeptides wherein one polypeptide is or includes one or more copies of SEQ ID No. 14, and the other polypeptide(s) is/are or include(s) one or more copies of either or both of SEQ ID No. 3 and SEQ ID No. 6.

In exemplary embodiments, the isolated peptides are in a vehicle or carrier suitable for administration to a subject. At least one of the polypeptides may be linked to an amino acid spacer, an amino acid linker, a signal sequence, a stop transfer sequence, a transmembrane domain, a protein purification ligand, a heterologous protein, or one or more additional polypeptides comprising SEQ ID NO:01, 02, 03, 04, 05, 06, 13, 14, or 15 or a combination thereof. An exemplary embodiment is one or more polypeptides linked to a protein purification ligand, and protein purification ligands are a peptide encoding a histidine tag.

Another embodiment of the invention comprises one or more polypeptides selected from the group consisting of SEQ ID NO:01, SEQ ID NO:02, and SEQ ID NO:03. Another embodiment of the invention comprises one or more polypeptides selected from the group consisting of SEQ ID NO:04, SEQ ID NO:05, and SEQ ID NO:06. Another embodiment of the invention comprises one or more polypeptides selected from the group consisting of SEQ ID NO:13, SEQ ID NO:14, and SEQ ID NO:15.

Another embodiment of the invention includes nucleic acids and nucleic acid based compositions that can be used for generating an immune response. In particular embodiments, the compositions may take the form of DNA vaccines or other nucleic acid vaccines which comprise nucleic acids encoding one or more polypeptides as described herein, e.g. polypeptides which include one or more copies of SEQ ID NO:14, optionally together with one or more copies of either or both SEQ ID NO: 3 and SEQ ID NO. 06. For example, a suitable composition might include a single nucleic acid in a vector (e.g., adenovirus, baculovirus, etc.) that codes for a single polypeptide or multiple polypeptides that include 1, 2, or 3 copies of SEQ ID NO: 14, together with 0, 1, 2 or 3 copies of SEQ ID NO. 3; and 0, 1, 2 or 3 copies of SEQ ID NO. 6, and may include additional amino acid sequences of interest, linkers, etc. Or the composition may include two or more nucleic acids, each on a vector, which code for a polypeptide that is or includes one or more repeats of SEQ ID NO. 14, and code for another polypeptide is or includes one or more repeats of either or both SEQ ID NO. 3 and SEQ ID NO. 6. DNA may also be provided without a vector and be combined with material which might also be driven into a cell or living tissue by an agent which crosses into a cell (e.g., Lipofectamine). Furthermore, the DNA vaccines might be incorporated into a host bacterium that is itself administered as a vaccine to a subject.

Another embodiment of the invention is a method of protecting a subject from acquiring a zoonotic disease and/or treating a zoonotic disease in a subject by the step of administering a composition an immunogenic composition comprising the isolated polypeptide represented by SEQ ID NO:14 and at least one of the isolated polypeptides represented by SEQ ID NO:03 and SEQ ID NO:06. At least one of the polypeptides may be linked to an amino acid spacer, an amino acid linker, a signal sequence, a stop transfer sequence, a transmembrane domain, a protein purification ligand, a heterologous protein, or one or more additional polypeptides comprising SEQ ID NO:01, 02, 03, 04, 05, 06, 13, 14, or 15; or a combination thereof. The zoonotic disease may be one caused by an obligate intracellular Anaplasmataceae bacterium selected from the group consisting of *Anaplasma phagocytophilum*, *Anaplasma marginale*, *Anaplasma platys*, *Ehrlichia chaffeensis*, *Ehrlichia canis*, *Ehrlichia ruminantium*, and *Ehrlichia ewingii*. When the subject is a human, the zoonotic disease may be human granulocytic anaplasmosis (HGA) if caused by *Anaplasma phagocytophilum*. When the subject is an animal, the zoonotic disease may be anaplasmosis. If caused by an *Ehrlichia* species, the human zoonotice disease may be monocytic ehrlichiosis or ehrlichiosis.

Another embodiment of the invention is a method of detecting antibodies that specifically bind an Anaplasmataceae polypeptide in a test sample. The method may include the steps of contacting a test sample, under conditions that allow polypeptide-antibody complexes to form, with a composition that includes at least one or more polypeptides encoding all or a portion of SEQ ID NO:01, SEQ ID NO:04, and/or SEQ ID NO:13, and detecting said polypeptide-antibody complexes, wherein the detection is an indication that antibodies specific for Anaplasmataceae Asp14, OmpA, or AipA are present in the test sample. Alternatively, antibodies are generated to at least one or more polypeptides encoding all or a portion of SEQ ID NO:01, SEQ ID NO:04, and/or SEQ ID NO:13, and the antibodies are used to detect the presence of AipA and/or OmpA and/or Asp14 protein in a biological sample from a subject. The method may be an assay selected from the group consisting of an immunoblot and an enzyme-linked immunosorbent assay (ELISA). An exemplary embodiment of this methodology includes using at least one polypeptide which is or includes SEQ ID NO:03, SEQ ID NO:06, or SEQ ID NO:14 in the assay, whereby infection with obligate intracellular Anaplasmataceae is

BRIEF DESCRIPTION OF THE DRAWINGS

FIG. 2A-F. Differential expression profiling of AipA throughout the *A. phagocytophilum* life cycle. (A) aipA transcriptional profile during *A. phagocytophilum* infection of HL-60 cells. DC bacteria were incubated with HL-60 cells to establish a synchronous infection. Total RNA isolated from the DC inoculum and infected host cells at several postinfection time points was subjected to reverse transcriptase-quantitative PCR (RT-qPCR). Relative aipA transcript levels were normalized to *A. phagocytophilum* 16s rRNA gene transcript levels. To determine relative aipA transcription between RC and DC organisms, normalized aipA transcript levels per time point were calculated as the fold change in expression relative to expression at 16 h, a time point at which the entire bacterial population is in the DC morphotype. Data are the means±standard deviations (SD) for triplicate samples and are representative of two experiments having similar results. (B) Western blot screening of whole-cell lysates of uninfected (U) and *A. phagocytophilum* infected HL-60 cells (I) using mouse antiserum raised against GST-AipA$_{1-87}$ (αAipA$_{1-87}$) and GST-AipA$_{249-355}$ (αAipA$_{249-355}$). (C) AipA expression over the course of infection of mammalian host cells. RF/6A cells that had been synchronously infected with *A. phagocytophilum* (Ap) were screened with antibodies targeting Msp2 (P44) (to denote all *A. phagocytophilum* inclusions) and AipA viewed by confocal microscopy. Data presented are the mean percentages SD of Msp2 (P44)-positive *A. phagocytophilum* inclusions that were also AipA-positive. At least 100 bacterial inclusions were scored per time point. (D) aipA and groEL expression during transmission feeding of *A. phagocytophilum* infected ticks on naïve mice. *A. phagocytophilum*-infected *I. scapularis* nymphs were allowed to feed on mice for 72 h. Total RNA recovered from unfed and transmission-fed ticks that had been removed at 24, 48, and 72 h postattachment was subjected to RT-qPCR. Relative aipA and groEL transcript levels were normalized to *A. phagocytophilum* 16S rRNA gene levels. (E) AipA is not expressed during *A. phagocytophilum* infection of a tick cell line. Western blot analysis of uninfected and *A. phagocytophilum* infected (Inf.) HL-60 and ISE6 cells using antiserum specific for AipA$_{1-87}$ or APH0032. The number of weeks (Wk.) during which *A. phagocytophilum* was maintained in ISE6 cells are indicated in vivo and elicits a humoral immune response. Western blot analysis of GST and GST-AipA$_{1-87}$ screened with sera from an HGA patient and from an *A. phagocytophilum* infected dog. Results presented in panels B to F are each representative of at two to three independent experiments with similar results. Statistically significant (*, P<0.05; , P<0.005; *, P<0.001) values are indicated.

FIG. 5A-C. Pretreatment of *A. phagocytophilum* with AipA$_{1-87}$ antiserum inhibits infection of HL-60 cells but does not alter binding to sLe$^x$-capped PSGL-1. *A. phagocytophilum* DC organisms were exposed to antiserum targeting AipA$_{1-87}$, AipA$_{249-355}$, OmpA, or preimmune serum and then incubated with HL-60 (A and B), PSGL-1 CHO cells, or untransfected CHO cells (C). The infection of HL-60 cells was allowed to proceed for 24 h prior to being assessed, while bacterial binding to PSGL-1 CHO cells was assessed immediately. The mean±standard deviations of percentages of infected HL-60 cells (A), *A. phagocytophilum* (Ap) vacuolar inclusions per HL-60 cell (B), and bound DC organisms per PSGL-1 CHO cell or untransfected CHO cell (C) were determined using immunofluorescence microscopy. Additional positive controls for blocking *A. phagocytophilum* to PSGL-1 CHO cells, besides incubating bacteria with OmpA antiserum, were PSGL-1 CHO cells that had been incubated with PSGL-1 N-terminus blocking antibody KPL-1 or sLe$^x$-blocking antibody CSLEX1 prior to the addition of bacteria. Negative controls were PGSL-1 CHO cells that had been incubated with isotype control antibodies prior to the addition of bacteria. Results shown are relative to GST-treated host cells and are the means±SD for three experiments. Statistically significant (***, P<0.001) values are indicated.

FIG. 7A-C. AipA residues 9-21 are critical for establishing infection in host cells. (A) Western blot analyses in which rabbit antiserum targeting $AipA_{9-21}$, $AipA_{61-84}$, $AipA_{165-182}$, $AipA_{183-201}$, $AipA_{1-87}$, or preimmune rabbit serum was used to screen whole cell lysates of uninfected (U) and *A. phagocytophilum* infected HL-60 cells (I). Data are representative of two experiments with similar results. (B) ELISA in which $AipA_{9-21}$, $AipA_{61-84}$, $AipA_{165-182}$, and $AipA_{183-201}$, antibodies were used to screen wells coated with peptides corresponding to AipA residues 9-21, 61-84, 165-182 and 183-201. Each antiserum only recognized the peptide against which it had been raised. Results shown are the mean (±SD) of triplicate samples. Data are representative of three experiments with similar results. (C) Pretreatment of *A. phagocytophilum* with $AipA_{9-21}$ antiserum inhibits infection of HL-60 cells. DC bacteria were pretreated with antiserum specific for $AipA_{9-21}$, $AipA_{61-84}$, $AipA_{165-182}$, $AipA_{183-201}$, $AipA_{1-87}$, $AipA_{249-355}$, OmpA, or preimmune serum for 30 min. Next, the treated bacteria were incubated with HL-60 cells for 60 min. After removal of unbound bacteria, host cells were incubated for 24 h and subsequently examined using Msp2 (P44) antibody and confocal microscopy to assess the percentage of infected cells. Results shown are relative to preimmune serum-treated host cells and are the means±SD for six experiments. Statistically significant (*, P<0.05; , P<0.005; *, P<0.001) values are indicated.

FIG. 10A-B. OmpA is highly conserved among *A. phagocytophilum* isolates and its key binding residues exhibit variable conservation among Anaplasmataceae species. (A) Alignment of OmpA amino acid sequence from the *A. phagocytophilum* strain (isolated from a human patient in Massachusetts), with OmpA sequences from *A. phagocytophilum* strains HZ (human; New York), HGE1 (human; Minnesota), Dog (Minnesota), JM (jumping mouse; Minnesota), MRK (horse; California), ApVar-1 isolates CRT35 and CRT38 (both from ticks; Minnesota), and NorV2 (lamb; Norway). (B) Aligment of NCH-1 OmpA amino acids 19 to 74 with corresponding regions of OmpA homologs from the *A. marginale* St. Maries strain (AM854), *A. marginale* Florida strain (AMF640), *A. marginale* subsp. centrale Israel starin (ACIS00486) *E. chaffeensis* Arkansas strain (ECH0462), *Ehrlichia canis* Jake strain (Ecaj0563), and the *Ehrlichia ruminantium* Welgevonden strain (Erum5620). The binding domain corresponding to NCH-1 OmpA comprises residues 59 to 74. Numbers above the alignments in (A) and (B) denote amino acid position numbers. The arrows in (A) and (B) denote *A. phagocytophilum* OmpA G61 and K64, which were predicted to form interactions with $sLe^x$ in FIG. 9 panels E and F and were shown to be critical for OmpA to bind to and mediate infection of mammaliam host cells in FIGS. 8 and 11.

GST1087 OmpA proteins having the CLNHL peptide inserted between OmpA amino acids 67 and 68 or having G61 and/or K64 mutated to alanine are unable to bind to competitively inhibit *A. phagocytophilum* infection of mammalian host cells. HL-60 cells were incubated with DC organisms in the presence of GST alone, GST-OmpA, GST-OmpA proteins bearing insertions of CLNHL (SEQ ID NO:75) between the indicated residues (A), or GST-OmpA proteins having the indicated amino acids substituted with alanine (B and C) for 1 h. After washing to remove unbound bacteria, host cells were incubated for 24 h and subsequently examined by immunofluorescence microscopy to determine the percentage of infected cells (A and B) or the mean number (+SD) of morulae per cell (C). Results shown in (A), (B), and (C) are the means±SD for six to twelve combined experiments. The data presented in panel C are the normalized values of six to twelve experiments. Statistically significant ( P<0.005; *P<0.001) values are indicated. (D) Flow cytometric analysis of His-OmpA and His-OmpA proteins bearing alanine substitutions binding to RF/6A cells. Data are representative of two experiments with similar results.

FIG. 12A-C. Treatment with α1,3/4-fucosidase reduces *A. phagocytophilum* binding to PSGL-1 CHO cells and binding to and infection of RF/6A endothelial cells. PSGL-1 CHO cells (A) and RF/6A cells (B and C) were treated with α1,3/4-fucosidase (+ fucosidase) or vehicle control (− fucosidase). Fucosidase- and mock-treated cells were incubated with *A. phagocytophilum* DC organisms. Following the removal of unbound bacteria, the infection of RF/6A cells was allowed to proceed for 24 h prior to being assessed, while bacterial binding to PSGL-1 CHO and RF/6A cells was examined immediately. The mean±SD of bound DC bacteria per PSGL-1 CHO (A) or RF/6A cell (B) or percentage of infected RF/6A cells (C) were determined using immunofluorescence microscopy. Results shown are the means±SD for three combined experiments. Statistically significant (***P<0.001) values are indicated.

FIG. 13A-E. OmpA interacts with α1,3-fucose on mammalian host cell surfaces. (A to D) RF/6A cells were treated with α1,3/4-fucosidase (A and C), α2,3/6-sialidase (B and D), or vehicle control (− fucosidase and − sialidase, respectively). Glycosidase- and mock-treated cells were incubated with α1,3/6-fucose-specific lectin, AAL; the α2,3-sialic acid-specific lectin, MAL II; His-OmpA; or His-Asp14. (A) The host cells were fixed and screened using immmunofluorescence microscopy (A and B) or flow cytometry (C and D) to detect lectin, His-OmpA, or His-Asp14 binding to host cells. (E) AAL and MAL II competitively inhibit His-OmpA binding to mammalian host cells. RF/6A cells were incubated with AAL and MAL II, after which His-OmpA was added. Following the removal of unbound recombinant protein, His-OmpA bound on RF/6A cell surfaces was detected by flow cytometry. Statistically significant (***P<0.001) values are indicated. Results shown are representative of three experiments with similar results.

FIG. 14A-D. OmpA interacts with 6-sulfo $sLe^x$ on RF/6A endothelial cell surfaces. (A) Schematic representations of $sLe^x$ and 6-sulfo $sLe^x$. Individual sugar and glycosidic linkages are indicated. (B and C) 6-sulfo $sLe^x$ is present in high abundance relative to $sLe^x$ on RF/6A cells. RF/6A cells were screened with $sLe^x$-specific antibodies, CSLEX1 and KM93; 6-sulfo $sLe^x$-specific antibody, G72; or IgM isotype control followed by detection of cell surface bound antibodies using immunofluorescence microscopy (B) and flow cytometry (C). (D) Antibody blocking of 6-sulfo $sLe^x$ inhibits His-OmpA binding to RF/6A cells. RF/6A cells were incubated with CSLEX1, KM93, G72, IgM, or vehicle (Cells only) followed by the addition of His-OmpA, and washing to remove unbound recombinant protein. Flow cytometry was used to detect bound His-OmpA. Statistically significant (***P<0.001) values are indicated. Results shown are representative of two experiments with similar results.

FIG. 15A-D. OmpA coated beads bind to and are internalized by non-phagocytic endothelial cells. (A) Confirmation of recombinant OmpA conjugation to inert beads. Fluorescent OmpA-coated microspheres (OmpA beads) were incubated with OmpA antibody (αOmpA) or isotype control. Unconjugated (Control) beads were included as a negative control. Bound antibody was detected using immunofluorescence microscopy. (B to D) OmpA coated beads bind to and are internalized by nonphagocytic RF/6A cells. OmpA coated beads were incubated with RF/6A cells for 1 h after which unbound beads were washed off. Cells were screened with OmpA antibody and examined using immunofluorescence (B and D) or scanning electron microscopy (C) to assess binding or were incubated further to allow for bead uptake. To assess for internalized beads, the host cells were treated with trypsin, washed, incubated overnight for the endothelial cells to re-adhere, fixed, and screened with OmpA antibody and immunofluorescence microscopy. (B) DIC, differential interference contrast microscopy. (C) Two scanning electron micrographs depicting bound or internalized OmpA coated beads. Arrows denote filopodia-like structures bound to beads. Scale bars are indicated. Results in (D) are representative of thirteen experiments with similar results. Statistically significant ( P<0.005; **P<0.0001) values are indicated.

FIG. 16A-I. OmpA coated bead binding to and uptake by promyelocytic HL-60 cells involve OmpA residues G61 and K64 and are dependent on $sLe^x$. (A) Scanning electron micrographs depicting OmpA coated beads bound to and being internalized by HL-60 cells. Arrows point to filopodia-like structures adhered to beads. Scale bars are indicated. (B and C) HL-60 cells were incubated with beads coated with OmpA, OmpA proteins having the indicated amino acids substituted with alanine, or non-coated control beads. The numbers of bound and internalized beads were determined using immunofluorescence microscopy. (D to I) HL-60 cells were incubated with α2,3/6-sialidase, α1,3/4-fucosidase, or vehicle only (D and E), $sLe^x$antibody CSLEX1 or IgM isotype control (F and G), or PSGL-1 N-terminus antibody KPL-1 or IgG isotype control (H and I) before being incubated with OmpA coated or non-coated control beads. The numbers of bound and internalized beads were assessed using immunofluorescence microscopy. Results in (B) through (I) are the mean±SD of triplicate samples and are representative of three independent experiments with similar results. Statistically significant ( P<0.005; *P<0.001) values are indicated.

FIG. 17A-D. The Asp14 binding domain is contained within amino acids 113 to 124. (A) Pretreatment of *A. phagocytophilum* with Asp14113-124 antiserum inhibits infection of HL-60 cells in a dose-dependent manner. DC bacteria were incubated with 200 μg/ml of preimmune serum, 200 μg/ml of serum raised against full-length Asp14, or two-fold serially-diluted concentrations of anti-Asp1498-112 or anti-Asp14113-124 ranging from 0 to 200 μg/ml and then incubated with HL-60 cells. The infection was allowed to proceed for 24 h prior to being assessed by immunofluorescence microscopy for the percentage of infected cells. (B) A combination of antisera targeting OmpA59-74 and Asp14113-124 inhibits *A. phagocytophilum* infection of HL-60 cells better than serum targeting either binding domain alone. DC organisms were exposed to preimmune serum or antisera targeting OmpA59-74, Asp14113-124, OmpA59-74 plus Asp1498-112, or anti-Asp14113-124 together with OmpA59-74, OmpA23-40, or OmpA43-58 antibodies. The cells were fixed and screened using immunofluorescence microscopy to determine the percentages of infected cells. (C and D) OmpA59-74 and Asp14113-124 Fab fragments effectively inhibit *A. phagocytophilum* infection of HL-60 cells. DC bacteria were incubated with Fab fragments derived from preimmune serum, antibodies targeting OmpA23-40, OmpA41-58, OmpA59-74, Asp1498-112, Asp14113-124, or OmpA59-74 Fab fragment together with Asp14113-124 Fab fragment. The cells were fixed and screened to determine the percentages of infected cells (C) and morulae per cell (D). Results presented in (B) to (D) are relative to host cells that had been incubated with bacteria treated with preimmune serum. Results presented in (A) and (B) are the means±SD for three experiments. Results in (C) and (D) are the mean±SD of triplicate samples and are representative of two experiments with similar results. Statistically significant (* $P<0.05$;  $P<0.005$; *$P<0.001$) values are indicated.

Figure 18A:
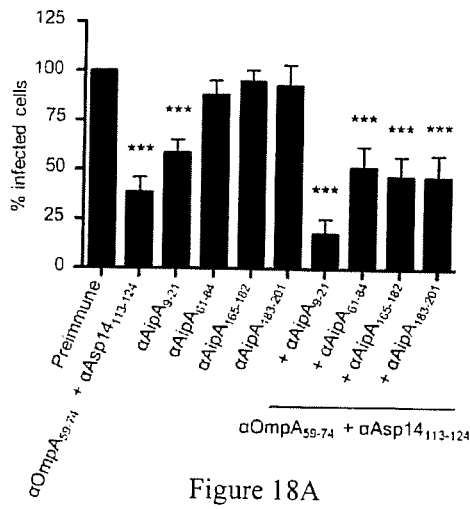
Figure 18B:
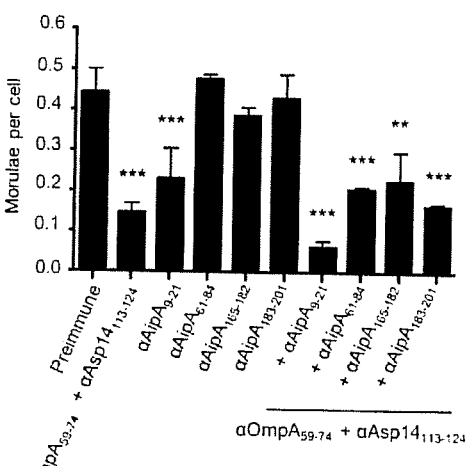
Figure 18C:
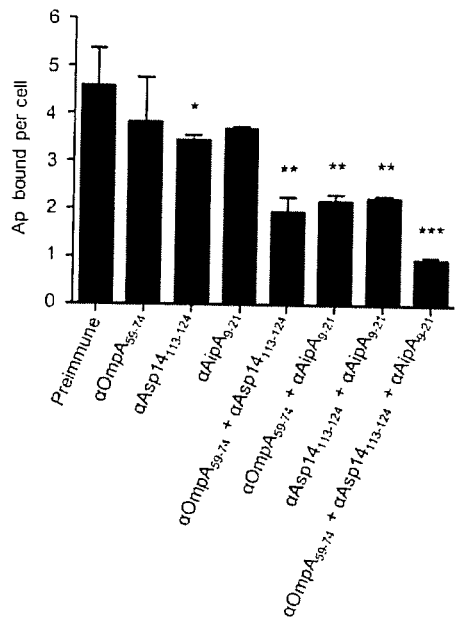

FIG. 18A-C. A combination of antisera targeting the binding domains of OmpA, Asp14, and AipA blocks *A. phagocytophilum* infection of mammalian host cells. DC organisms were incubated with preimmune serum or antibodies specific for OmpA59-74 and Asp14113-124; or AipA9-21, AipA61-84, AipA165-182, or AipA183-201, either independently or in combination with OmpA59-74 and Asp14113-124 antibodies. Next, the bacteria were incubated with HL-60 cells. The infection was allowed to proceed for 24 h, after which the host cells were fixed and examined using immunofluorescence microscopy to determine the percentages of infected cells (A) and the number of morulae per cell (B). (C) To verify that the observed reductions in *A. phagocytophilum* infection were due to antisera mediated blocking of bacterial binding to HL-60 cell surfaces, the experiment was repeated except that DC organisms were incubated with antibodies targeting OmpA59-74 and/or Asp14113-124, and/or AipA9-21 prior to being incubated with host cells, and the numbers of bound bacteria per cell was assessed. Results presented are relative to host cells that had been incubated with bacteria treated with preimmune serum and are the means±SD for six combined experiments. Statistically significant (* $P<0.05$;  $P<0.005$; *$P<0.001$) values are indicated.

DETAILED DESCRIPTION

The detailed characterization of the AipA protein presented herein has led to the confirmation that it is an outer membrane protein and the discovery that it is in fact an invasin protein which is instrumental in host cell invasion by *A. phagocytophilum* bacterium. Further, the present disclosure establishes that AipA, and suitable fragments thereof which represent domains involved in bacterial invasion, can be used as both therapeutic agents (e.g. immunogenic agents and vaccinogens to prevent or treat infection); as diagnostic agents (e.g. as targets to detect antibodies to *A. phagocytophilum* in biological samples); and/or to generate antibodies which are used as therapeutic agents or as diagnostic agents to detect *A. phagocytophilum* AipA protein in biological samples. In some aspects, AipA and/or suitable effective fragments thereof are used for these purposes in combination with one or more other invasin proteins or suitable effective invasin fragments thereof, examples of which include OmpA and Asp14. Homologs of OmpA and Asp 14 may also be employed for these purposes.

The critical regions of OmpA and Asp14 that mediate infection are highly conserved among family members Aph, *A. marginale*, and closely related *Ehrlichia* species, such as *E. chaffeensis*, *E. canis*, and *E. ruminatium*, and may be highly conserved in *A. platys*. In particular, Aph and *A. marginale* are closely related and express many gene homologs, including Asp14 and OmpA and other surface antigens. The high degree of conservation makes these surface proteins ideal for producing a vaccine or immunogenic composition to provide protection from or therapy for multiple pathogens in humans and animals. AipA, however, has no known homologs in other *Anaplasma* and *Ehrlichia* species (all of which cause disease in humans and/or animals—cattle, horses, sheep, dogs, cats) or other non-Anaplasmataceae organisms. Thus, AipA is unique to *A. phagocytophilum* and is thus not employed alone to treat or diagnose infections other than *A. phagocytophilum*.

Accordingly, assays and methods of using the assays to distinguish exposure to or infection with *A. phagocytophilum* from exposure to or infection with a non-*A. phagocytophilum* Anaplasmataseae species are provided, e.g. to permit specialized treatment and/or to track the occurrence or frequency of *A. phagocytophilum* infections. A biological sample from a subject is thus screened with two or more of the agents described herein, at least one or which is AipA based or derived, and if a sample contains (is positive for the presence of) AipA proteins or antibodies to AipA proteins, it is concluded that the subject is infected with (or at least was previously exposed to) *A. phagocytophilum*. Previous exposure to *A. phagocytophilum* may result from a prior vaccination. Therefore, the methods of the invention may be used to determine if a subject has or has not been previously vaccinated. However, if the sample contains only OmpA and/or Asp14 proteins or antibodies, but AipA proteins/antibodies are absent, a conclusion is drawn that the subject is infected or has been exposed to an Anaplasmataseae species that is not *A. phagocytophilum*. If the subject is currently infected with *A. phagocytophilum*, then treatment specific for that organism may be undertaken, e.g. administration of an anti-*A. phagocytophilum* immune response eliciting composition (e.g. compositions comprising AipA protein or fragments thereof as described herein), administration of antibodies directed specifically to AipA protein or fragments thereof, etc.

In order to facilitate the understanding of the present invention, the following definitions are provided:
Aph: *Anaplasma phagocytophilum* or *A. phagocytophilum*, an Anaplasmataseae family bacterium that is tick-born and causes anaplasmosis in humans and animals.
Apl: *Anaplasma platys* or *A. platys*, an Anaplasmataseae family member bacterium that is tick-born and causes anaplasmosis that is restricted to dogs.
Anaplasmataceae: a family of closely related bacteria, including *Anaplasma* and *Ehrlichia* species. The genera *Neorickettsia* and Wolbachhia are also Anaplasmataceae, bacteria but do not cause anaplasmosis.
Antigen: term used historically to designate an entity that is bound by an antibody, and also to designate the entity that induces the production of the antibody. More current usage limits the meaning of antigen to that entity bound by an antibody, while the word "immunogen" is used for the entity that induces antibody production. Where an entity discussed herein is both immunogenic and antigenic, reference to it as either an immunogen or antigen will typically be made according to its intended utility. The terms "antigen", "antigenic region" "immunogen" and "epitope" may be used interchangeably herein. As used herein, an antigen, immunogen or epitope is generally a portion of a protein (e.g. a peptide or polypeptide).

AipA: 36.9-kilodalton Aph surface protein. AipA has no known homologs in other *Anaplasma* and *Ehrlichia* species or other non-Anaplasmataceae organisms.

Asp14: 14-kilodalton Aph surface protein. Asp 14 homologs are expressed by Anaplasmataceae family members, including Aph, *A. marginale, Ehrlichia chaffeensis, E. canis, E. ewingii*, and *E. ruminatium*.

OmpA: Outer membrane protein A. OmpA homologs are expressed by Anaplasmataceae family members, including Aph, *A. marginale, Ehrlichia chaffeensis, E. canis, E. ewingii*, and *E. ruminatium*.

DC and RC: Aph undergoes a biphasic developmental cycle, the kinetics of which have been tracked in promyelocytic HL-60 cells. The cycle begins with attachment and entry of an infectious dense-cored (DC) organism. Once intracellular, the DC differentiates to the non-infectious reticulate cell (RC) form and replicates by binary fission to produce a bacteria-filled organelle called a morula. Later, the RCs transition back to DCs, which initiate the next round of infection.

Epitope: a specific chemical domain on an antigen that is recognized by a B-cell receptor, and which can be bound by secreted antibody. The term as used herein is interchangeable with "antigenic determinant". An epitope may comprise a single, non-interrupted, contiguous chain of amino acids joined together by peptide bonds to form a peptide or polypeptide. Such an epitope can be described by its primary structure, i.e. the linear sequence of amino acids in the peptide chain. Epitope may also refer to conformational epitopes, which are comprised of at least some amino acids that are not part of an uninterrupted, linear sequence of amino acids, but which are brought into proximity to other residues in the epitope by secondary, tertiary and/or quaternary interactions of the protein. Residues in conformational epitopes may be located far from other residues in the epitope with respect to primary sequence, but may be spatially located near other residues in the conformational epitope due to protein folding.

Immunodominant epitope: The epitope on a molecule that induces the dominant, or most intense, immune response. The immunodominant epitope would elicit the greatest antibody titer during infection or immunization, as measured by, for example, the fraction of reactivity attributable to a certain antigen or epitope in an enzyme-linked immunosorbant assay as compared with the total responsiveness to an antigen set or entire protein.

Invasin domain: An invasin domain is a region of a pathogen's protein that binds a host cell and mediates intracellular signaling and pathogen entry into the host cell. In some cases, uptake of the pathogen results in the formation of a vacuole in which the intracellular pathogen will reside. The invasin domains of the invention are linear amino acid sequences within Asp14, OmpA, AipA or other surface proteins that are found on the outer membrane of the bacteria Aph and other Anaplasmataceae family members, and can vary slightly from one family member to the next. However, the invasin domain in each Asp14 homolog is critical for uptake of bacteria into host cells (known to be neutrophils and endothelial cells in the case of Anaplasmataceae). Invasin domains may be referred to herein as "effector domains".

Inclusive: with respect to linear amino acid sequence, inclusive refers to a sequence that includes the first- and last-numbered amino acids, e.g. "amino acids 1-87 inclusive" refers to a linear amino acid sequence that includes amino acids 1, 2, 3 . . . etc. up to and including amino acids . . . 85, 86 and 87 of a sequence, e.g. a sequence specified as a SEQ ID NO: or in referenced to a SEQ ID NO:.

Linker sequences: short peptide sequences encoding functional units that may be engineered or otherwise added at the ends or within recombinant proteins, polypeptides, peptides of interest. Linker sequences may be used as "handles" for protein purification, as detectable signals of expression or binding to other proteins or macromolecules, to modulate tertiary structure, or enhance antigenicity. Examples of linker sequences include, but are not limited to, an amino acid spacer, an amino acid linker, a signal sequence, a stop transfer sequence, a transmembrane domain, and a protein purification ligand.

LINKER: a program to generate linker sequences for fusion proteins. Protein Engineering 13(5): 309-312, which is a reference that describes unstructured linkers. Structured (e.g. helical) sequence linkers may also be designed using, for example, existing sequences that are known to have that secondary structure, or using basic known biochemical principles to design the linkers. Tags: Recombinant protein sequences that can be added to the N- or C-terminus of a recombinant protein for the purpose of identification or for purifying the recombinant protein for subsequent uses. Examples of recombinant protein tags that may be useful in practicing the invention include, but are not limited to, glutathione-S-transferease (GST), poly-histidine, maltose binding protein (MBP), FLAG, V5, halo, myc, hemaglutinin (HA), S-tag, calmodulin, tag, streptavidin binding protein (SBP), Softag1™, Softag3™, Xpress tag, isopeptag, Spy Tag, biotin carboxyl carrier protein (BCCP), GFP, Nus-tag, strep-tag, thioredoxin tag, TC tag, and Ty tag. All such tags are well-known to those of ordinary skill in the art of recombinant protein production.

Protein: Generally means a linear sequence of about 100 or more amino acids covalently joined by peptide bonds.

Polypeptide: Generally means a linear sequence of about 55 to about 100 amino acids covalently joined by peptide bonds.

Peptide: Generally means a linear sequence of about 55 or fewer amino acids covalently joined by peptide bonds.

Note: The terms "peptide", "polypeptide" and "protein" may be used interchangeably herein.

Chimeric or fusion peptide or polypeptide: a recombinant or synthetic peptide or polypeptide whose primary sequence comprises two or more linear amino acid sequences which do not both occur in a single molecule in nature, or at least are not linearly contiguous in a single molecule in nature. (For example, they may both be present in a single molecule which comprises e.g. amino acids 1-15, but in the fusion or chimera, "amino acids 1-5" and amino acids 10-15" are present but amino acids 6-9 are not present between the sequence represented by amino acids 1-5 and the sequence represented by amino acids 10-15.) The two or more sequences may be, for example, a peptide (e.g. an epitope or antigenic region) and a linker sequence, or two or more peptides (which may be the same or different) which are either contiguous or separated by a linker sequence, etc.

Tandem repeats: two or more copies of nucleic acid or amino acid sequences encoding the same peptide, which are arranged in a linear molecule and are either contiguous or separated by a linker sequence, etc.

Original or native or wild type sequence: The sequence of a peptide, polypeptide, protein or nucleic acid as found in nature.

Recombinant peptide, polypeptide, protein or nucleic acid: peptide, polypeptide, protein or nucleic acid that has been produced and/or manipulated using molecular biology techniques such as cloning, polymerase chain reaction (PCR), etc.

Synthetic peptide, polypeptide, protein or nucleic acid: peptide, polypeptide, protein or nucleic acid that has been produced using chemical synthesis procedures.

Type-specific: associated primarily with a single phyletic group.

Surface protein: A protein located on the outer surface membrane of a cell or bacterium.

Tables 1, 2 and 3 provide a list of the SEQ ID NOS: for sequences described herein.

TABLE 1

Aph Sequence Listing with SEQ ID Numbers for Asp14, OmpA and AipA.

| SEQ ID NO | PROTEIN NAME | GENBANK ACCESSION # AND NAME | AMINO ACID SEQUENCE |
|---|---|---|---|
| SEQ ID NO: 01 | Full-length Asp14 | YP_504865 APH_0248 | MIPLAPWKSISVVYMSGSDEYKEIIKQ CIGSVKEVFGEGRFDDVVASIMKMQE KVLASSMQQDDTGTVGQIESGEGSGA RLSDEQVQQLMNSIREEFKDDLRAIKR RILKLERAVYGANTPKES |
| SEQ ID NO: 02 | Asp14 aa101-124 | APH_0248 | LRAIKRRILKLERAVYGANTPKES |
| SEQ ID NO: 03 | Asp 14 aa113-124 | APH_0248 | RAVYGANTPKES |
| SEQ ID NO: 04 | Full length OmpA | YP_504946 APH_0338 | MLRRSSFFCLLALLSVTSCGTLLPDSN VGVGRHDLGSHRSVAFAKKVEKVYF DIGKYDLKGPGKKVILELVEQLRQDD SMYLVVIGHADATGTEEYSLALGEKR ANAVKQFIIGCDKSLAPRVTTQSRGK AEPEVLVYSTDAQEVEKANAQNRRA VIVVEFAHIPRSGVADMHAPVASSITS ENSNASAEGEDMEASEFSSAIAN |
| SEQ ID NO: 05 | OmpA aa19-74 | APH_0338 | CGTLLPDSNVGVGRHDLGSHRSVAFA KKVEKVYFDIGKYDLKGPGKKVILEL VEQLR |
| SEQ ID NO: 06 | OmpA aa59-74 | APH_0338 | LKGPGKKVILELVEQL |
| SEQ ID NO: 07 | OmpA aa48-56 | APH_0338 | EKVYFDIGK |
| SEQ ID NO: 08 | OmpA | APH_0338 | GHADATGTEEYSLALG |
| SEQ ID NO: 09 | OmpA | APH_0338 | LVYSTDAQEVEKANAQNRRAV |
| SEQ ID NO: 10 | OmpA | APH_0338 | PDSNVGVGRHDLGSHRSVAFAKKVE KVYFDIGKYDLKGPGKKVILELVEQL RQDDSMYLVVIGHADATGTEEYSLAL GEKRANAVKQFIIGCDKSLAPRVTTQS RGKAEPEVLVYSTDAQEVEKANAQN RRAVIVVEFAHIPRSGVADM |
| SEQ ID NO: 11 | Asp14 aa101-112 | APH_0248 | LRAIKRRILKLE |
| SEQ ID NO: 12 | Asp14 aa19-60 | APH_0248 | DEYKEIIKQCIGSVKEVFGEGRFDDVV ASIMKMQEKVLASSM |
| SEQ ID NO: 13 | Full length AipA | APH_0915 | MSFTMSKLSLDPTQGSHTAENIACSIF DMVLGVKSTAKLLAGTWAGTSSTIW KTVTGAASSTKEASSKSYGTLRSSLGS SASRRMLGTCATAALCLTAPLLGAAA AGAAITCALITICMALLFLVLYTVLHI ASQMLRCASLLLSMVCNILHSTFTAT KSCLGGKSPARTTEERVAGDLDHKGV DSDRKHDAEKTEEKKHGLGSLCKSLA INLVSLMGTALVTTPIILLAVVLLVLVP VYLLCATVHHIYQGNYEDRNNDKGSS RGGGTTYYPMTMSASASEESLSSIISE GGLSKTSLPSYSAATATGTGNATGEV FSHSHSSGKSSSKPESRPESNLQNVVA ETMSQQQRSVS |
| SEQ ID NO: 14 | AipA aa9-21 | APH_0915 | SLDPTQGSHTAEN |
| SEQ ID NO: 15 | AipA aa1-87 | APH_0915 | MSFTMSKLSLDPTQGSHTAENIACSIF DMVLGVKSTAKLLAGTWAGTSSTIW KTVTGAASSTKEASSKSYGTLRSSLGS SASRRMLG |

TABLE 2

| | Asp14 Homologs: Sequence Listing with SEQ ID Numbers | | |
|---|---|---|---|
| SEQ ID NO: 16 | *Anaplasma marginale* | AM936 | MSGEDEYKEIIRQCIGSVKEVFGEGRFD DVVASIMKMQEKVLASSMKDGDPVG QIAADGVGNELYDRIADRLEERVSQKI SEDLRIIKKRLLRLERVVLGGGSVSGD AAAHQVSGNQPSQQNSSAAAEGG |
| SEQ ID NO: 17 | *A. marginale* | AM936 | LGGGSVSGDAAAHQVSGNQPSQQNSS AAAEGG |
| SEQ ID NO: 18 | *A. marginale* subspecies Centrale | ACIS_00403 | MSGEDEYKEIIRQCIGSVKEVFGEGRFD DVVASIMKMQEKVLASSMKDGDPVG QIAADGVGNELYDRIADRLEERVSQKI SEDLRIIKKRLLRLERVVLGGGSVSGD AAAAHQVSGNQPSQQNSSAAAEGG |
| SEQ ID NO: 19 | *A. marginale* subspecies Centrale | ACIS_00403 | LGGGSVSGDAAAAHQVSGNQPSQQNS SAAAEGG |
| SEQ ID NO: 20 | *A. marginale* & *A. marginale* subspecies Centrale | AM936 & ACIS-00403 | MSGEDEYKEIIRQCIGSVKEVFGEGRFD DVVASIMKMQEKVLASSM |
| SEQ ID NO: 21 | *A. marginale* & *A. marginale* subspecies Centrale | AM936 & ACIS-00403 | DLRIIKKRLLRLERVV |
| SEQ ID NO: 22 | *Ehrlichia chaffeensis* | ECH_0377 | MAEDDYKGVIKQYIDTVKEIVGDSKTF DQMFESVVRIQERVMAANAQNNEDG VIDNGDQVKRIGSSTSESISNTEYKELM EELKVIKKRILRLERKILKPKEEV |
| SEQ ID NO: 23 | *E. chaffeensis* | ECH_0377 | MAEDDYKGVIKQYIDTVKEIVGDSKTF DQMFESVVRIQERVM |
| SEQ ID NO: 24 | *E. chaffeensis* | ECH_0377 | ELKVIKKRILRLE |
| SEQ ID NO: 25 | *E. chaffeensis* | ECH_0377 | RKILKPKEEV |
| SEQ ID NO: 26 | *E. canis* | Ecaj_0636 | MADDEYKGVIQQYINTVKEIVSDSKTF DQMFESVVKIQERVMEANAQNDDGSQ VKRIGSSTSDSISDSQYKELIEELKVIKK RLLRLEHKVLKPKEGA |
| SEQ ID NO: 27 | *E. canis* | Ecaj_0636 | MADDEYKGVIQQYINTVKEIVSDSKTF DQMFESVVKIQERVM |
| SEQ ID NO: 28 | *E. canis* | Ecaj_0636 | ELKVIKKRLLRLE |
| SEQ ID NO: 29 | *E. canis* | Ecaj_0636 | HKVLKPKEGA |
| SEQ ID NO: 30 | *E. ruminantium* | Erum6320 | MADEDYKGVIKQYIDTVKEIVGDSKTF DQMFESVVKIQERVMAASAQNEANGA LVEGDSKMKRIRSADDSIAYTQSQELL EELKVLKKRIARLERHVFKSNKTEA |
| SEQ ID NO: 31 | *E. ruminantium* | Erum6320 | MADEDYKGVIKQYIDTVKEIVGDSKTF DQMFESVVKIQERVM |
| SEQ ID NO: 32 | *E. ruminantium* | Erum6320 | ELKVLKKRIARLE |
| SEQ ID NO: 33 | *E. ruminantium* | Erum6320 | RHVFKSNKTEA |

TABLE 3

| | | OmpA Homologs: Sequence Listing with SEQ ID Numbers | |
|---|---|---|---|
| SEQ ID NO: 34 | Anaplasma marginale | AM854 | MLHRWLALCFLASFAVTGCGLFSKEKV GMDIVGVPFSAGRVEKVYFDFNKYEIKG SGKKVLLGLVERMKADKRSTLLIIGHTD SRGTEEYNLALGERRANAVKEFILGCDR SLSPRISTQSRGKAEPEVINYSSDFKEAE KAHAQNRRVVLIVECQHSVSPKKKMAI KWPFSFGRSAAKQDDVGSSEVSDENPV DDSSEGIASEEAAPEEGVVSEEAAEEAPE VAQDSSAGVVAPE |
| SEQ ID NO: 35 | A. marginale | AM854 | LFSKEKVGMDIVGVPFSAGRVEKVYFDF NKYEIKGSGKKVLLGLVERMKADKRST LLII |
| SEQ ID NO: 36 | A. marginale subspecies Centrale | ACIS_00486 | MLHRWLALCLLASLAVTGCELFNKEKV NIDIGGVPLSAGRVEKVYFDFNKYEIKGS GKKVLLGLVERMKADKMSTLLIVGHTD SRGTEEYNLALGERRANAVKEFILGCDR SLSPRISTQSRGKAEPEILATYSSDFKEAEK AHAQNRRVVLIMECQHAASPKKARVSR WPFSFGRSSATQQDNGGGTVAAGSPGE DAPAEVVEPEETQEAGE |
| SEQ ID NO: 37 | A. marginale subspecies Centrale | ACIS_00486 | LFNKEKVNIDIGGVPLSAGRVEKVYFDF NKYEIKGSGKKVLLGLVERMKADKMST LLIV |
| SEQ ID NO: 38 | A. marginale & A. marginale subspecies Centrale | AM854 & ACIS-00486 | AGRVEKVYFDFNKYEIKGSGKKVLLGL VERMKAD |
| SEQ ID NO: 39 | A. marginale & A. marginale subspecies Centrale | AM936 & ACIS-00403 | GHTDSRGTEEYNLALG |
| SEQ ID NO: 40 | A. marginale & A. marginale subspecies Centrale | AM854 & ACIS-00486 | RRANAVKEFILGCDRSLSPRISTQSRGKA E |
| SEQ ID NO:41 | A. marginale & A. marginale subspecies Centrale | AM854 & ACIS-00486 | LVYSSDFKEAEKAHAQNRRVVLI |
| SEQ ID NO: 42 | Ehrlichia chaffeensis | ECH_0462 | MKHKLVFIKFMLLCLILSSCKTTDHVPL VNVDHVESNTKTIEKIYFGEGKATIEDSD KTILEKVMQKAEEYPDTNIIIVGHTDTRG TDEYNLELGKQRANAVKDFILERNKSLE DRIIIESKGKSEPAVLVYSNNPEEAEYAH TKNRRVVITLTDNLIYKAKSSDKDPSSN KTEQ |
| SEQ ID NO: 43 | Ehrlichia chaffeensis | ECH_0462 | NVDHVFSNTKTIEKIYFGFGKATIEDSDK TILEKVMQKAEEYPDTNIIIV |
| SEQ ID NO: 44 | Ehrlichia chaffeensis | ECH_0462 | IEDSDKTILEKVMQKAEEYPDTNIIIV |
| SEQ ID NO: 45 | Ehrlichia chaffeensis | ECH_0462 | GHTDTRGTDEYNLELGE |
| SEQ ID NO: 46 | Ehrlichia chaffeensis | ECH_0462 | QRANAVKDFILERNKSLEDRIIIESKGKS EPAV |
| SEQ ID NO: 47 | Ehrlichia chaffeensis | ECH_0462 | LVYSNNPEEAEYAHTKNRRVVI |
| SEQ ID NO: 48 | E. canis | Ecaj_0563 | MKEIKLVFIKFILLCLILSSCKTTDHVPLV NTDHVFSNMKTIEKIYFDFGKATIGDSD KAILEKVIQKAQKDTNTNIVIVGHTDTR GTDEYNLELGEQRANAVKDFIIEHDKSL ENRITVQSKGKSEPAVLVYSSNPEEAEH AHAKNRRVVITLTDNGNKTSQ |

TABLE 3-continued

OmpA Homologs: Sequence Listing with SEQ ID Numbers

| | | | |
|---|---|---|---|
| SEQ ID NO: 49 | E. canis | Ecaj_0563 | TTDHVPLVNTDHVFSNMKTIEKIYFDFG KATIGDSDKAILEKVIQKAQKDTNTNIVI V |
| SEQ ID NO: 50 | E. canis | Ecaj_0563 | GDSDKAILEKVIQKAQKDTNTNIVIV |
| SEQ ID NO: 51 | E. canis | Ecaj_0563 | GHTDTRGTDEYNLELGE |
| SEQ ID NO: 52 | E. canis | Ecaj_0563 | QRANAVKDFIIEHDKSLENRITVQSKGKS EPAV |
| SEQ ID NO: 53 | E. canis | Ecaj_0563 | LVYSSNPEEAEHAHAKNRRVVI |
| SEQ ID NO: 54 | E. ruminantium | Erum5620 | MRYQLIVANLILLCLTLNGCHFNSKHVP LVNVHNLFSNIKAIDKVYFDLDKTVIKD SDKVLLEKLVQKAQEDPTTDIIIVGHTDT RGTDEYNLALGEQRANAVRDFIISCDKS LEKRITVRSKGKSEPAILVYSNNPKEAED AHAKNRRVVITLVNNSTSTDNKVPTTTT PFNEEAHNTISKDQENNTQQQAKSDNIN N1NTQQKLEQDNNNTPEVN |
| SEQ ID NO: 55 | E. ruminantium | Erum5620 | NSKHVPLVNVHNLFSNIKAIDKVYFDLD KTVIKDSDKVLLEKLVQKAQEDPTTDIII V |
| SEQ ID NO: 56 | E. ruminantium | Erum5620 | DSDKVLLEKLVQKAQEDPTTDIIIV |
| SEQ ID NO: 57 | E. ruminantium | Erum5620 | GHTDTRGTDEYNLALGE |
| SEQ ID NO: 58 | E. ruminantium | Erum5620 | QRANAVRDFIISCDKSLEKRITVRSKGKS EPAI |
| SEQ ID NO: 59 | E. ruminantium | Erum5620 | LVYSNNPKEAEDAHAKNRRVVI |

Aph surface proteins AipA, OmpA, and Asp14 have been identified as mediating bacteria-host cell binding and entry. Thus, the surface proteins AipA, OmpA, and Asp14 and fragments thereof that encompass an invasin domain, are used for diagnosing whether a patient has been suffering from Aph infection. Specifically, in one aspect, if antibodies to AipA are present in a suitable biological sample from a subject, then it can be concluded that the subject has been exposed to and/or is infected with Aph. In other aspects, if antibodies to AipA and one or both of OmpA and Asp14 are identified in a suitable biological sample from a subject, then it can be concluded that the subject has been exposed to and/or is infected with Aph. In some aspects, such determinations are made, e.g. by testing serum or other biological material from a subject suspected of an Aph infection by a suitable assay, such as an ELISA or immunoblot using, for example, antibodies to (e.g. specific antibodies to AipA (and optionally, to OmpA, and Asp14). Further, antibodies can also be raised against two or more of AipA, OmpA and Asp14, or to invasin domains from two or more of AipA, OmpA and Asp14, e.g. combined in a chimeric protein. If the antibodies bind to or interact with proteins or peptide fragments in the sample, then it can be determined that the subject has been exposed to, infected with, and/or is currently infected with Aph. Alternatively, if one or more of the amino acid sequences described herein (e.g. a form of the sequence that is labeled with a detectable label) is exposed to a biological sample, and it is found that there are antibodies in the sample which bind to the one or more amino acid sequences, then it can be concluded that the subject from whom the sample was taken has antibodies to Aph and thus has either been exposed to Aph bacteria and/or is still infected with Aph.

In other aspects, administration of AipA protein or suitable antigenic fragments thereof, or nucleic acids encoding the protein or fragments, is used to elicit an immunogenic response, e.g. a protective immunogenic response, in a subject. The immunogenic response may protect a naive subject from subsequent full-blown Aph infection when exposed to the bacterium (e.g. when bitten by an infected tick). Antibodies elicited by AipA administration bind to invasin proteins of bacteria that enter the bloodstream and prevent host cell invasion and establishment of a productive infection. Alternatively, administration of AipA protein or suitable antigenic fragments thereof, or nucleic acids encoding the protein or fragments, is used to provide treatment for an existing Aph infection by eliciting the production of antibodies to Aph. In some aspects, in addition to administration of AipA, one or both of OmpA and Asp14 proteins or suitable antigenic fragments thereof, or nucleic acids encoding such proteins and fragments, may be administered. For example, all three proteins, or suitable effective fragments thereof as described herein, may be administered.

In some aspects, what is provided herein is a polypeptide or protein comprising at least one "core" sequence or segment consisting of an invasin domain sequence from one or more of AipA, Asp14 and OmpA as described herein. In such constructs, which are generally chimeric or fusion polypeptides or proteins, the core sequence(s) is/are flanked on at least one of the amino terminus and carboxy terminus (i.e. at one or the other or both termini) by a sequence which is not found adjacent to the core sequence in nature. The sequence which is not found adjacent to the core sequence in nature may be a heterologous sequence (e.g. synthetic and/or from another species or strain) or may be a repeat or duplication of the same sequence. In some constructs, one core sequence is present alone; in other constructs, multiple core sequences of a single type (i.e. AipA, Asp14 or OmpA) are present. In yet other constructs, one core sequence from at least two of AipA, Asp14 and OmpA are present. In yet other constructions, multiple copies of one or more core sequence from at least two of AipA, Asp14 and OmpA are present.

It is contemplated that virtually any protein sequence, as well as its corresponding nucleic acid sequence coding for the protein sequence that is or includes SEQ ID NO: 14 may be used as described herein. This includes the full length sequence (e.g., SEQ ID NO:13) as well as any sequence of, for example from about 5-50 (or less than 5 or more than 50) amino acids before the beginning (amino terminus) or at the end (carboxy terminus) of the amino acid sequence of the invasin domain defined by SEQ ID NO:14. Such sequences include one or more amino acids or amino acid sequences which are adjacent to or which flank SEQ ID NO: 14 in nature (such as those which are present in SEQ ID NO:13). The polypeptide sequences as described herein may also be shortened on either the amino or carboxy terminus (or both) by one, two, or more amino acids to produce fragments within the context of the invention wherein the fragments produce the same or a similar protective effect. Alternatively, the polypeptide may be a chimera or fusion protein which comprises flanking amino acids sequences which are not adjacent to the native sequence in nature. For example, the adjacent sequences may be corresponding amino acids which are from different but related species (e.g. other Anaplasmataceae); or amino acids which are from different species (e.g. from other bacteria or eukaryotes of interest, e.g. from infectious agents); or from a synthetic sequence, e.g. various tags such as histidine or glutathione S-transferase (GST) tags, linkers, spacers, targeting sequences, etc. as described elsewhere herein).

Further, a single recombinant polypeptide may comprise one copy, or more than one copy (a plurality, two or more) of each of these different sequences, all of which include SEQ ID NO: 14. A single polypeptide may contain two or more copies of a single sequence, a single copy of one sequence and two or more copies of one or more different sequences, or two or more copies of at least two different sequences. In exemplary embodiments, a polypeptide of the invention includes one or more copies of SEQ ID NO:14 and optionally one or more copies of at least one of SEQ ID NO:03 and SEQ ID NO:06 on a single polypeptide or multiple polypeptides. Another aspect of the disclosure provides a mixture of at least two of any of the peptides and/or polypeptides described herein.

In some embodiments, the composition consists of or comprises three polypeptides with amino acid sequences encoding an AipA, OmpA, or Asp14 invasin domain. The Asp14 invasin domain lies within aa113-124 (SEQ ID NO:03). In other embodiments, polypeptide fragments such as Asp14 aa101-124 (SEQ ID NO:02) or the full length protein (SEQ ID NO:01) are used. In another embodiment, the composition of the invention comprises the invasin domain of OmpA, which lies within aa59-74 (SEQ ID NO:04). In other embodiments, a larger fragment of OmpA encompassing aa19-74 (SEQ ID NO:05), or the full length OmpA protein (SEQ ID NO:06) is used.

There is currently no means for preventing transmission of the bacteria causing anaplasmosis or HGA. While antibiotic treatments exist, these treatments are not advised for some groups of patients. In one embodiment, the invention is a vaccine for prevention or treatment of anaplasmosis and HGA. One embodiment of the invention is a pharmaceutically acceptable composition comprising one or a plurality of any one of or a mixture of at least two amino acid sequences which are or include the amino acid sequences which are identified as SEQ ID NO:01, 02, 03, 04, 05, 06, 13, 14, or 15. Administration of the composition of the invention stimulates an immune response in a subject and production of antibodies against AipA, Asp14, OmpA, or all three. Because AipA, OmpA, and Asp14 are on the outer surface of Aph bacteria, antibodies produced by the subject will block binding of bacteria to host cells and interfere with uptake into vacuoles. Bacteria unable to enter host cells are detected by the host immune system and cleared from the body. Blockade can occur at the point of entry into neutrophils or endothelial cells or transfer between these two host cell types. Interruption of the zoonotic life cycle provides a further benefit to public health and well-being by breaking the chain of disease transmission to others.

Aside from commercial assays to detect Apl in dogs, there is no specific assay to rapidly confirm Anaplasmataceae infection, or accurately diagnose HGA or anaplasmosis. In one embodiment, the invention provides a method to detect the presence of Aph AipA, OmpA, and/or Asp14 in assays of biological samples obtained from subjects to bind to antibodies produced by an Anaplasmataceae-infected individual, either of which would be diagnostic for HGA or anaplasmosis. The preferred composition for diagnostic testing may comprise full length AipA (SEQ ID NO:13), Asp14 (SEQ ID NO: 3), and/or OmpA (SEQ ID NO:06). However, compositions comprising fragments of AipA such as SEQ ID NO:14 or a mixture of at least two of SEQ ID NO:13, 14, and 15 are also contemplated. Likewise, a composition comprising fragments of OmpA, such as SEQ ID NO:04 and/or 05, and any mixtures of at least two of SEQ ID NO:04, 05, and 06 are also contemplated. Fragments of Asp14, such as SEQ ID NO:01 and/or 02, are also contemplated, as are any mixtures of at least two of SEQ ID NO:01, 02, and 03. The assay used to detect antibodies may be any type of immunoassay, such as an immunoblot or an enzyme-linked immunosorbent assay. The test sample may be any type of body fluid, such as blood, plasma, serum, urine, saliva, or other body fluid. Tissues or cells may also be used, such as tissue sections or cell preparations adhered to slides or coverslips for immunohistochemical staining. In an exemplary embodiment, the assay used is an ELISA with each protein type to independently detect antibodies to AipA, Asp14, and OmpA, however, a combination to detect AipA, Asp14, and OmpA antibodies in one ELISA is also contemplated.

In addition to sequences for OmpA, Asp14, and AipA shown in Table 1, and homologs shown in Tables 2-3, other surface proteins that Aph preferentially expresses in human versus tick cells may be used. Table 4 shows examples of proteins that can be included in the "cocktail" of peptides, polypeptides or protein sequences of the composition of the invention. Examples of these include APH_1325 (Msp2), APH_1235, APH_1378, APH_1412, APH_0346, APH_0838, APH_0839, APH_0874, and APH_0906 because all are upregulated 3- to 60-fold during RC-DC transition, DC exit, and/or reinfection and our surface proteomic study indicates that they are surface proteins. The file names for each of the aforementioned proteins are from the *A. phagocytophilum* HZ annotated genome. A similar expression profile is exhibited by APH_1235, which is another late stage gene that is upregulated 70-fold (Troese et al., 2011). Studies by Mastronunzio and colleagues suggest that APH_1235 is an *A. phagocytophilum* surface protein. P44 is a 44 kilodalton surface protein and is the bacterium's major surface protein. Synonyms of P44 are Msp2 (major surface protein 2) and Msp2 (P44). All *Anaplasma* species encode P44 proteins and there are huge repertoires of P44 genes in these bacterial species' chromosomes. For instance, the annotated Aph strain HZ genome encodes 113 P44 proteins. These exist as complete genes or pseudogenes (incomplete genes). There is one expression site for p44 genes. Basically, different p44 genes get shuffled into the expression site by a process known as gene conversion with the end result being that Aph (and other *Anaplasma* species) can vary the P44 protein on their cell surfaces, a process called antigenic variation. This enables them to perpetually evade the humoral immune response.

TABLE 4

Anaplamatacaea Surface Proteins Sequence Listing and SEQ ID Numbers

| SEQ ID NO: 60 | Full-length APH_1378 | Genbank Accession No: YP_505877 |
| --- | --- | --- |
| SEQ ID NO: 61 | Full-length APH_1412 | Genbank Accession No: YP_505903 |
| SEQ ID NO: 62 | Full-length APH_0346 | Genbank Accession No: YP_504953 |
| SEQ ID NO: 63 | Full-length APH_0838 | Genbank Accession No: YP_505415 |
| SEQ ID NO: 64 | Full-length APH_0839 | Genbank Accession No: YP_505416 |
| SEQ ID NO: 65 | Full-length APH_0874 | Genbank Accession No: YP_505450 |
| SEQ ID NO: 66 | Full-length APH_0906 | Genbank Accession No: YP_505479 |
| SEQ ID NO: 67 | Full-length APH_1325 (Msp2) | Genbank Accession No: YP_505833 |
| SEQ ID NO: 68 | Full-length APH_1235 | Genbank Accession No: YP_505764 |

In addition to polypeptides sequences from Aph surface proteins, other sequences may be included in the polypeptides of the invention. Such sequences include but are not limited to antigenic peptide sequences such as linker sequences which in and of themselves are antigenic. Examples of recombinant protein tags that may be useful in practicing the invention include but are not limited to glutathione-S-transferease (GST), poly-histidine, maltose binding protein (MBP), FLAG, V5, halo, myc, hemaglutinin (HA), S-tag, calmodulin, tag, streptavidin binding protein (SBP), Softag1™, Softag3™, Xpress tag, isopeptag, Spy Tag, biotin carboxyl carrier protein (BCCP), GFP, Nus-tag, strep-tag, thioredoxin tag, TC tag, and Ty tag. Examples of linker sequences include but are not limited to an amino acid spacer, an amino acid linker, a signal sequence, a stop transfer sequence, a transmembrane domain, and a protein purification ligand. It should also be recognized that a multitude of other such sequences are known to those of skill in the art, and inclusion of other antigenic, linker, or tag sequences is contemplated.

Those of skill in the art will recognize that, while in some embodiments of the invention, the amino acid sequences that are chosen for inclusion in the polypeptides of the invention correspond exactly to the primary amino acid sequence of the original or native sequences of an AipA, Asp14, or OmpA protein, this need not always be the case. The amino acid sequence of an epitope that is included in the polypeptides of the invention may be altered somewhat and still be suitable for use in the present invention. For example, certain conservative amino acid substitutions may be made without having a deleterious effect on the ability of the polypeptides to elicit an immune response. Those of skill in the art will recognize the nature of such conservative substitutions, for example, substitution of a positively charged amino acid for another positively charged amino acid (e.g. K for R or vice versa); substitution of a negatively charged amino acid for another negatively charged amino acid (e.g. D for E or vice versa); substitution of a hydrophobic amino acid for another hydrophobic amino acid (e.g. substitution of A, V, L, I, W, etc. for one another); etc. All such substitutions or alterations of the sequences of the polypeptides that are disclosed herein are intended to be encompassed by the present invention, so long as the resulting polypeptides still function to elicit a suitable immune response. In addition, the amino acid sequences that are included in the polypeptides or any chimeric proteins of the invention need not encompass a full length native polypeptide. Those of skill in the art will recognize that truncated versions of amino acid sequences that are known to be or to contain antigenic polypeptides may, for a variety of reasons, be preferable for use in the practice of the invention, so long as the criteria set forth for an epitope is fulfilled by the sequence. Amino acid sequences that are so substituted or otherwise altered may be referred to herein as "based on" or "derived from" the original wild type or native sequence. In general, the AipA, Asp14, or OmpA proteins or polypeptide fragments from which the linear epitopes are "derived" or on which the linear epitopes are "based" are the AipA, Asp14, or OmpA proteins or peptide fragments as they occur in nature. These natural AipA, Asp14, or OmpA proteins may alternatively be referred to as native or wild type proteins.

Such changes to the primary sequence may be introduced for any of a variety of reasons, for example, to eliminate or introduce a protease cleavage site, to increase or decrease solubility, to promote or discourage intra- or inter-molecular interactions such as folding, ionic interactions, salt bridges, etc, which might otherwise interfere with the presentation and accessibility of the individual epitopes along the length of a peptide or polypeptide. All such changes are intended to be encompassed by the present invention, so long as the resulting amino acid sequence functions to elicit a protective antibody response in a host to whom it is administered. In general, such substituted sequences will be at least about 50% identical to the corresponding sequence in the native protein, preferably about 60 to 70, or even 70 to 80, or 80 to 90% identical to the wild type sequence, and preferably at least about 95, 96, 97, 98, 99, or even 100% identical to a native AipA, Asp14, or OmpA sequence or peptide fragment. The reference native AipA, Asp14, or OmpA sequence or peptide fragment may be from any suitable type of Anaplasmataceae, e.g. from any Anaplasmataceae which is known to infect mammals.

In some embodiments of the invention, individual linear epitopes in a chimeric vaccinogen are separated from one another by intervening sequences that are more or less neutral in character, i.e. they do not in and of themselves elicit an immune response to Anaplasmataceae. Such sequences may or may not be present between the epitopes of a chimera. If present, they may, for example, serve to separate the epitopes and contribute to the steric isolation of the epitopes from each other. Alternatively, such sequences may be simply artifacts of recombinant processing procedures, e.g. cloning procedures. Such sequences are typically known as linker or spacer peptides, many examples of which are known to those of skill in the art. See, for example, Crasto, C. J. and J. A. Feng. 2000.

In addition, other elements may be present in chimeric proteins, for example leader sequences or sequences that "tag" the protein to facilitate purification or detection of the protein, examples of which include but are not limited to tags that facilitate detection or purification (e.g. S-tag, Flag-tag, Histidine tags), other antigenic amino acid sequences such as known T-cell epitope containing sequences and protein stabilizing motifs, etc. In addition, the chimeric proteins may be chemically modified, e.g. by amidation, sulfonylation, lipidation, or other techniques that are known to those of skill in the art.

The invention further provides nucleic acid sequences that encode the proteins, protein fragments, polypeptides, peptides and/or chimeric proteins described herein. Such nucleic acids include DNA, cDNA, RNA (e.g. mRNA), and/or hybrids thereof, and the like, both single and double stranded, and complements thereof. Further, the invention comprehends vectors which contain or house one or more of such coding sequences, or sequences complementary to the coding sequences. Examples of suitable vectors include but are not limited to plasmids, cosmids, viral based vectors, expression vectors, etc. In some embodiments, the vector is a plasmid expression vector. In other aspects, the vector is a vector suitable for administration to a mammal such as a human, e.g. an attenuated viral vector such as an adenoviral, retroviral, herpes simplex, or other viral vector which is replication competent. In other aspects, the vector is a host cell harboring the nucleic acid. The encoding sequences are typically configured within the vectors so as to be translatable, e.g. by being operationally connected to a functional promoter sequence or region. The vectors may or may not be capable of replication, but are capable of being translated to produce the encoded polypeptide(s).

Nucleic acids encoding the sequences of interest may also be present in or associated with, for example, lipoplexes, polymersomes, polyplexes, dendrimers, organic and inorganic nanoparticles, etc.

The invention also provides host cells containing the nucleic acids of the invention. The host cell can be any cell that can grow in culture, be transformed or transfected with heterologous nucleotide sequences and can express those sequences. These include bacteria, such as E. coli, Bacillus, yeast and other fungi, plant cells, insect cells, and mammalian cells. In addition, expression of these sequences in higher eukaryotic host cells may be transient or stable.

The chimeric proteins of the invention may be produced by any suitable method, many of which are known to those of skill in the art. For example, they may be chemically synthesized, or produced using recombinant DNA technology (e.g. in bacterial cells, in cell culture (mammalian, yeast or insect cells), in plants or plant cells, or by cell-free prokaryotic or eukaryotic-based expression systems, by other in vitro systems, etc.). In some embodiments, the polypeptides are produced using chemical synthesis methods.

The present invention also provides compositions for use in eliciting an immune response. The compositions comprise one or more peptides, polypeptides, or proteins as described herein, or nucleic acids encoding them (e.g. as the nucleic acid per se, or in a vector such as a host cell comprising the nucleic acid). The compositions may be utilized as immunogenic composition and/or vaccines to prevent or treat anaplasmosis, particularly when manifested in humans as HGA. By eliciting an immune response, it is meant that administration of the antigen causes the synthesis of specific antibodies (at a titer as described above) and/or cellular proliferation, as measured, e.g. by $^3$H thymidine incorporation, or by other known techniques. By "vaccine" we mean a linear polypeptide, a mixture of linear polypeptides or a chimeric or fusion polypeptide that elicits an immune response, which results in protection of an organism against challenge with an Anaplasmataceae species bacterium. The protective response either wholly or partially prevents or arrests the development of symptoms related to anaplasmosis or HGA infection (i.e. the symptoms of anaplasmosis), in comparison to a non-vaccinated (e.g. adjunct alone) control organisms, in which disease progression is not prevented. The compositions include one or more isolated and substantially purified polypeptides or chimeric peptides as described herein, and a pharmacologically suitable carrier. The polypeptides or chimeric peptides in the composition may be the same or different, i.e. the composition may be a "cocktail" of different polypeptides or chimeric peptides, or a composition containing only a single type of polypeptide or chimeric peptide. The preparation of such compositions for use as vaccines is well known to those of skill in the art. Typically, such compositions are prepared either as liquid solutions or suspensions, however solid forms such as tablets, pills, powders and the like are also contemplated. The liquid may be an aqueous liquid. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. The vaccine preparations of the present invention may further comprise an adjuvant, suitable examples of which include but are not limited to Seppic, Quil A, Alhydrogel, etc. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of polypeptides or chimeric peptides in the formulations may vary. However, in general, the amount in the formulations will be from about 0.01-99%, weight/volume.

The methods involve administering a composition comprising proteins, protein fragments (peptides), recombinant polypeptides and/or chimeric peptides described herein, or by administering nucleic acids encoding these proteins, fragments and recombinant polypeptides and chimeric peptides, in a pharmacologically acceptable carrier to a mammal. The nucleic acids may be housed in a vector (e.g. a host cell) as described herein. The mammal may be a human, but this need not always be the case. Because anaplasmosis is a zoonotic disease that causes anaplasmosis in all known mammalian hosts, veterinary applications of this technology are also contemplated. The vaccine preparations of the present invention may be administered by any of the many suitable means which are well known to those of skill in the art, including but not limited to by injection, inhalation, orally, intranasally, by ingestion of a food product containing the polypeptides or chimeric peptides, etc. In some embodiments, the mode of administration is subcutaneous or intramuscular. In addition, the compositions may be administered in conjunction with other treatment modalities such as substances that boost the immune system, various antibacterial chemotherapeutic agents, antibiotics, and the like.

The present invention provides methods to elicit an immune response to Anaplasmataceae and/or to vaccinate against Anaplasmataceae infection in mammals. In one embodiment, the mammal is a human. However, those of skill in the art will recognize that other mammals exist for which such vaccinations would also be desirable, e.g. the preparations may also be used for veterinary purposes. Examples include but are not limited to companion "pets" such as dogs, cats, etc.; food source, work and recreational animals such as cattle, horses, oxen, sheep, pigs, goats, and the like; or wild animals that serve as a reservoir of Anaplasmataceae, particularly wild animals adapted to living in close proximity to urban areas (e.g. mice, deer, rats, raccoons, opossum, coyotes, etc). The compositions of the invention may be used as bait vaccines, such as bait containing any of the vaccine preps described herein (e.g. mouse bait, deer bait, etc.) Also, animals in zoos and reserves may benefit from protection against Anaplasmataceae infection.

The invention also provides a diagnostic and a method for using the diagnostic to identify individuals who have antibodies to the epitopes contained within the polypeptides or chimeric proteins of the invention. A biological sample from an individual (e.g. a human, a deer, or other mammals susceptible to infection by Anaplasmataceae) suspected of having been exposed to Anaplasmataceae, or at risk for being exposed to Anaplasmataceae, is contacted with the peptides, polypeptides, or chimeric proteins of the invention. Using known methodology, the presence or absence of a binding reaction between the polypeptides or chimeric proteins and antibodies in the biological sample is detected. A positive result (i.e. binding occurs, thus antibodies are present) indicates that the individual has been exposed to and has previously mounted an immune response to, and/or is infected with Anaplasmataceae. Further, the diagnostic aspects of the invention are not confined to clinical use or home use, but may also be valuable for use in the laboratory as a research tool, e.g. to identify Anaplasmataceae bacteria isolated from ticks, to investigate the geographical distribution of Anaplasmataceae species and strains, etc.

The present invention also encompasses antibodies to the epitopes and/or to the polypeptides or chimeric proteins disclosed herein. Such antibodies may be polyclonal, monoclonal, or chimeric, and may be generated in any manner known to those of skill in the art. In a preferred embodiment of the invention, the antibodies are bactericidal, i.e. exposure of Anaplasmataceae bacteria to the antibodies causes death of the bacteria. Such antibodies may be used in a variety of ways, e.g. as detection reagents to diagnose prior exposure to Anaplasmataceae, as a reagent in a kit for the investigation of Anaplasmataceae, to treat Anaplasmataceae infections, etc.

Alternatively, appropriate antigen fragments or antigenic sequences or epitopes may be identified by their ability, when included in polypeptides or chimeric proteins, to elicit suitable antibody production to the epitope in a host to which the polypeptides or chimeric proteins are administered. Those of skill in the art will recognize that definitions of antibody titer may vary. Herein, "titer" is taken to be the inverse dilution of antiserum that will bind one half of the available binding sites on an ELISA well coated with 100 ng of test protein. In general, suitable antibody production is characterized by an antibody titer in the range of from about 100 to about 100,000, and preferably in the range of from about 10,000 to about 10,000,000. Alternatively, and particularly in diagnostic assays, the "titer" should be about three times the background level of binding. For example, to be considered "positive", reactivity in a test should be at least three times greater than reactivity detected in serum from uninfected individuals. Preferably, the antibody response is protective, i.e. prevents or lessens the development of symptoms of disease in a vaccinated host that is later exposed to Anaplasmataceae, compared to an unvaccinated host.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

Example 1. *Anaplasma phagocytophilum* Surface Protein AipA Mediates Invasion of Mammalian Host Cells Summary

*Anaplasma phagocytophilum*, which causes granulocytic anaplasmosis in humans and animals, is a tick-transmitted obligate intracellular bacterium that mediates its own uptake into neutrophils and non-phagocytic cells. Invasins of obligate intracellular pathogens are attractive targets for protecting against or curing infection because blocking the internalization step prevents survival of these organisms. The complement of *A. phagocytophilum* invasins is incompletely defined. Here, the significance of a novel *A. phagocytophilum* invasin protein, AipA is reported. *A. phagocytophilum* induced aipA expression during transmission feeding of infected ticks on mice. The bacterium upregulated aipA transcription when it transitioned from its non-infectious reticulate cell morphotype to its infectious dense-cored morphotype during infection of HL-60 cells. AipA localized to the bacterial surface and was expressed during in vivo infection. Of the AipA regions predicted to be surface-exposed, only residues 1 to 87 (AipA$_{1-87}$) were found to be essential for host cell invasion. Recombinant AipA$_{1-87}$ protein bound to and competitively inhibited *A. phagocytophilum* infection of mammalian cells. Antiserum specific for AipA$_{1-87}$, but not other AipA regions, antagonized infection. Additional blocking experiments using peptide-specific antisera narrowed down the AipA invasion domain to residues 9 to 21. An antisera combination targeting AipA$_{1-87}$ together with two other *A. phagocytophilum* invasins, OmpA and Asp14, nearly abolished infection of host cells. This study identifies AipA as an *A. phagocytophilum* surface protein that is critical for infection, demarcates its invasion domain, and establishes a rationale for targeting multiple invasins to protect against granulocytic anaplasmosis.

Introduction

*Anaplasma phagocytophilum* is an obligate intracellular bacterium in the order Rickettsiales and family Anaplasmataceae that infects neutrophils to cause granulocytic anaplasmosis in humans and animals. Though primarily an *Ixodes* spp. tick-borne illness (Truchan et al., 2013), human granulocytic anaplasmosis (HGA) can also be transmitted perinatally, nosocomially, and through blood transfusion (Annen et al., 2012; Carlyon, 2012; Jereb et al., 2012; Alhumaidan et al., 2013). The disease presents as a non-specific febrile illness that can be accompanied by leukopenia, thrombocytopenia, elevated levels of serum transaminases, and increased susceptibility to potentially fatal secondary infections (Truchan et al., 2013). HGA is an emerging infection in the United States, Europe, and Asia (Truchan et al., 2013). The number of reported HGA cases in the United States increased over six-fold from 2003 to 2012, the latest period for which disease reporting statistics are available (Hopkins et al., 2005; Centers for Disease Control and Prevention, 2013).

*A. phagocytophilum* undergoes a biphasic developmental cycle that begins when an infectious dense-cored (DC) organism binds to and enters its host cell, where it resides within a host cell-derived vacuole. Between 4 and 8 h, the DC develops into the non-infectious reticulate cell (RC) morphotype that subsequently divides by binary fission to yield a bacteria-filled vacuolar inclusion. From 8 to 20 h, the intravacuolar population consists exclusively of replicating RCs. Most RCs transition back into DCs between 28 and 32 h. DCs then exit host cells between 28 to 36 h and initiate the next round of infection (Troese et al., 2009). *A. phagocytophilum* OMPs that are upregulated during RC-to-DC transition, bacterial exit, and reinfection are attractive targets to evaluate for both their roles in infection and their prospect as protective antigens.

Given the potential severity of HGA, the limited choices of antibiotics for treating the disease, and the lack of a vaccine, a thorough understanding of *A. phagocytophilum* cellular invasion is critical. OmpA (APH0338) and Asp14 (14-kDa *A. phagocytophilum* surface protein; APH0248) were recently identified as being important for *A. phagocytophilum* entry into mammalian cells (Ojogun et al., 2012; Kahlon et al., 2013). OmpA binds to 2,3-sialic acid of the sialyl Lewis x (sLe$^x$) tetrasaccharide that caps P-selectin glycoprotein ligand-1 (PSGL-1) on myeloid cell surfaces. OmpA also recognizes α2,3-sialic acid residues that decorate glycoproteins on endothelial cells (Ojogun et al, 2012). The Asp14 receptor is unknown. Evidence implicates involvement of one or more *A. phagocytophilum* invasins in addition to OmpA and Asp14 in mediating infection (Kahlon et al., 2013). Identifying these invasins and evaluating if targeting them alone or in concert with OmpA and Asp14 can block bacterial entry will lead to the development of effective prophylaxes against HGA.

A whole genome transcriptional profiling study revealed *A. phagocytophilum* genes that are upregulated during infection of mammalian versus tick cells (Nelson et al., 2008). Several of these encode putative OMPs, one of which is APH0915. In this study, it is shown that APH0915, hereafter referred to as AipA (*A. phagocytophilum* invasion protein A), is important for bacterial entry into mammalian cells and identify its invasion domain. It is further demonstrated that a combination of antisera targeting AipA, OmpA, and Asp14 synergistically blocks infection. These findings not only advance understanding of how *A. phagocytophilum* employs multiple invasins to promote infection, but also results in the development of a multi-target vaccine that protects against granulocytic anaplasmosis.

Materials and Methods

Cultivation of Uninfected and *A. phagocytophilum*-Infected Host Cell Lines

Human promyelocytic HL-60 cells (CCL-240; American Type Culture Collections (ATCC), Manassas, Va.), RF/6A (rhesus monkey choroidal endothelial cells, ATCC CRL-1780), ISE6 cells and *A. phagocytophilum* (NCH-1 strain) infected HL-60, RF/6A, or ISE6 cells were cultured as previously described (Huang et al., 2012). PSGL-1 CHO cells and untransfected CHO cells were maintained as previously described (Troese et al., 2009).

In Silico Analyses of AipA

The AipA sequence was assessed for transmembrane domains using the TMpred and TMHMM algorithms (Hofinann et al., 1993; Krogh et al., 2001), each of which yielded highly similar predictions. Results obtained using TMpred are presented in FIG. 1. Protean, which is part of the Lasergene® software package (version 8.02; DNASTAR®, Madison, Wis.), was used to assess AipA for regions of hydrophobicity and probability of being surface-exposed using the Kyte-Doolittle (Kyte et al., 1982) and Emini (Emini et al. 1985) algorithms, respectively.

Recombinant Protein and Antiserum Production

A PCR amplicon of aipA (aph0915) nucleotides 1 to 261, encoding AipA amino acids 1 to 87, was generated using primers 5'-CACCTTGAGTTTTACAATGTCGAAGT-TATCGC-3' (SEQ ID NO:69; the first four nucleotides correspond to a Gateway entry vector-compatible sequence) and 5'-CTATCCTAGCATCCTTCTAGAAGCGGAAG-3' (SEQ ID NO:70; the first three nucleotides denote an added stop codon). A PCR product corresponding to aipA nucleotides 745 to 1068, encoding AipA amino acids 249 to 355, was generated using primers 5'-CACCATCTAT-CAAGGAAATTACGAAGATCGCAAC-3' (SEQ ID NO:71) and 5'-GAGCAGCATGCTTTA-3' (SEQ ID NO:72). The amplicons were cloned into the pDest-15 vector (Life Technologies, Carlsbad, Calif.) downstream of and in frame with the gene encoding GST as described previously (Ojogun et al., 2012). Expression and purification GST-tagged AipA residues 1 to 87 (GST-AipA$_{1-87}$), 249 to 355 (GST-AipA$_{249-355}$), and GST alone were performed as previously described (Troese et al., 2011). GST-tagged full-length AipA and AipA amino acids 165 to 204 remained insoluble over a wide range of conditions and thus could not be purified. Generation of murine polyclonal antisera against each GST fusion protein was performed as described previously (Troese et al., 2011). Rabbit polyclonal antisera were raised against synthetic keyhole limpet hemocyanin (KLH)-conjugated peptides corresponding to AipA amino acid residues 9 to 21, 61 to 84, 165 to 182, and 185 to 201 (New England Peptide, Gardner, Mass.). Specificity of each AipA peptide antiserum for its target peptides was determined by the enzyme-linked immunosorbent assay using the TMB substrate kit (Thermo Scientific, Waltham, Mass.) according to the manufacturer's instructions.

Differential aipA Expression Studies

HL-60 cells were synchronously infected with A. phagocytophilum DC organisms (Troese et al., 2009). The infection time course was allowed to proceed for 36 h, a time period that enabled the bacteria to complete their biphasic developmental cycle and initiate a second round of infection (Troese et al., 2009). RNA isolated from aliquots taken every 4 hours was subjected to reverse transcriptase-quantitative PCR (RT-qPCR) as described previously (Troese et al., 2011) using AipA specific primers 5'-CCT-CAACTAAAGAAGCGTCATCAAA-3' (SEQ ID NO:73) and 5'-GTACGGTGTACAAAACGAGGAACA-3' (SEQ ID NO:74), which targeted nucleotides 179 to 388. Relative aipA transcript levels were normalized to the transcript levels of the A. phagocytophilum 16s rRNA gene (aph1000) using the $2^{-\Delta\Delta CT}$ method (Livak et al., 2001; Kahlon et al., 2013). To determine if aipA was transcriptionally upregulated in the DC versus RC morphotype, normalized aipA transcript levels were calculated as fold changes in expression relative to expression at 16 h, a time point at which the entire A. phagocytophilum population existed in the RC form (Troese et al., 2009; Mastronunzio et al., 2012). aipA expression during blood meal acquisition by A. phagocytophilum infected nymphs from mice was monitored as described (Mastronunzio et al., 2012) using AipA primers targeting nucleotides 179 to 388. As a control, expression of the A. phagocytophilum groEL gene (aph0240) during tick transmission feeding was monitored using gene-specific primers (Kahlon et al., 2013).

Western Blotting and Confocal Microscopy

Antisera generated in this study and prior studies targeted AipA, APH0032 (Huang et al., 2010b), Asp55 (Ge et al., 2007), and Msp2 (P44) (Troese et al., 2011). Sera from an HGA patient and a dog that had been naturally infected with A. phagocytophilum were previously described (Ojogun et al., 2012). Western blot analyses (Troese et al., 2011) were performed on uninfected or A. phagocytophilum infected host cells or A. phagocytophilum DC organisms that had been subjected to surface trypsinolysis as described previously (Kahlon et al., 2013). A. phagocytophilum infected host cells were analyzed by spinning disk confocal microscopy as described (Huang et al., 2010a; Huang et al., 2012).

AipA antiserum inhibition of A. phagocytophilum infection Inhibition of host cell infection by preincubating DC organisms with heat-inactivated polyclonal antiserum targeting GST-AipA$_{1-87}$, GST-AipA$_{249-355}$, GST-OmpA (Ojogun, 2012), GST-Asp14 (Kahlon et al., 2013), AipA$_{9-21}$, AipA$_{61-84}$, AipA$_{165-182}$, or AipA$_{183-201}$ (2 mg mL-1) was assessed as previously described (Ojogun et al., 2012). Serum against GST alone and preimmune serum served as negative controls. In instances where DC bacteria were incubated with combinations of antisera targeting AipA, Asp14, and/or OmpA, each respective antiserum was at a concentration of 2 mg mL$^{-1}$, and control antiserum was matched accordingly. Following antibody treatment, bacterial adhesion to and infection of HL-60 cells were monitored using spinning disk confocal microscopy (Ojogun et al., 2012).

Binding of GST-AipA to Mammalian Host Cells and Competitive Inhibition of A. phagocytophilum Infection Mammalian host cells cells were incubated with 4 µM GST, GST-AipA$_{1-87}$, or GST-AipA$_{249-355}$ for 1 h at 37° C. Spinning disk confocal microscopy and flow cytometry were used to assess the binding of recombinant proteins to host cells and competitive inhibition of A. phagocytophilum infection as previously described (Ojogun et al., 2012; Kahlon et al., 2013).

Assessment of the Relevance of AipA to A. phagocytophilum Adherence to PSGL-1 CHO Cells To determine if AipA was important for A. phagocytophilum recognition of sLe$^x$-capped PSGL-1, DC organisms were incubated with antiserum targeting AipA$_{1-87}$, AipA$_{249-355}$, OmpA (Ojogun et al., 2012), or preimmune control serum as described above. Next, the treated bacteria were incubated with PSGL-1 CHO cells or untransfected CHO cells for 1 h, followed by two rounds of washing with PBS to remove unbound bacteria, and enumeration of bound organisms using spinning disk confocal microscopy as described (Troese et al., 2009). As positive controls for inhibition of bacterial adherence to sLe$^x$-capped PSGL-1, PSGL-1 CHO cells were incubated with the PSGL-1 N-terminus-specific antibody, KPL-1 (BD Biosciences, San Jose, Calif.), or the sLe$^x$-specific antibody, CSLEX1 (BD Biosciences) for 30 min prior to the addition of bacteria. Mouse IgG and mouse IgM served as isotype controls for KPL-1 and CSLEX1, respectively.

Statistical Analyses

One-way analysis of variance (ANOVA) was performed using the Prism 5.0 software package (Graphpad; San Diego, Calif.) to assess statistical significance as described (Ojogun et al., 2012). Statistical significance was set at $P<0.05$.

Results

Figure 1A:
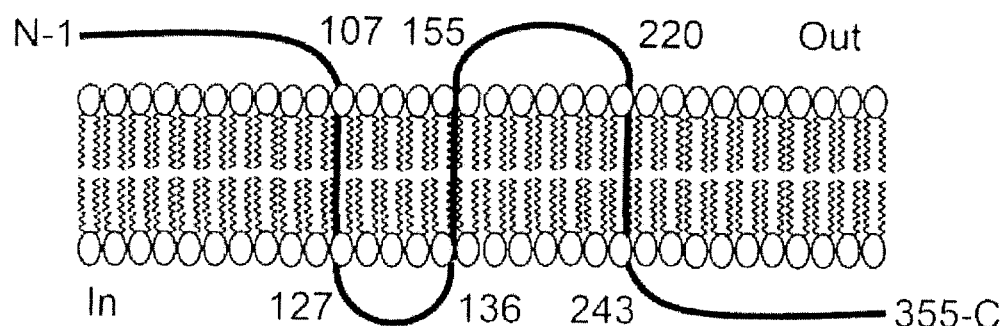
FIGS. 1A-B. Schematic diagrams of *A. phagocytophilum* AipA membrane topology and sequence. (A) Diagram of the predicted topology of AipA in the *A. phagocytophilum* outer membrane. N, AipA amino terminus. C, AipA carboxy terminus. Numerical values indicate amino acid coordinates for predicted transmembrane spanning regions. (B) Diagrams of the AipA sequence. The scale indicates 50-amino acid intervals. For the Hydrophobicity diagram, the Kyte-Doolitle algorithm was used to determine hydrophobic (histogram above the axis) and hydrophilic (histogram below axis) regions. For the Surface diagram, the Emini algorithm was used to determine regions that are likely accessible on the surface of the AipA (histogram above the axis) or not (histogram below the axis). The AipA amino acid segments against which antisera were raised are indicated on the Hydrophobicity plot by horizontal lines.

A. phagocytophilum Differentially Expresses AipA During the Infectious Stage of its Biphasic Developmental Cycle, the Transmission Bloodmeal of Infected Ticks, and Infection of Mammalian Hosts AipA is a 355-amino acid (36.9 kDa) protein and a putative OMP (Nelson et al., 2008). In silico analysis of the AipA amino acid sequence predicted that residues 107 to 127, 136 to 155, and 220 to 243 form transmembrane domains that position residues 1 to 106 and 156 to 219 on the bacterial surface (FIG. 1A). Protein BLAST searches revealed that AipA does not display high sequence identity to sequenced proteins of other organisms, including Anaplasmataceae and Rickettsiales members. Because A. phagocytophilum proteins encoded by genes that are upregulated late during the biphasic developmental cycle are important for infection (Huang et al., 2010b; Troese et al., 2011; Mastronunzio et al., 2012), AipA expression throughout the infection cycle in human promyelocytic HL-60 cells was examined. aipA mRNA levels were approximately 10- to 20-fold higher between 30 and 36 hours—time points that correspond to RC-to-DC transition, exit, and reinfection—than between 4 and 26 hours, time points that correspond to conversion to and replication of non-infectious RC organisms (Troese et al., 2009) (FIG. 2A). Also, the aipA mRNA level of the DC inoculum was comparable to that detected at 36 h, a time point that correlates with reinfection.

Figure 1B:
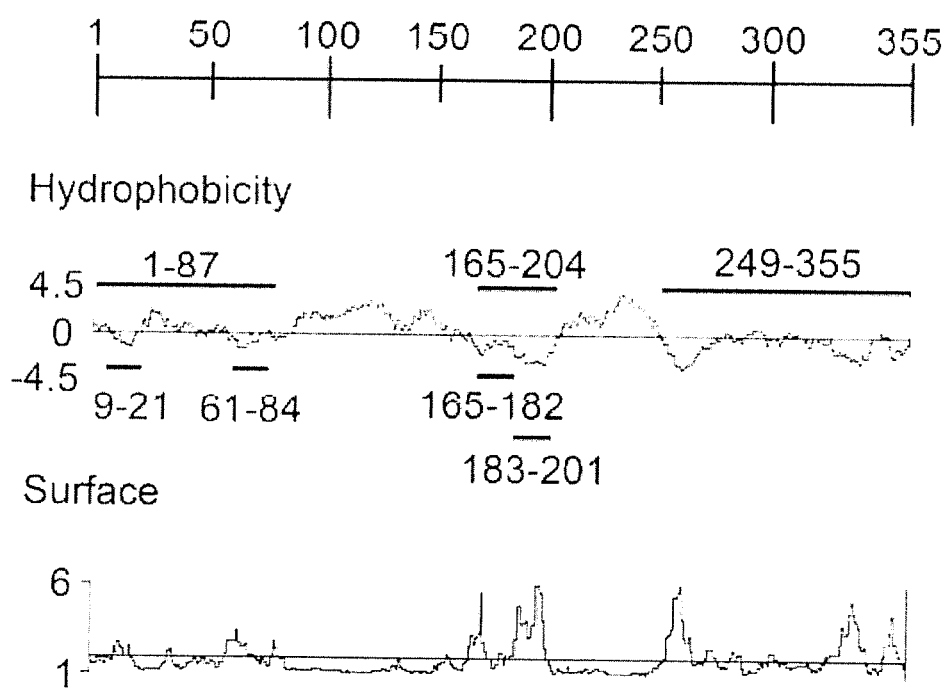

Next, whether or not the differential aipA transcription pattern observed in infected HL-60 cells correlated with differential AipA protein expression was examined. AipA amino acids 1-87 ($AipA_{1-87}$), 165-204 ($AipA_{165-204}$) and 249-355 ($AipA_{249-355}$) contain segments that are hydrophilic and predicted to be accessible on the protein's surface (FIG. 1B). $AipA_{1-87}$ and $AipA_{165-204}$ are predicted to be exposed on the bacterial surface, while $AipA_{249-355}$ is not (FIG. 1B). $AipA_{1-87}$ and $AipA_{249-355}$ were expressed in *Escherichia coli* as proteins N-terminally fused to glutathione-S-transferase. Despite numerous attempts, soluble GST-tagged full-length AipA and $AipA_{165-204}$ could not be expressed (data not shown). Mouse antiserum raised against $AipA_{1-87}$ and $AipA_{249-355}$ fusion proteins recognized a band of the expected size in lysates of *A. phagocytophilum* infected but not uninfected HL-60 cells (FIG. 2B). Anti-$AipA_{249-355}$ recognized an additional band having an apparent mobility that was slightly smaller than 75 kDa, suggesting that AipA may dimerize. Alternatively, anti-$AipA_{249-355}$ may recognize an epitope that is shared with or is similar in sequence to that of the unknown *A. phagocytophilum* protein. An $AipA_{1-87}$ antibody was used to screen infected HL-60 cells by immunofluorescence microscopy. Consistent with the transcriptional data, approximately 70% and 96% of the *A. phagocytophilum* inclusions contained AipA-expressing bacteria at 28 and 32 h, respectively, whereas considerably fewer inclusions were AipA-positive at earlier time points (FIG. 2C). These data demonstrate that AipA is both transcriptionally and translationally upregulated during periods when *A. phagocytophilum* converts to and is in its infectious DC morphotype.

*A. phagocytophilum* genes that are induced during the tick transmission bloodmeal, such as ompA and asp14, encode proteins that are important for establishing infection in mammalian hosts (Ojogun et al., 2012; Kahlon et al., 2013). Therefore, aipA expression in the salivary glands of *A. phagocytophilum* infected *I. scapularis* nymphs was examined over the course of transmission feeding on naïve mice. aipA mRNA was undetectable in unfed infected ticks (FIG. 2D). However, aipA transcripts were significantly induced at 24 h of tick feeding and were increasingly expressed through to 72 h. To ensure that *A. phagocytophilum* transcription was not globally upregulated during tick transmission feeding, groEL (aph0240) expression was also examined. groEL was detected at the highest level in infected unfed nymphs and decreased in expression over the duration of the bloodmeal. Thus, *A. phagocytophilum* specifically induces select genes, including aipA, as it adapts during the transmission bloodmeal to colonize the mammalian host.

Consistent with a prior report that *A. phagocytophilum* preferentially expresses aipA during growth in HL-60 cells versus *L scapularis* embryo-derived ISE6 cells (Nelson et al., 2008), $AipA_{1-87}$ antibody failed to detect a protein of the expected size in lysates of ISE6 cells in which *A. phagocytophilum* had been continually passaged for one, six, or seven weeks (FIG. 2E). APH0032, which is an *A. phagocytophilum* protein that was previously demonstrated to be expressed during infection of ISE6 cells (Huang et al., 2010b), was detected in all infected samples. HGA patient serum and serum from a dog that had been naturally infected with *A. phagocytophilum* each detected GST-$AipA_{1-87}$ (FIG. 2F), confirming that AipA is expressed and elicits a humoral immune response during *A. phagocytophilum* infection of humans and dogs. Two additional HGA patient sera recognized GST-$AipA_{1-87}$ (data not shown).

AipA is an *A. phagocytophilum* Surface Protein

Figure 3A:
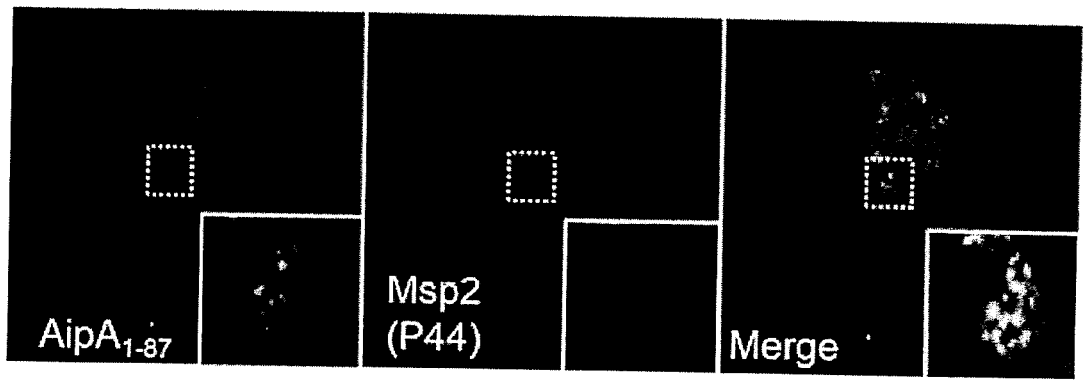
FIG. 3A-B. AipA is an *A. phagocytophilum* OMP. (A) AipA colocalizes with the confirmed OMP, Msp2 (P44). *A. phagocytophilum*-infected RF/6A cells were fixed and viewed by confocal microscopy to assess immunoreactivity with AipA antiserum in conjunction with Msp2 (P44) antiserum. Host cell nuclei were stained with DAPI (4',6'-diamidino-2-phenylindole). The insets demarcated by solid boxes in the lower right corners of each panel are magnified versions of the representative *A. phagocytophilum*-occupied vacuole that is denoted by the hatched box in each panel. (B) AipA is exposed on the bacterial surface. Intact *A. phagocytophilum* DC organisms were incubated with trypsin or vehicle control, solubilized, and Western-blotted. Immunoblots were screened with antiserum targeting AipA$_{1-87}$, Asp55, or APH0032. Data are representative of two experiments with similar results.
Figure 3B:
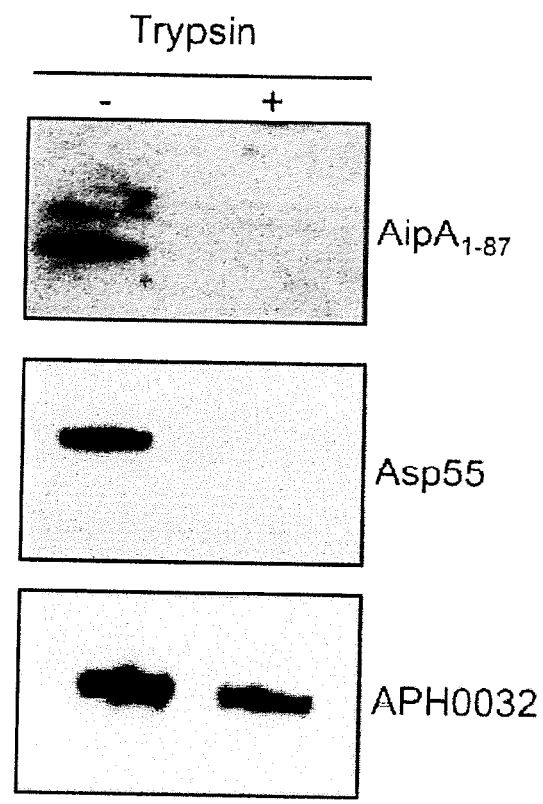
Figure 4A:
FIG. 4A-F. GST-AipA requires amino acids 1 to 87 to bind and competitively inhibit *A. phagocytophilum* infection of mammalian host cells. (A and B) GST-AipA$_{1-87}$ binds to mammalian host cells. RF/6A cells were incubated with GST-AipA$_{1-87}$, GST-AipA$_{249-355}$, or GST alone. (A) The host cells were fixed, screened with GST antibody, and examined using confocal microscopy. Host cell nuclei were stained with DAPI. Representative merged fluorescent images from three experiments with similar results are shown. (B) Flow cytometric analysis of GST fusion protein binding to RF/6A cells. (C to F) GST-AipA$_{1-87}$ competitively inhibits *A. phagocytophilum* infection. HL-60 (C and D) and RF/6A cells (E and F) were incubated with DC bacteria in the presence of GST, GST-AipA$_{1-87}$, or GST-AipA$_{249-355}$ for 1 h. Following removal of unbound bacteria, host cells were incubated for 24 h (C and D) or 48 h (E and F) and subsequently examined using confocal microscopy to assess the percentage of infected cells (C and E) or the mean number (±SD) of pathogen-occupied vacuoles per cell (D and F). Results shown are relative to GST-treated host cells and are the means±SD for three experiments. Statistically significant (*, P<0.05; , P<0.005; *, P<0.001) values are indicated.
Figure 4B:
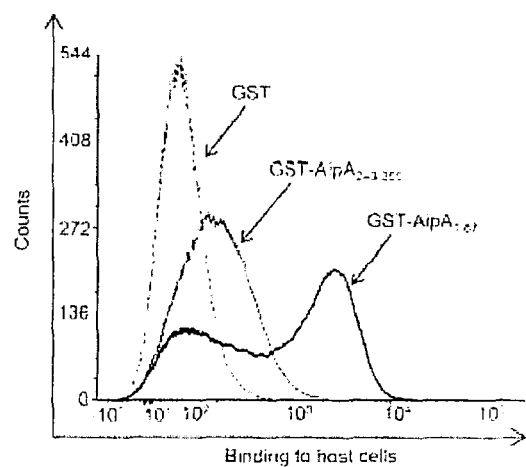
Figures 4C, 4D:
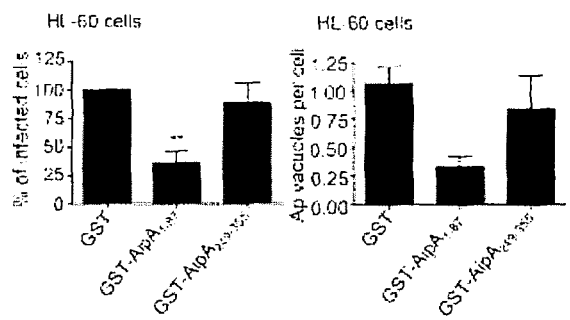
Figures 4E, 4F:
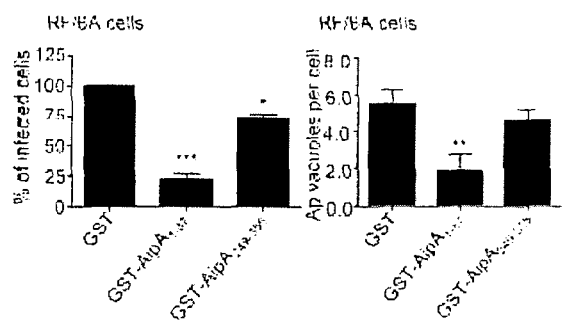

To confirm whether AipA localizes to the bacterial outer membrane, confocal microscopy was used to screen infected RF/6A endothelial cells with $AipA_{1-87}$ antibody in conjunction with antiserum targeting the *A. phagocytophilum* major surface protein, Msp2 (P44) (Carlyon, 2012). Both antibodies detected intravacuolar organisms, yielding the ring-like staining pattern on their peripheries that is characteristic for Msp2 (P44) and other confirmed *A. phagocytophilum* OMPs (Ge et al., 2007; Ojogun et al., 2012; Kahlon et al., 2013) (FIG. 3A). Msp2 (P44) signal colocalized with and extended beyond the AipA signal. Next, to determine if immunoaccessible AipA domains are exposed on the bacterial surface, the surfaces of intact, host cell-free DC bacteria were treated with trypsin, an approach that has been used to confirm surface localization of *A. phagocytophilum* and *Chlamydia trachomatis* OMPs (Wang et al., 2006; Ojogun et al., 2012; Kahlon et al., 2013). AipA residues 1 to 87 include six lysine and three arginine residues, making this putative surface exposed region susceptible to tryptic digest. If $AipA_{1-87}$ or portions thereof were exposed on the *A. phagocytophilum* surface, then incubating intact bacteria with trypsin should result in proteolytic cleavage of this region of the protein, which, in turn, would result in an inability to detect AipA. Trypsin-treated DC organisms were solubilized, Western-blotted, and probed with antiserum specific for $AipA_{1-87}$ or a confirmed surface-exposed epitope of Asp55 (55-kDa *A. phagocytophilum* surface protein) (Ge et al., 2007). Blots were also probed with antiserum targeting APH0032, which does not localize to the *A. phagocytophilum* outer membrane (Huang et al., 2010b). After surface trypsinolysis, APH0032 was detected but AipA and Asp55 were not (FIG. 3B). Thus, AipA residues 1 to 87 are exposed on the *A. phagocytophilum* surface.

GST-AipA Requires Amino Acids 1 to 87 to Bind and Competitively Inhibit *A. phagocytophilum* Infection of Mammalian Host Cells Since AipA is an exposed surface protein that is induced during key infection stages in the *A. phagocytophilum* life cycle, its ability to facilitate interactions with mammalian host cell surfaces to promote infection was investigated. It was assessed if GST-tagged $AipA_{1-87}$ and $AipA_{249-355}$ bind to RF/6A cells. GST alone served as a negative control. GST antibody detected GST-$AipA_{1-87}$ that had adhered to the host cells by both immunofluorescence microscopy and flow cytometry (FIGS. 4, A and B). GST-$AipA_{249-355}$ bound poorly, at best, and GST alone did not bind to host cells. Based on their differential adhesion capabilities, it was rationalized that GST-$AipA_{1-87}$ but not GST-$AipA_{249-355}$ would be able to serve as a competitive agonist to inhibit *A. phagocytophilum* infection. Indeed, preincubating HL-60 and RF/6A cells with GST-$AipA_{1-87}$ significantly reduced the percentages of infected cells and the number of bacterial inclusions per cell by nearly four-fold relative to incubation with GST alone (FIG. 4, C to F). In contrast, GST-$AipA_{249-355}$ did not inhibit *A. phagocytophilum* infection of HL-60 cells and reduced infection of RF/6A cells by only a small degree. These data suggest that AipA residues 1 to 87 contain a domain that contributes to *A. phagocytophilum* invasion of myeloid and endothelial cells.

Antiserum Targeting AipA Residues 1 to 87 Inhibits *A. phagocytophilum* Infection of Host Cells Given that AipA amino acids 1 to 87 are exposed on the *A. phagocytophilum* surface and contribute to infection, it was assessed if treating DC organisms with heat-inactivated AipA$_{1-87}$ antiserum prior to incubating them with HL-60 cells would inhibit infection. OmpA antiserum, for which its ability to inhibit *A. phagocytophilum* infection was previously validated (Ojogun et al., 2012), was a positive control. Anti-AipA$_{1-87}$ and anti-OmpA each reduced the number of infected cells and the number of bacterial inclusions per cell by approximately 40% (FIGS. 5, A and B). In contrast, AipA$_{249-355}$ antiserum had no effect on *A. phagocytophilum* infection. Consistent with the studies of *A. phagocytophilum* invasins (Ojogun et al., 2012; Kahlon et al., 2013), neither AipA$_{1-87}$ nor OmpA antiserum inhibited bacterial adhesion to HL-60 cells (data not shown).

AipA Targets a sLe$^x$-Capped PSGL-1-Independent Receptor sLe$^x$-capped PSGL-1 is the only known *A. phagocytophilum* receptor on myeloid host cells (Herron et al., 2000), and OmpA binds the α2,3-sialic acid determinant of sLe$^x$ (Ojogun et al., 2012). Since *A. phagocytophilum* interactions with sLe$^x$-capped PSGL-1 involve at least one bacterial surface protein in addition to OmpA (Carlyon et al., 2003; Yago et al., 2003; Reneer et al., 2006; Sarkar et al., 2007; Reneer et al., 2008; Ojogun et al., 2012), it was investigated if AipA$_{1-87}$ antiserum could inhibit bacterial binding to Chinese hamster ovary (CHO) cells transfected to express sLe$^x$-capped PSGL-1 (PSGL-1 CHO cells). These cells are excellent models for studying *A. phagocytophilum* interactions with sLe$^x$-capped PSGL-1 as they, but not untransfected CHO cells that do not express the receptor, support bacterial binding (Carlyon et al., 2003; Xia et al., 2003; Yago et al., 2003; Reneer et al., 2006; Sarkar et al., 2007; Reneer et al., 2008; Troese et al., 2009). DC organisms were incubated with AipA$_{1-87}$ or AipA$_{249-355}$ antiserum prior to being added to PSGL-1 CHO cells. Bacteria pretreated with preimmune serum were a negative control, whereas bacteria pretreated with OmpA antiserum served as a positive control. Additional positive controls for blocking *A. phagocytophilum* adhesion were PSGL-1 CHO cells that had been pretreated with KPL-1 or CSLEX1, which are monoclonal antibodies that block the bacterium's access to the PSGL-1 N-terminus or the α2,3-linked sialic acid determinant of sLe$^x$, respectively (Goodman et al., 1999; Herron et al., 2000; Troese et al., 2009). Incubating DC organisms with OmpA antibody and incubating PSGL-1 CHO cells with KPL-1 or CSLEX1 significantly reduced the numbers of bound DC organisms by two- to three-fold (FIG. 5C). *A. phagocytophilum* bound poorly to untransfected CHO cells. Preimmune serum, anti-AipA$_{1-87}$, and anti-AipA$_{249-355}$ failed to inhibit bacterial binding to PSGL-1 CHO cells. Therefore, AipA contributes to *A. phagocytophilum* cellular invasion by interacting with an sLe$^x$-capped PSGL-1-independent receptor.

A Combination of Antisera Targeting AipA, OmpA, and Asp14 Blocks *A. phagocytophilum* Infection of Host Cells

Figure 6A:
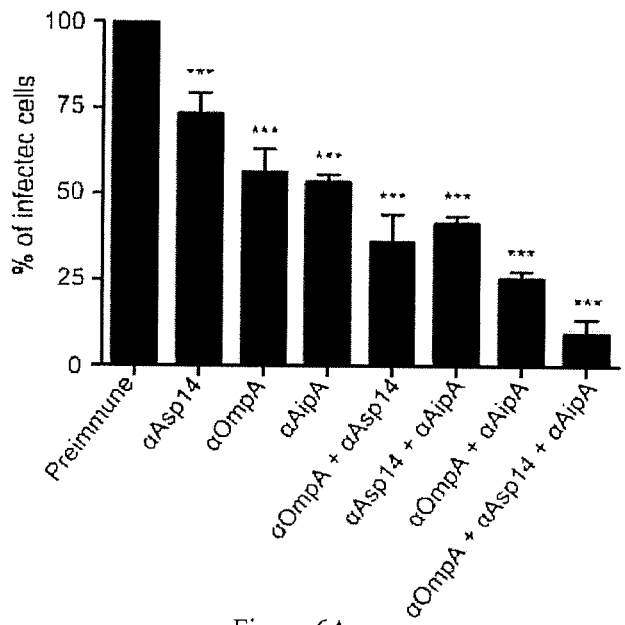
FIG. 6A-B. A combination of antisera targeting AipA, OmpA, and Asp14 blocks *A. phagocytophilum* infection of host cells. DC bacteria were incubated with preimmune serum or antiserum targeting $AipA_{1-87}$, OmpA, and/or Asp14 and then incubated with HL-60 cells. (A) The cells were fixed and screened by confocal microscopy to assess the percentage of infected cells. Results shown are relative to host cells that had been treated with preimmune serum and are the means±SD for three experiments. (B) DNA isolated from the cells was subjected to quantitative PCR analyses. Relative DNA loads of *A. phagocytophilum* 16s rRNA gene were normalized to DNA loads of the human β-actin gene. Results shown are the means±SD of triplicate samples and are representative of three independent experiments with similar results. Statistically significant (*, P<0.05; , P<0.005; *, P<0.001) values relative to the bacterial load of host cells that had been incubated with preimmune antisera are presented.
Figure 6B:
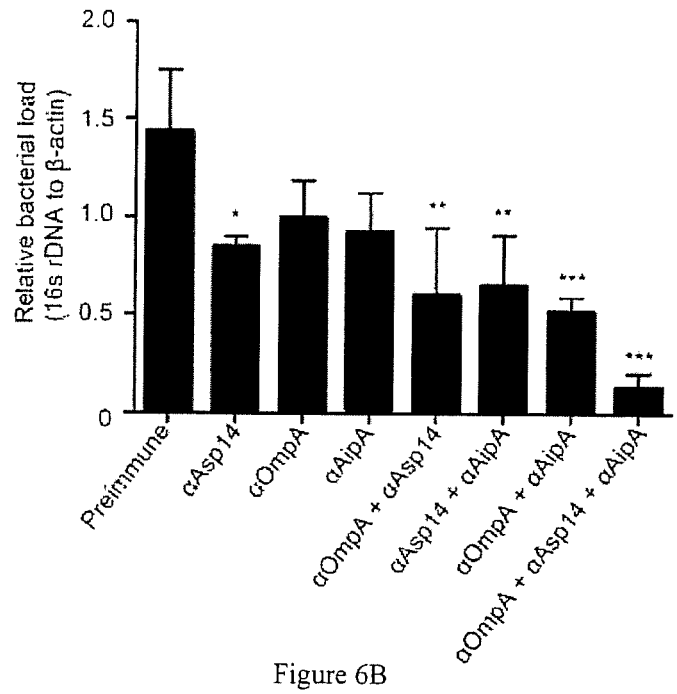

*A. phagocytophilum* infection requires cooperative interactions of multiple invasins with the host cell surface (Truchan et al., 2013). Incubating DC organisms with antiserum targeting full-length OmpA (Ojogun et al., 2012), full-length Asp14 (Kahlon et al., 2013), or AipA$_{1-87}$ significantly, but only partially, reduced *A. phagocytophilum* infection of mammalian host cells. It was therefore investigated if blocking multiple bacterial-host interactions by treating DC organisms with combinations of AipA$_{1-87}$, OmpA, and/or Asp14 antisera could improve blocking efficacy. The result was synergistic: whereas antisera combinations targeting two of the three invasins together more effectively inhibited infection than an antiserum targeting an individual protein, the most effective blocking of *A. phagocytophilum* infection was achieved using antisera against all three invasins (FIG. 6). These data demonstrate that simultaneously targeting AipA, OmpA, and Asp14 is an effective means for preventing or treating *A. phagocytophilum* infection.

The AipA Invasion Domain is Contained within Residues 9 to 21

It was next sought to pinpoint the AipA invasion domain. The competitive agonist and antisera blocking studies indicated that this domain lies within residues 1 to 87. Based on hydrophobicity and surface probability analyses (FIG. 1B), it was rationalized that, of the AipA region of interest, amino acids 9 to 21 and/or 61 to 84 were most likely to facilitate interactions with host cells that promote infection. Accordingly, rabbit antisera against each of these peptides was generated for use in antibody blocking experiments. The AipA region encompassed by residues 165 to 204 (AipA$_{165-204}$) is predicted to be exposed on the *A. phagocytophilum* outer membrane, hydrophilic, and accessible on the surface of AipA (FIG. 1B). Yet, the contribution of AipA$_{165-204}$ to infection was unknown due to our inability to express it as a soluble recombinant protein. Therefore, antisera to peptides corresponding to AipA amino acids 165 to 182 and 183 to 201 was also raised. Each AipA peptide antiserum recognized endogenous AipA in lysates of *A. phagocytophilum* infected, but not uninfected HL-60 cells and was specific for the peptide against which it was raised (FIGS. 7, A and B). Incubating DC organisms with AipA$_{9-21}$ antiserum reduced infection of HL-60 cells by approximately 47% relative to preimmune control serum, an inhibitory effect that was analogous to the reduction achieved using antiserum against AipA$_{1-87}$ or OmpA (FIG. 7C). Antisera against each of the other three AipA peptides and AipA$_{249-355}$ had minimal or no inhibitory effect on infection. Thus, the AipA invasion domain is contained within residues 9 to 21.

Discussion

Invasins of obligate intracellular pathogens are dualistic: they are essential for bacterial entry into host cells but, as such, they are also "Achilles' Heels" that can be blocked to prevent infection and pathogen survival. Targeting invasins of arthropod-transmitted pathogens that are induced during the arthropod blood meal is an attractive approach because of its ability to prevent not only establishment of infection but also disease transmission. Given that *A. phagocytophilum* infection is predicated on the cooperative actions of multiple bacterial surface-associated invasins (Truchan et al., 2013), most of which are induced during the tick transmission bloodmeal (Ojogun et al., 2012; Kahlon et al., 2013), effective prophylaxis against granulocytic anaplasmosis can be achieved by identifying and targeting these invasins. AipA is an attractive target to include in a multicomponent granulocytic anaplasmosis vaccine. It is an invasin that is induced during tick transmission feeding, is preferentially expressed during the bacterium's infectious stage, and functions synergistically with OmpA and Asp14 to mediate optimal infection of mammalian host cells.

The exposure of AipA on the infectious DC form surface makes it accessible to blocking antibodies. Indeed, preincubating DC organisms with AipA antiserum significantly reduced infection of HL-60 cells. Pretreatment of DC bacteria with a combination of antibodies targeting AipA, OmpA, and Asp14 nearly abolished infection, whereas pretreatment with antibodies against one or two of the three invasins was less effective. Thus, AipA, OmpA, and Asp14 are collectively critical for infection and targeting all three together blocks infection in vitro. Spotted fever group *Rickettsia* species, which are in the Order Rickettsiales with *A. phagocytophilum*, also use multiple surface proteins to promote entry into host cells (Martinez et al., 2004; Cardwell et al., 2009; Chan et al., 2009; Chan et al., 2010; Riley et al., 2010). Moreover, this pathogenic strategy is common among numerous other Gram negative bacterial pathogens, including *Chlamydia pneumoniae* (Molleken et al., 2010; Molleken et al., 2013), *Legionella pneumophila* (Garduno et al., 1998; Stone et al., 1998; Cirillo et al., 2001; Chang et al., 2005; Vandersmissen et al., 2010; Duncan et al., 2011), *Bordetella pertussis* (Brennan et al., 1996), *Haemophilus influenzae* (Jurcisek et al., 2007; Giufre et al., 2008; Chang et al., 2011; Dicko et al., 2011; Jalalvand et al., 2013; Singh et al., 2013) and *Leptospira* species (Barbosa et al., 2006; Pinne et al., 2010; Verma et al., 2010; Zhang et al., 2012).

GST-AipA is capable of binding to mammalian cells, which suggests that it functions not only as an invasin but also as an adhesin. Yet, AipA antibodies and GST-AipA$_{1-87}$ each failed to inhibit *A. phagocytophilum* binding to mammalian cells. In these experiments, the role of AipA as an adhesin was presumably masked by the presence of other adhesins/invasins, such as OmpA and Asp14, on the bacterial surface (Ojogun et al., 2012; Kahlon et al., 2013). The AipA receptor is unknown. However, because AipA antibody failed to inhibit *A. phagocytophilum* binding to PSGL-1 CHO cells, it can be concluded that AipA recognizes a sLe$^x$-capped PSGL-1 independent receptor. AipA and Asp14, which also engages a sLe$^x$-capped PSGL-1 independent receptor (Kahlon et al., 2013), complement the sLe$^x$-targeting activity of OmpA (Ojogun et al., 2012).

Bacterial genes that are upregulated during transmission feeding of arthropod vectors are critical for various vector-transmitted bacteria to establish infection in their mammalian hosts (Hinnebusch et al., 1996; Perry et al., 1997; Grimm et al., 2004; Tilly et al., 2006). Consistent with these phenomena, aipA is not expressed by *A. phagocytophilum* during its residence in ISE6 cells or *I. scapularis* nymphs, but is induced when the bacterium is cultivated in mammalian tissue culture cells and during tick transmission feeding. Furthermore, *A. phagocytophilum* expresses AipA during infection of humans and dogs. Thus, AipA is dispensable for bacterial colonization of the tick vector, but is important for infecting mammalian hosts. Similar expression profiles have been observed for the other identified invasins OmpA, Asp14, and APH1235 (Mastronunzio et al., 2012; Ojogun et al., 2012; Kahlon et al., 2013). Also, like APH1235 (Troese et al., 2011; Mastronunzio et al., 2012), AipA is pronouncedly upregulated when the bacterium is in the DC stage. In agreement with the invasive role of the DC morphotype, both proteins are important for establishing and/or maintaining infection in mammalian host cells.

How AipA is transported to and associates with the bacterial outer membrane is unclear, as it lacks a canonical signal peptide that would target it for Sec-dependent or twin-arginine secretion. This conundrum is further complicated as AipA is unique to *A. phagocytophilum* and bears no homology to any known crystal structure. Perhaps AipA is an atypical transmembrane protein or a peripheral membrane protein that is anchored to the bacterial outer membrane via a posttranslational modification. AipA colocalizes with the confirmed outer membrane protein, Msp2 (P44) and functions in concert with OmpA and Asp14, both of which have also been shown to colocalize with Msp2 (P44) (Kahlon et al., 2013; Ojogun et al., 2012). Msp2 (P44) has been proposed to form heteromeric complexes that mediate interactions with host cells (Park et al., 2003). Given that AipA, Asp14, and OmpA synergistically promote *A. phagocytophilum* infection of host cells, it will be important to determine if they do so as a multimeric invasin complex that includes Msp2 (P44).

The AipA invasion domain lies within residues 9 to 21, which is a hydrophilic region of the protein that is exposed on the bacterial surface. Antiserum targeting this span reduces *A. phagocytophilum* infection of host cells by a level comparable to that achieved by antiserum targeting the entire surface-exposed N-terminal domain of AipA. The observed inhibition is specific to anti-AipA$_{9-21}$, as antisera targeting peptides corresponding to all other predicted hydrophilic regions of AipA exhibited no inhibitory effect. Previously, it was discovered that the N-terminal ectodomain of OmpA is required for recognition of α2,3-linked sialic acid of sLe$^x$(Ojogun et al., 2012) and the Asp14 invasion domain lies within residues 101-124 (Kahlon et al., 2013).

Granulocytic anaplasmosis can be debilitating or fatal, and there is no vaccine that protects against the disease. The results described herein show for the first time that simultaneously targeting multiple *A. phagocytophilum* invasins effectively blocks infection in vitro.

Example 2. Essential Domains of *Anaplasma phagocytophilum* Invasins Utilized to Infect Mammalian Host Cells Summary

*Anaplasma phagocytophilum* causes granulocytic anaplasmosis, an emerging disease of humans and domestic animals. The obligate intracellular bacterium uses its invasins OmpA, Asp14, and AipA to infect myeloid and non-phagocytic cells. The present study identifies the OmpA binding domain as residues 59 to 74. Polyclonal antibody generated against a peptide spanning OmpA residues 59 to 74 inhibited *A. phagocytophilum* infection of host cells and binding to its receptor, sialyl Lewis x (sLe$^x$)-capped P-selectin glycoprotein ligand 1. Molecular docking analyses predicted that OmpA residues G61 and K64 interact with the two sLe$^x$ sugars that are important for infection, α2,3-sialic acid and α1,3-fucose. Amino acid substitution analyses demonstrated that K64 was necessary and G61 was contributory for recombinant OmpA to bind to host cells and competitively inhibit *A. phagocytophilum* infection. Adherence of OmpA to RF/6A endothelial cells, which express little to no sLe$^x$ but express the structurally similar glycan, 6-sulfo-sLe$^x$, required α2,3-sialic acid and α1,3-fucose and was antagonized by 6-sulfo-sLe$^x$ antibody. Binding and uptake of OmpA-coated latex beads by myeloid cells was sensitive to sialidase, fucosidase, and sLe$^x$ antibody. The Asp14 binding domain was also defined, as antibody specific for residues 113 to 124 inhibited infection. An antibody cocktail targeting the OmpA, Asp14, and AipA binding domains neutralized *A. phagocytophilum* binding and infection of host cells. This study dissects OmpA-receptor interactions and demonstrates the effectiveness of binding domain-specific antibodies for blocking *A. phagocytophilum* infection.

Introduction

Human granulocytic anaplasmosis (HGA) is an emerging tick-borne zoonosis in the United States, Europe, and Asia (Truchan et al., 2013). The number of HGA cases reported to the U. S. Centers for Disease Control and Prevention rose nearly seven-fold between 2003 and 2012 (CDC 2013; Hopkins et al., 2005). Seroprevalence data indicate that the disease is underreported in some endemic regions (Hao et al., 2013; Zhang et al., 2012; Zhang et al., 2009; Aguero et al., 2002; Bakken et al., 1998). HGA can also be spread via perinatal, nosocomial, and blood transfusion routes (Bakken et al., 1998; Alhumaidan et al., 2013; Annen et al., 2012; Jereb et al., 2012). It is an acute illness characterized by fever, chills, headache, malaise, leukopenia, thrombocytopenia, and elevated liver enzymes. Complications can include shock, seizures, pneumonitis, rhabdomyolysis, hemorrhage, increased susceptibility to secondary infections, and death. Risk for complications and fatality is greater for the elderly, the immunocompromised, and when proper diagnosis and/or antibiotic therapy are delayed (Truchan et al., 2013). The causative agent of HGA is *Anaplasma phagocytophilum*, an obligate intracellular bacterium that exhibits a tropism for neutrophils (Truchan et al., 2013). *A. phagocytophilum* is carried by a variety of wild animal reservoirs and, in addition to humans, causes disease in domestic animals including dogs, cats, horses, and sheep (Stuen et al., 2013).

*A. phagocytophilum* exhibits a biphasic developmental cycle similar to that of *Chlamydia* spp., *Ehrlichia* spp., and *Coxiella burnetii* (Bastidas et al., 2013; Minnick et al., 2012; Zhang et al., 2007; Troese et al., 2009). The *A. phagocytophilum* infectious dense-cored (DC) form promotes its receptor-mediated uptake into a host cell derived vacuole. Within its vacuole, the DC develops into the non-infectious reticulate cell (RC) for that replicates to form a bacterial cluster called a morula (Troese et al., 2009; Ojogun et al., 2012). RCs then convert back to DCs and are released to initiate the next infection cycle (Troese et al., 2009).

Sialyl Lewis x ([NeuAcα(2-3)Galβ1-4(Fucα1-3)GlcNac]; sLe$^c$), an α2,3-5 sialylated and α1,3-fucosylated core-2 O-linked glycan that caps the N-termini of selectin ligands (Sperandio et al., 2006), is a critical *A. phagocytophilum* receptor (Goodman et al., 1999). sLe$^x$ is richly expressed on mammalian cells that are permissive for *A. phagocytophilum* infection such as neutrophils, bone marrow progenitors, and promyelocytic HL-60 cells (Karakantza et al., 1994; Symington et al., 1985; Fukuda et al., 1984). *A. phagocytophilum* recognizes sLe$^x$ that caps the N-terminus of P-selectin glycoprotein ligand-1 (PSGL-1) on these myeloid cells (Goodman et al., 1999; Herron et al., 2000). Neutrophils and HL-60 cells that have been treated with an sLe$^x$ blocking antibody, from which surface sialic acids have been enzymatically removed, or that are devoid of sialyltransferase and/or α1,3-fucosyltransferase activity are resistant to *A. phagocytophilum* binding and infection (Ojugun et al., 2012; Goodman et al., 1999; Carylon et al., 2003; Yago et al., 2003). *A. phagocytophilum* also infects rhesus monkey choroidal (RF/6A) endothelial cells, megakaryoblastic MEG-01 cells, and bone marrow-derived mast cells in tissue culture. Infection of these non-myeloid host cell types depends on sLe$^x$ itself, α2,3-sialic acid, and/or α1,3-fucose (Huang et al., 2012; Kahlon et al., 2013; Mastronunzio et al., 2012; Ojogun et al., 2011). Thus, sLe$^x$ and possibly other closely related α2,3-sialylated and α1,3-fucosylated molecules are essential for efficient *A. phagocytophilum* infection of mammalian cells.

*A. phagocytophilum* OmpA and α2,3-sialic acid (N-acetylneuraminic acid [Neu5Ac], further referred to as sialic acid throughout) was identified as the bacterium's first adhesin/invasin-receptor pair (Ojogun et al., 2012). OmpA binding to the α2,3-sialic acid determinant of sLe$^x$ on myeloid cells and to α2,3-sialylated glycans on RF/6A cells are vital steps in *A. phagocytophilum* invasion of these host cell types (Ojogun et al., 2012). Exposure of OmpA on the *A. phagocytophilum* DC surface makes it accessible to antibodies (Ojogun et al., 2012), which could be used to exploit the bacterium's obligatory intracellular nature to block the host cell invasion step that is essential for survival. The OmpA binding domain that recognizes α2,3-sialic acid lies within amino acids 19 to 74 (Ojogun et al., 2012), but has yet to be specifically identified. The *A. phagocytophilum* OMP that recognizes α1,3-fucose is unknown. As shown in Example 1, OmpA functions in concert with two additional invasins that are also upregulated during tick transmission feeding, Asp14 (14-kDa *A. phagocytophilum* surface protein) and AipA (*A. phagocytophilum* invasion protein A), to promote optimal *A. phagocytophilum* entry into mammalian host cells (Kahlon et al., 2013; Seidman et al., 2014). The AipA binding domain was defined in Example 1 as residues 9 to 21.

In this study, antibody blocking, in silico docking models, and site directed mutagenesis was used to identify the *A. phagocytophilum* OmpA binding domain, specifically the key residues that are essential for its adhesin/invasin activity, and determined that it recognizes both α2,3-sialic acid and α1,3-fucose. This work represents the most detailed study of any rickettsial adhesin/invasin-receptor pair to date. Furthermore, the Asp14 binding domain was identified and it was confirmed that an antibody cocktail targeting the binding domains of OmpA, Asp14, and AipA nearly abolishes *A. phagocytophilum* infection of host cells.

Materials and Methods

Cell Lines and Cultivation of *A. phagocytophilum*

Uninfected and *A. phagocytophilum* infected (NCH-1 strain) HL-60 cells (ATCC CCL-240) and RF/6A cells (ATCC CRL-1790, Manassas, Va.) were maintained as previously described (Troese et al., 2009; Huang et al., 2012). CHO (−) and PSGL-1 CHO cells were cultivated as described (Li et al., 1996).

Site Directed Mutagenesis and Recombinant Proteins pGST-OmpA, which encodes OmpA19-205 N-terminally fused to GST, was previously constructed (Ojogun et al., 2012). Using pGST-OmpA as the template, the QuikChange® Lightning (Agilent Technologies, Santa Clara, Calif.) protocol was used per the manufacturer's guidelines to perform site-directed insertions and point mutagenesis of the ompA insert sequence. For site directed insertions, a five-amino acid insert sequence (CLNHL; SEQ ID NO:75) was selected based on previous studies that had successfully employed the linker-scanning method (Anton et al., 2004; Okoye et al., 2006), which is used to insert peptide "linkers" to disrupt protein binding domains without perturbing overall protein structure. The sequence chosen for the insertion peptide, CLNHL (SEQ ID NO:75), was a consensus sequence based on the most common amino acids at their respective positions in the insertion peptides used in prior studies (Anton et al., 2004; Okoye et al., 2006). The nucleotide sequence, 5'-TGCCTGAACCACCTG-3' (SEQ ID NO:76), which encoded CLNHL (SEQ ID NO:75), was inserted in the ompA sequence of pGST-OmpA between ompA nucleotides 102 and 103, 162 and 163, 186 and 187, 201 and 202, 216 and 217, and 231 and 232 to yield plasmids that encoded GST-OmpA proteins bearing CLNHL inserts between OmpA amino acids 34 and 35, 54 and 55, 62 and 63, 67 and 68, 72 and 73, and 77 and 78, respectively. Likewise, the QuikChange protocol was used to perform site directed mutagenesis to yield plasmids that encoded GST-OmpA proteins having R32, D53, K60, G61, K64, K65, E69, and/or E72 converted to alanine. GST-OmpA mutants were expressed and purified as previously described (Ojogun et al., 2012). Plasmids encoding His-tagged wild type and site-directed mutant OmpA proteins were generated by amplifying wild type and mutant ompA sequences using primers containing ligase-independent cloning (LIC) tails and annealing the amplicons into the pET46 Ek/LIC vector (Novagen, EMD Millipore, Darmstadt, Del.) per the manufacturer's instructions. His-OmpA proteins were expressed and purified by immobilized metal-affinity chromatography as previously described (Miller et al., 2011).

Molecular Modeling of the OmpA-sLe$^x$ Interaction

To obtain a putative three-dimensional OmpA protein structure, the mature OmpA sequence was threaded onto the solved crystal structures of proteins with similar sequences using the PHYRE2 server as previously described (Ojogun et al., 2012). Amino acids 19 to 150 (73% of the mature OmpA sequence) were modeled with greater than 90% confidence to known structures for similar proteins (Protein Data Bank [PDB] files 2aiz [*Haemophilus influenzae* OmpP6 peptidoglycan associated lipoprotein (PAL)], 4g4v [*Acinetobacter baumanni* PAL], 4b5c [*Burkholderia pseudomallei* PAL], 3ldt [*Legionella pneumophila* OmpA], 2kgw [*Mycobacterium tuberculosis* OmpATb]). The remainder of the protein lacked sufficient homology to any experimentally derived structure, but could be modeled using the Poing method (Kelley et al., 2009), which was performed as part of the Phyre2 analyses. The sLe$^x$-PSGL-1 peptide (residues 61 to 77) and the sLe$^x$ glycan itself was extracted from the solved crystal structure of PSGL-1 (PDB 1G1S) in PyMol and saved as an individual PDB file. Open Babel software was used to convert PDB files to PDBQT (Protein Data Bank, Partial Charge and Atom Type) format in order to perform OmpAsLe$^x$ docking analysis. AutoDock Tools software was used to generate the docking output files for both the OmpA protein structure and the sLe$^x$ ligand. The search location for OmpA was generated in AutoDock Tools by setting a search grid that encompassed OmpA residues 19 to 74. Molecular docking was performed using AutoDock Vina to identify potential points of interaction between OmpA and sLe$^x$. The top two OmpA-sLe$^x$ models generated by AutoDock Vina had the same predicted affinity value of −4.2 kcal/mol and were selected for analysis in PyMol to determine potential points of contact.

Antibodies, Reagents, Enzyme-Linked Immunosorbent Assay (ELISA), and Western Blotting To generate antisera specific to the OmpA and Asp14 binding domains, peptides corresponding to OmpA residues 23 to 40, 41 to 58, and 59 to 74 and Asp14 residues 98 to 112 and 113 to 124 were synthesized, conjugated to keyhole limpet hemocyanin, administered to rabbits, and the resulting OmpA and Asp14 peptide-specific sera were affinity-purified by New England Peptide (Gardner, Mass.). Each peptide antiserum's specificity for the peptide against which it had been raised and for its protein target was determined by ELISA using the TMB substrate kit (Thermo Scientific, Waltham, Mass.) following the manufacturer's instructions or by Western blot analysis as previously described (Carylon et al., 2002). Mouse anti-AipA peptide antisera have been previously described (Seidman et al., 2014). sLe$^x$ 564 antibodies CSLEX1 (BD Biosciences, San Jose, Calif.) and KM93 (Millipore, Darnstadt, Del.) and PSGL-1 N-terminus-specific antibody 565 KPL-1 (BD Biosciences) were obtained commercially. Fab fragments of OmpA and Asp14 peptide-specific antisera were generated using the Fab Preparation Kit (Pierce, Rockford, Ill.) according to the manufacturer's instructions. His tag and Alexa Fluor 488-conjugated secondary antibodies and Alexa Fluor 488-conjugated streptavidin were obtained from Invitrogen (Carlsbad, Calif.). Biotinylated AAL and MAL II were obtained from Vector Labs (Burlingame, Calif.). Glycosidases used in this study were α2,3/6-sialidase (Sigma-Aldrich, St. Louis, Mo.) and α1,3/4-fucosidase (Clontech, Mountain View, Calif.).

Sequence Alignments

The NCH-1 gene sequence for ompA (APH0338) was previously determined (Ojogun et al., 2012; Kahlon et al., 2013; Seidman et al., 2014). A Protein BLAST (basic local alignment search tool) search using the NCH-1 OmpA predicted protein sequence as the query was used to identify homologs in other Anaplasmataceae species and in *A. phagocytophilum* strains HZ (Rikihisa et al., 1997), HGE1 (Goodman et al., 1996), Dog (Al-Khedery et al., 2012), JM (Johnson et al., 2011), MRK (Madigan et al., 1987; Gribble, 1969), CRT35, CRT38 (Massung et al., 2007), and NorV2 (Al-Khedery et al., 2012), for which the genomes are available. All of these strains except for NorV2 had been originally isolated from clinically affected humans and animals. HZ and HGE1 were recovered from human patients in Westchester, N.Y., USA and Minnesota, USA, respectively. The Dog and JM strains were isolated from a dog in Minnesota, USA and a meadow jumping mouse (*Zapus hudsonius*) in Camp Ripley, Minn., USA. MRK had been recovered from a horse in California, USA. CRT35 and CRT38 are isolates of the *A. phagocytophilum* Ap-variant 1 strain that were recovered from ticks collected at Camp Ripley, Minn., USA. NorV2 is a naturally occurring *A. phagocytophilum* isolate that was maintained in an experimentally infected lamb, exhibits reduced virulence in sheep, and differs in its 16S rRNA gene sequence when compared to other sheep isolates. OmpA sequence alignments were generated using Clustal W.

Binding of Recombinant OmpA Proteins to Host Cells

For binding of His- or GST-tagged OmpA proteins to host cells, RF/6A or HL-60 cells were incubated with 4 μM recombinant protein in culture media for 1 h in a 37° C. incubator supplemented with 5% C02 and a humidified atmosphere. To assess for the presence of sLe$^x$ or 6-sulfo-sLe$^x$ on RF/6A cell surfaces, the cells were fixed in 4% PFA in PBS for 1 h at room temperature followed by incubation with CSLEX1, KM93, or G72 for 1 h at room temperature. Antibody incubations and washes were performed as described previously (Reneer et al., 2006). Spinning-disk confocal microscopy using an Olympus BX51 microscope affixed with a disk-spinning unit (Olympus, Center Valley, Pa.) and/or flow cytometry using a BD FACS Canto™ II (BD Biosciences) were performed to assess binding of antibodies or His-OmpA proteins to host cell surfaces as previously described (Ojogun et al., 2012; Kahlon et al., 2013). In some cases, RF/6A cells were pretreated with a2,3/6-sialidase, α1,3/4-fucosidase, AAL, MAL II, or sLe$^x$- or 6-sulfo-sLe$^x$-specific antibodies prior to incubation with His-OmpA.

Competitive Inhibition of *A. phagocytophilum* Binding and Infection

Competitive inhibition assays utilizing recombinant protein or antibody were performed and analyzed by spinning-disk confocal microscopy as previously described (Ojogun et al., 2012; Kahlon et al., 2013). To determine if *A. phagocytophilum* binding to PSGL-1 CHO cells or infection of RF/6A cells involved bacterial binding to host cell surface fucose residues, the host cells were treated with α1,3/4-fucosidase (10 μU/mL) prior to the addition of DC organisms and assessment for bacterial binding or infection as previously described (Troese et al., 2009; Ojogun et al., 2012). For competitive inhibition assays using antisera raised against OmpA or Asp14 peptides, *A. phagocytophilum* DC bacteria were incubated with serially diluted concentrations of antiserum. Preimmune rabbit serum (200 µg/mL) was a negative control. Assays using combinations of two or three different OmpA, Asp14, or AipA peptide antibodies were performed using 100 µg/mL per antibody. Preimmune serum (200 µg/mL or 300 µg/mL, based on the combined total of peptide antisera) served as a negative control. Competitive inhibition assays using OmpA and/or Asp14 Fab fragments were performed exactly as described for antisera. Preimmune Fab fragments served as a negative control.

OmpA Coated Bead Uptake Assay $1.8 \times 10^7$ red fluorescent sulfate-modified 1.0 µm diameter microfluorospheres (Life Technologies, Carlsbad, Calif.) were mixed by rotation with 8 µg of His-OmpA, or His-OmpA proteins bearing alanine substitutions, in 400 µL of 50 mM phosphate buffered saline (PBS) supplemented with 0.9% NaCl at room temperature overnight in the absence of light. The His-OmpA coated beads were centrifuged at 5,000 g for 25 min, followed by three washes in 50 mM PBS. Coated beads were resuspended in 400 µL of 50 mM PBS, 0.9% NaCl, 1% BSA and stored at 4° C. until use. To validate that the beads were conjugated with His-OmpA, $1.8 \times 10^4$ of the beads were screened by immunofluorescent microscopy using mouse polyclonal OmpA antisera followed by Alexa Fluor 488-conjugated goat anti-mouse IgG as described (Ojogun et al., 2012). To assess binding to and uptake by HL-60 or RF/6A cells, His-OmpA coated beads or uncoated control beads were resuspended in the appropriate culture medium and added to host cells at a concentration of 500 beads/cell. For adherent RF/6A cells, beads were centrifuged onto the host cells at 1,000 g for 5 min. The cells plus beads were incubated for 1 h at 37° C. in a 5% $CO_2$ supplemented humidified incubator followed by washing the cells three times with PBS to remove unbound beads. Non-adherent HL-60 cells were mixed with the beads in suspension, incubated as described above, and three PBS washes were performed intermittently between five-min spins performed at 300 g. To assess binding, the host cells were fixed in 4% paraformaldehyde (PFA) in PBS, mounted with ProLong® Antifade Gold gel mounting medium containing 4',6-diamidino-2-phenylindole (DAPI) (Invitrogen), and analyzed by spinning-disk confocal microscopy as previously described (Ojogun et al., 2012). For uptake assays, after the final wash, the host cells were resuspended in culture medium and cultivated for an additional 7 h. The cells were washed three times in PBS, incubated with a 0.25% trypsin solution (Hyclone™, Thermo Scientific, Waltham, Mass.) for 10 min at 37° C. to cleave host cell surface proteins and consequently remove noninternalized beads, and washed three times with PBS. HL-60 cells were cytospun onto glass microscope slides and fixed, mounted, and screened as described above. RF/6A cells were added to wells containing coverslips, incubated overnight in a 37° C. incubator supplemented with 5% $CO_2$ and a humidified atmosphere to allow the host cells to adhere prior to further processing. To determine if His-OmpA coated bead binding or uptake was temperature sensitive, some experiments were performed at 4° C. To assess the contribution of sLe$^x$ or PSGL-1 determinants to His-OmpA coated bead binding and uptake, host cells were pretreated with α2,3-sialidase (5 ag/mL), α1,3/4-fucosidase (10 µU/mL), sLe$^x$-specific antibody CSLEX1 (10 µg/mL), PSGL-1 N-terminus-specific antibody KPL-1 (10 µg/mL), or vehicle or isotype controls as previously described (Ojogun et al., 2012) prior to the bead binding and uptake assays.

Scanning Electron Microscopy

Coverslips of RF/6A cells were incubated with OmpA coated or control beads as described above. The coverslips were fixed in 2.0% glutaraldehyde in 0.1 M sodium cacodylate for 1 h at room temperature. The coverslips were subjected to two 10-min washes in 0.1 M sodium cadodylate and fixed in 1.0% osmium tetroxide in 0.1 M sodium cacodylate for 1 h. The coverslips were rinsed two more times with 0.1 M sodium cadodylate buffer for 10 min each. The samples were dehydrated by successive 5-min incubations in 50% ethanol, 70% ethanol, 80% ethanol, 95% ethanol, and three 10-min washes in 10% ethanol. Next, the samples were incubated three times for 30 min each in hexamethyldisilazane, air-dried, mounted with silver paint, and sputter coated with gold before imaging on a Zeiss EVO® 50XVP scanning electron microscope (Thornwood, N.Y.). For HL-60 cells incubated in suspension with beads, the samples were retained on a 0.1 µm filter and processed exactly as described for RF/6A cells.

Statistical Analyses

The Prism 5.0 software package 680 (Graphpad, San Diego, Calif.) was used to determine the statistical significance of data using one-way analysis of variance (ANOVA) or the Student's T-test, as previously described (Ojogun et al., 2012). Statistical significance was set to $P<0.05$.

Results

Figure 8A:
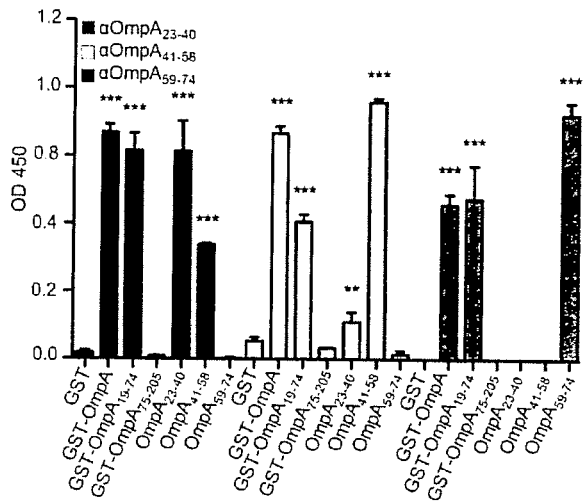
FIG. 8A-C. OmpA amino acids 59 to 74 are critical for *A. phagocytophilum* to bind to $sLe^x$-capped PSGL-1 and for infection of mammalian host cells. (A) ELISA in which OmpA23-40, OmpA41-58, and OmpA59-74 antibodies (diluted 1:1600) were used to screen wells coated with GST, GST-OmpA, GST-OmpA19-74, GST-OmpA75-205, or peptides corresponding to OmpA23-40, OmpA41-58, or OmpA59-74. Results shown are the mean±SD of triplicate samples and are representative of three independent experiments with similar results. (B) Pretreatment of *A. phagocytophilum* with OmpA59-74 antibody inhibits infection of HL-60 cells in a dose-dependent manner. DC bacteria were incubated with 200 μg/ml of preimmune serum, 200 μg/ml of serum raised against GST-OmpA, or twofold serially-diluted concentrations of sera raised against OmpA23-40, OmpA41-58, or OmpA59-74 ranging from 0 to 200 μg/ml and then incubated with HL-60 cells. The infection was allowed to proceed for 24 h after which the cells were fixed and examined using immunofluorescence microscopy to quantify the percentage of infected cells. Results shown are relative to host cells that had been incubated with bacteria exposed to preimmune serum and are representative of three experiments with similar results. (C) OmpA59-74 antibody inhibits *A. phagocytophilum* binding to $sLe^x$-capped PSGL-1. DC bacteria were exposed to preimmune serum, antibodies against OmpA, OmpA23-40, OmpA41-58, or OmpA59-74 and then incubated with PSGL-1 CHO cells. Bacteria that were not exposed to antibodies and incubated with PSGL-CHO cells or CHO (−) cells were positive and negative controls, respectively, for bacterial binding. The mean numbers±SD of bound DC organisms per cell were determined using immunofluorescence microscopy. Results shown are the mean±SD of six combined experiments. Statistically significant ( P<0.005; *P<0.001) values are indicated.
Figure 8B:
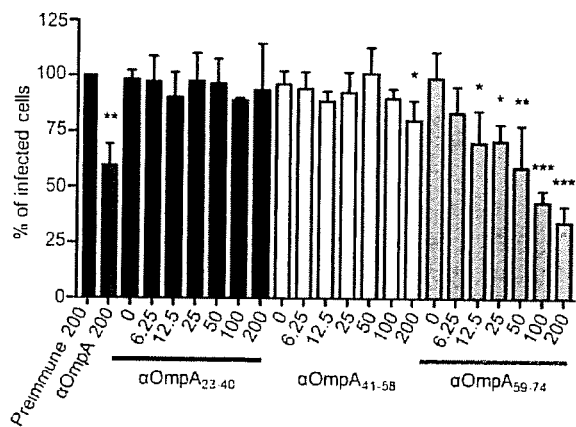
Figure 8C:
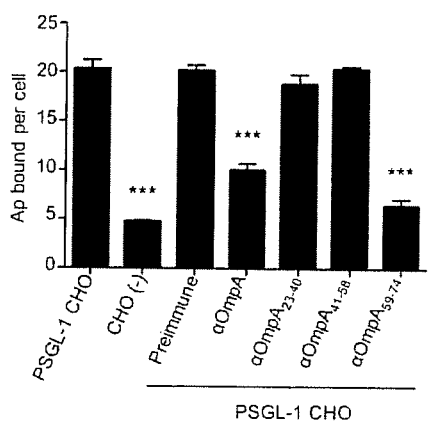

OmpA Amino Acids 59 to 74 are Critical for *A. phagocytophilum* to Bind to sLe$^x$ Capped PSGL-1 and for Infection of Mammalian Host Cells The OmpA region that is important for *A. phagocytophilum* infection of mammalian host cells lies within residues 19 to 74 (OmpA19-74) (Ojogun et al., 2012). As a first step in further delineating the binding domain, polyclonal antisera against peptides corresponding to OmpA amino acids 23 to 40, 41 to 58, and 59 to 74 were raised. It was verified that the antisera were specific for OmpA by confirming that each recognized recombinant forms of mature OmpA (minus the signal sequence; corresponding to residues 19 to 205 and hereafter referred to as OmpA) and OmpA19-74, but neither OmpA75-205 nor Asp14 (FIG. 8A). Anti-OmpA41-58 and anti-OmpA59-74 were specific for their target peptides at all serum dilutions. Anti-OmpA23-40 was specific for its target peptide at most dilutions tested, but exhibited low level recognition of OmpA41-58 at dilutions below 1:12, 800 (FIG. 8A). Next, it was evaluated if any of the OmpA peptide antisera could inhibit *A. phagocytophilum* infection of host cells. Bacteria that had been treated with anti-OmpA or preimmune serum served as positive and negative controls, respectively. As previously observed (Ojogun et al., 2012), OmpA antibody reduced the percentage of *A. phagocytophilum* infected HL-60 cells by approximately 40% (FIG. 8B). OmpA59-74 antibody exhibited a dose-dependent inhibitory effect and, at a concentration of 200 ug/ml, reduced the percentage of infected HL-60 cells by approximately three-fold. Antisera targeting OmpA residues 23 to 40 and 41 to 58 exhibited very little to no inhibition of infection, regardless of concentration. Unless otherwise specified, all antisera were used at a concentration of 200 ug/ml in subsequent blocking experiments.

sLe$^x$-capped PSGL-1 is an *A. phagocytophilum* receptor on human myeloid cells (Goodman et al., 1999), and OmpA has been shown to bind the sLe$^x$ portion (Ojogun et al., 2012). Because OmpA59-74 antibody significantly inhibited *A. phagocytophilum* infection of HL-60 cells, it was rationalized that OmpA amino acids that are critical for engaging the receptor are within residues 59 to 74. To test this hypothesis, the abilities of antisera targeting various portions of OmpA to interfere with *A. phagocytophilum* binding to Chinese hamster ovary cells transfected to express sLe$^x$-capped PSGL-1 (PSGL-1 CHO cells) was assessed. These cells are useful models for studying *A. phagocytophilum* interactions with sLe$^x$ and/or PSGL-1 because they robustly support bacterial binding but not infection, while untransfected CHO [CHO (−)] cells that lack expression of these receptors poorly support bacterial binding. Anti-OmpA59-74 reduced the mean number of bound *A. phagocytophilum* DC organisms per PSGL-1 CHO cell by approximately fourfold to nearly that of CHO (−) cells (FIG. 8C). Anti-OmpA reduced bacterial binding to PSGL-1 CHO cells by approximately two-fold. Anti-OmpA23-40, anti-OmpA41-58, and preimmune serum had no effect. These results indicate that the OmpA binding domain lies within amino acids 59 to 74 and this region is important for *A. phagocytophilum* recognition of sLe$^x$-capped PSGL-1.

Figure 9A:
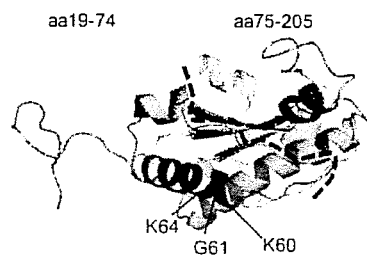
FIG. 9A-F. Molecular docking models of *A. phagocytophilum* OmpA-$sLe^x$ interactions. (A) Predicted tertiary structure for *A. phagocytophilum* OmpA. The dotted line separates the regions encompassed by residues 19 to 74 and 75 to 205. Residues K60, G61, and K64 positions are indicated. (B) Stick representation of the N-terminal PSGL-1 amino acids 61 to 77 capped with $sLe^x$ derived from PDB 1g1s. The $sLe^x$ glycan extends off of threonine 73. $sLe^x$ linkages and individual sugar residues are denoted. (C) Electrostatic surface map of *A. phagocytophilum* OmpA, as generated using the PyMol APBS plugin. The image is oriented as in (A). (D) The electrostatic surface map as in (C) rotated 1800 around the y-axis. The dotted line is a demarcation between the regions encompassed by residues 19 to 74 and 75 to 205, which have overall cationic and anionic surface charges, respectively. (E and F) OmpA and $sLe^x$ interactions predicted by the Autodock Vina algorithm. OmpA is presented as a ribbon model, $sLe^x$ as a stick model, and hydrogen bonding by dotted lines. OmpA residue K64 is predicted to interact with α2,3-1080 sialic acid of $sLe^x$ (E and F). Residue G61 is predicted to interact with either α2,3-sialic acid (E) or α1,3-fucose of $sLe^x$ (F). Residue K60 is predicted to interact with § 1,3 galactose of $sLe^x$ (F).
Figure 9B:
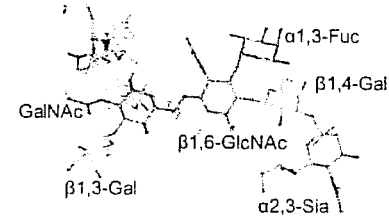
Figure 9C:
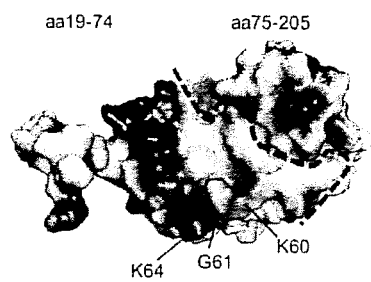
Figure 9D:
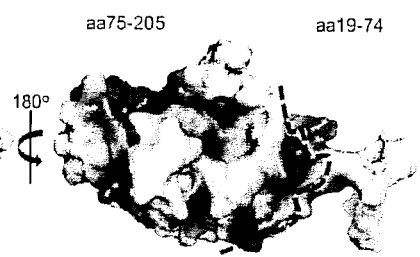

Molecular Docking Models of *A. phagocytophilum* OmpA-sLe$^x$ Interactions Suggest that Residues within OmpA59-74 Engage sLe$^x$ To complement the antibody blocking experiments, molecular modeling and docking was used to identify the OmpA amino acids that possibly contact sLe$^x$. First, a three-dimensional model of the invasin was generated. A crystal structure for *A. phagocytophilum* OmpA has yet to be determined, but an abundance of crystal structures for similar bacterial proteins have been determined. The Phyre2 (Protein Homology/Analogy Recognition Server version 2.0) server, which predicts three dimensional structures for protein sequences and threads the predicted models on known crystal structures (Kelley et al., 2009), was used to generate a tertiary structure model for OmpA (FIG. 9A). The resulting homology model predicted that OmpA residues 59 to 74 form part of a surface-exposed alpha helix (FIG. 9A), which could interact with ligands. Surface electrostatic values calculated using the adaptive Poisson-Boltzmann solver (APBS) plugin for PyMOL indicated that OmpA amino acids 19 to 74 have an overall cationic surface charge. The rest of the modeled protein exhibits an overall anionic surface charge (FIGS. 9C and D). These findings are consistent with prior observations that bacterial and viral proteins that interact with sLe$^x$ and/or sialic acid do so at cationic surface patches (Chung et al., 2007; Hermans et al., 2012; Dormitzer et al., 2002; Stein et al., 1994; Varghese et al., 1992).

Figure 9E:
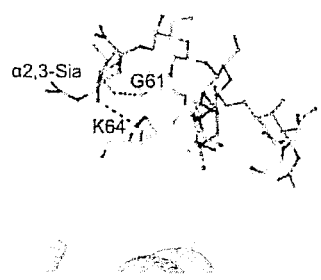
Figure 9F:
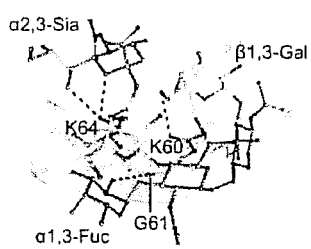

For docking predictions, the sLe$^x$ glycan (FIG. 9B) was extracted from the crystal structure of sLe$^x$-capped PSGL-1 (DOI:10.2210/pdb1g1s/PDB). Autodock Vina was used to predict how OmpA might interact with sLe$^x$. The search grid encapsulated OmpA19-74 (FIG. 9A). The top two docking models, each with the same predicted affinity value of −4.2 kcal/mol, displayed similar interactions between sLe$^x$ and the OmpA region encompassed by amino acids 59 to 74. In both models, K64 of OmpA was predicted to bind the α2,3-sialic acid residue of sLe$^x$ (FIGS. 9E and F). G61 was also predicted to interact with sLe$^x$ in both models, though it was predicted to bind α2,3-sialic acid in one model and α1,3-fucose in the other. Lastly, K60 was predicted to bind the ß1,3-galactose residue of sLe$^x$ in the docking model presented in FIG. 9F. Together, the in silico predictions and peptide antibody blocking results suggest that OmpA59-74 contains critical residues that interact with sLe$^x$ to promote *A. phagocytophilum* infection of host cells.

OmpA is Conserved Among *A. phagocytophilum* Strains and K64 is Conserved Among Anaplasmataceae OmpA Proteins Aligning the OmpA sequence from the *A. phagocytophilum* NCH-1 strain, which was originally isolated from a HGA patient in Nantucket, Mass. (Kolbert et al., 1997), with those encoded by geographically diverse *A. phagocytophilum* isolates that had been recovered from infected humans, animals, and ticks revealed that OmpA is highly conserved among these strains (FIGS. 10A and B). Eight of the nine sequences were identical. The OmpA of NorV2 Norwegian sheep isolate had only three amino acid differences, none of which were within the binding domain encompassed by residues 59 to 74. The high degree of OmpA sequence conservation further supports the invasin's importance to *A. phagocytophilum* pathobiology. Next NCH-1 OmpA residues 19 to 74 were aligned with corresponding regions of OmpA homologs from *A. marginale* and *Ehrlichia* spp., which are in the family Anaplasmataceae with *A. phagocytophilum* and infect bovine erythrocytes and human and animal monocytes, respectively (Carylon et al., 2012; Mansueto et al., 2012; Suarez et al., 2011). *A. phagocytophilum* OmpA K64 that was predicted to potentially interact with sLe$^x$ (FIGS. 9, E and F), was the only binding domain residue that was conserved among all Anaplasmataceae OmpA regions examined (FIG. 10B). Additional residues within the *A. phagocytophilum* OmpA binding domain, including the other two predicted to interact with sLe$^x$, K60 and G61 (FIGS. 9, E and F), were conserved among *Anaplasma* spp. but not *Ehrlichia* spp. OmpA proteins (FIG. 10B).

Figure 11A:
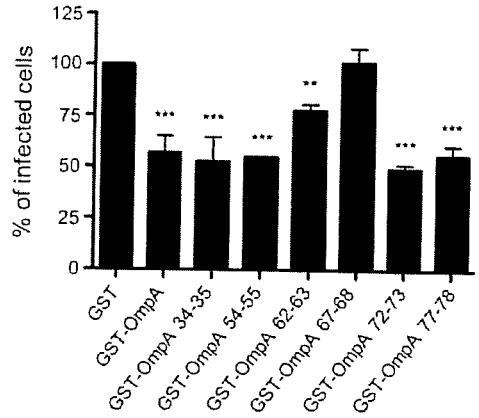
FIGS. 11A-D. G61 and K64 are essential for recombinant OmpA to optimally bind to mammalian host cells and competitively inhibit *A. phagocytophilum* infection.
Figure 11B:
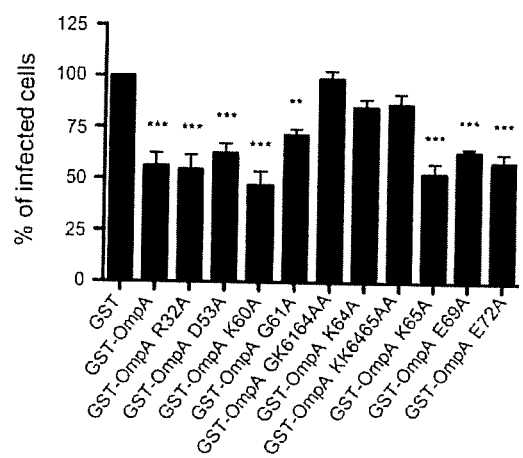
Figure 11C:
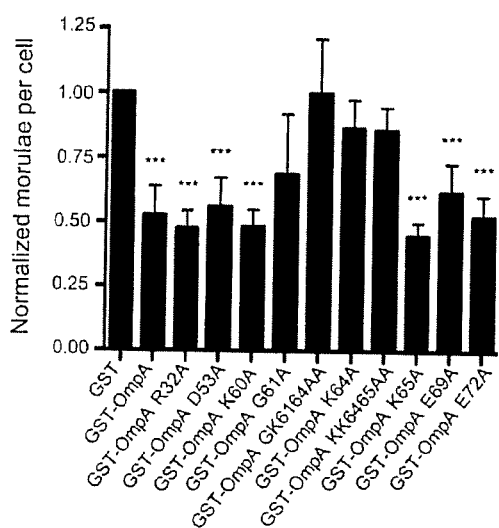

G61 and K64 are Essential for Recombinant OmpA to Optimally Bind to Mammalian Host Cells and Competitively Inhibit *A. phagocytophilum* Infection Because *A. phagocytophilum* is an obligate intracellular bacterium, developing a knock out-complementation system for this organism has proved challenging and has not been described. Therefore, a series of alternative approaches was utilized to further functionally evaluate OmpA. Recombinant OmpA can be used as a competitive agonist to block *A. phagocytophilum* access to its receptor and thereby inhibit infection. This phenomenon was exploited to further define the OmpA amino acids that are critical for receptor recognition and bacterial uptake by assessing the competitive agonist abilities of OmpA proteins having site-directed amino acid changes. This approach was built on the rationale that OmpA proteins in which the binding domain was disrupted would be unable to inhibit infection. First, OmpA proteins N-terminally fused to glutathione-S-transferase (GST) were generated, each of which had an insertion of the peptide CLNHL at one of six different sites within residues 19 to 78. This approach has been used in previous studies to disrupt proteins' binding domains without perturbing overall protein structure, and the insertion sequence that was devised for this purpose was a consensus of the insertion peptides used in those studies (Anton et al., 2004; Grande et al., 2007; Okoye et al., 2006). Incubating HL-60 cells with the positive control, GST-OmpA, prior to the addition of DC bacteria resulted in a significant reduction in the percentage of infected cells relative to GST alone (FIG. 11A). GST-OmpA proteins carrying insertions between residues 67 and 68 and between 62 and 63 were completely and partially abrogated, respectively, in their abilities to inhibit *A. phagocytophilum* infection. GST-OmpA proteins bearing insertions at other sites were unaffected in their ability to inhibit infection.

Next the specific amino acids of GST-OmpA that were critical for it to inhibit *A. phagocytophilum* infection were identified. The competitive agonist assay was repeated using GST-OmpA proteins in which select amino acids had been mutated to alanine (FIG. 10 and FIGS. 11, B and C). Many of the targeted residues were within OmpA amino acids 59 to 74. R32 and D53 were selected because they lie outside of residues 59 to 74, and, accordingly, it was anticipated that substituting them would not alter OmpA function. GST-OmpAK64A was considerably reduced in its ability to inhibit *A. phagocytophilum* infection (FIGS. 11, B and C), thereby indicating that this highly conserved residue was critical for GST-OmpA to serve as a competitive agonist. K65, however, was dispensable for this function, as the blocking ability of GST-OmpAK65A was uncompromised and the blocking ability of GST-OmpAKK6465AA was no greater than that of GST-OmpAK64. GST-OmpAG6IA displayed a modest but significant decline in its competitive agonist ability. Replacement of both G61 and K64 with alanines yielded an additive effect that was greater than substituting either residue alone, as GST OmpAGK6164AA was unable to inhibit infection. GST-OmpA proteins in which R32, D53, K60, E69 and E72 had been mutated to alanine were each unaffected in the ability to hinder infection.

Figure 11D:
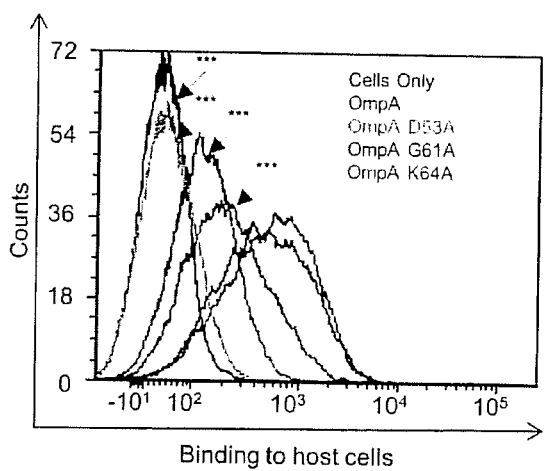

Given that K64 and G61 are vital and contributory, respectively, to the ability of recombinant OmpA to competitively inhibit *A. phagocytophilum* infection, it was evaluated if these residues mediate binding to mammalian host cell surfaces. RF/6A and HL-60 cells were incubated with His-tagged OmpA proteins. After unbound proteins were washed away, bound proteins were detected by flow cytometry using a His-tag antibody. His-tagged OmpA and OmpAD53A bound equally well to RF/6A cells (FIG. 11D). His-OmpAG61A bound poorly, His-OmpAK64A even more so, and His-OmpAGK6164AA could not bind to host cells. Collectively, these data are consistent with the invasin-receptor contacts predicted by the OmpA-sLe$^x$ docking models and underscore the importance of OmpA K64 and G61 to OmpA-receptor interactions.

Figure 12A:
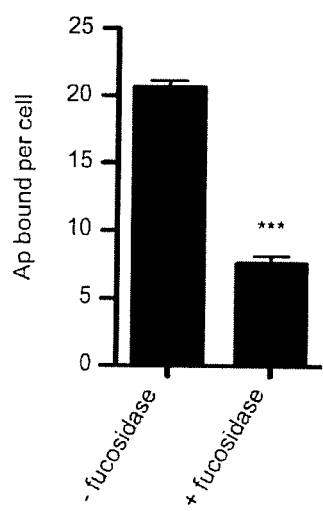
Figure 12B:
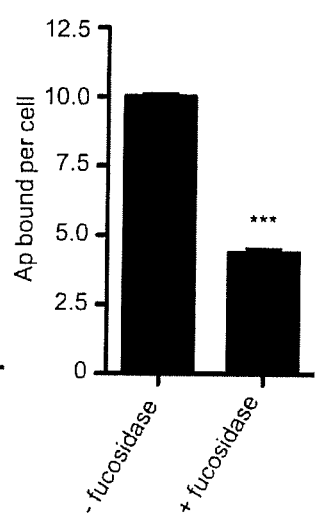
Figure 12C:
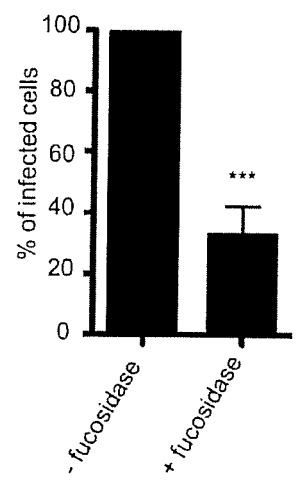

OmpA Interacts with α1,3-Fucose on Mammalian Host Cell Surfaces

α1,3-fucose is critical for *A. phagocytophilum* to bind PSGL-1-modeled glycopeptides, to bind and invade human and murine myeloid cells, and to establish infection in laboratory mice. Consistent with these observations, PSGL-1 CHO cells that had been pretreated with α1,3/4-fucosidase were approximately three-fold less permissive for *A. phagocytophilum* binding (FIG. 12A). Multiple lines of evidence led to the hypothesis that OmpA binds α1,3-fucose. First, OmpA binds α2,3-sialic acid, which is in close proximity to α1,3-fucose on sLe$^x$. Second, the docking model in FIG. 9E predicted that OmpA residues within the binding domain contact both α2,3-sialic acid and α1,3-fucose of sLe$^x$. Third, OmpA is important for *A. phagocytophilum* infection of not only myeloid, but also endothelial cells. Fourth, fucose residues are critical for the pathogen to invade RF/6A endothelial cells, as pretreatment of the host cells with α1,3/4-fucosidase made them significantly less permissive to *A. phagocytophilum* binding (FIG. 12B) and infection (FIG. 12C).

Figure 13A:
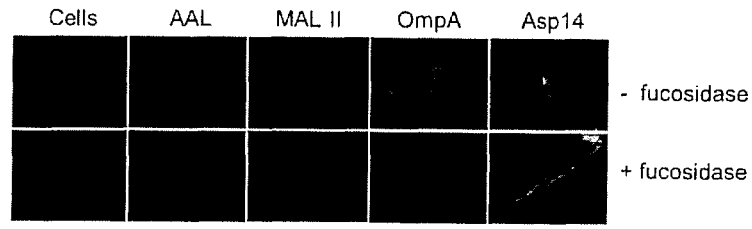
Figure 13B:
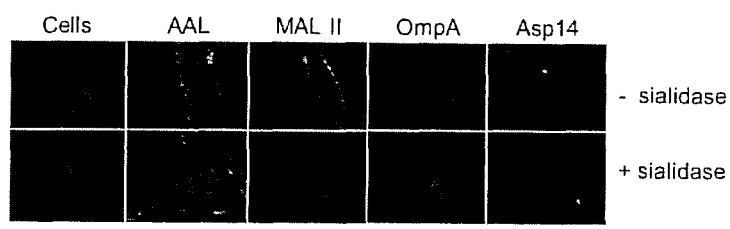
Figure 13C:
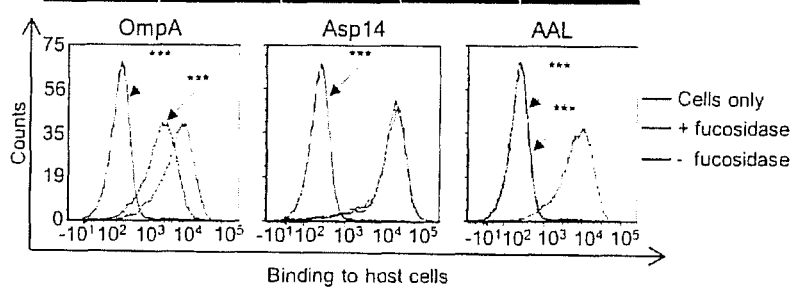
Figure 13D:
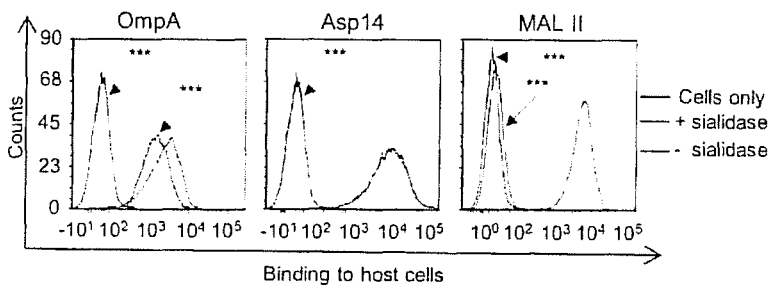
Figure 13E:
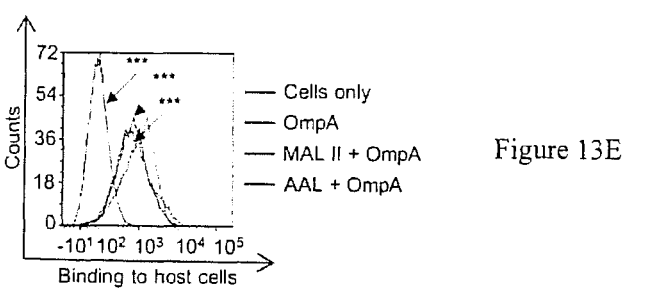

To determine if OmpA recognizes fucose, His-tagged OmpA was incubated with RF/6A cells that had been treated with α1,3/4-fucosidase and binding was assessed by immunofluorescence microscopy and flow cytometry. α2,3/6-sialidase-treated RF/6A cells were included as a positive control for a treatment that would make the host cells less permissive to recombinant OmpA binding. To verify the efficacy and specificity of both glycosidases, treated and untreated host cells were screened with AAL (*Aleuria aurantia* lectin) and MAL II (*Maackia amurensis* lectin II). AAL recognizes fucose residues that are in α1,3- and α1,6-linkages with N-acetylglucosamine (Yamashita et al., 1985; Chandrasekaran et al., 2003). MAL II detects sialic acids that are in α2,3-linkages with galactose. Fucosidase treatment abolished AAL but not MAL II binding, while sialidase treatment eliminated MAL II but not AAL binding (FIG. 13, A to D). Thus, the glycosidases were effective and specific. His-OmpA binding to both sialidase- and fucosidase-treated RF/6A cells was comparably reduced relative to vehicle control treated cells, while binding of His-Asp14 was unaffected. Incubating the host cells with MAL II or AAL prior to the addition of His-OmpA competitively reduced the efficiency of His-OmpA binding by similar degrees as sialidase or fucosidase, respectively (FIG. 13E). Overall, these observations demonstrate that optimal adhesion of OmpA to host cells involves both α2,3-sialic acid and α1,3-fucose and that Asp14 utilizes neither sialic acid nor fucose to bind to host cells.

OmpA Interacts with 6-Sulfo sLe$^x$ on RF/6A Endothelial Cell Surfaces

Because His-OmpA binding to RF/6A cells involved recognition of α2,3-sialic acid and α1,3-fucose (FIG. 13), it was hypothesized that OmpA interacts with sLe$^x$ or a sLe$^x$-like receptor on these host cells. sLe$^x$ and the sLe$^x$-like molecule, 6-sulfo sLe$^x$ (Neu5Ac(α2-3)Gal(β1-4)[Fuc(α1-3)][HSO3(3-6)]GcNAc1) (FIG. 14A) have both been detected on the surfaces of high endothelial venal, vascular, cancerous, and/or inflamed endothelial cells. To assess if either glycan is present on RF/6A cells, they were screened with sLe$^x$ antibodies, CSLEX1 and KM93 and the 6-sulfo-sLe$^x$ antibody, G72. Robust G72 signal but little to no CSLEX1 or KM93 signal was detected on RF/6A cells (FIGS. 14, B and C). Binding of His-OmpA to RF/6A cells that had been pretreated with G72 was pronouncedly reduced relative to cells that had been incubated with CSLEX1, KM93, or isotype control antibody (FIG. 14D). Thus, *A. phagocytophilum* OmpA recognizes 6-sulfo-sLe$^x$ on RF/6A endothelial cells.

OmpA-Coated Beads Bind to and are Internalized by Non-Phagocytic Endothelial Cells The ability of recombinant OmpA to bind to non-phagocytic RF/6A endothelial cells (FIGS. 12-14), suggests that, in addition to functioning as an invasin, it may also exhibit adhesin activity. Furthermore, while OmpA on the *A. phagocytophilum* surface acts cooperatively with Asp14 and AipA to mediate bacterial binding to and invasion of mammalian host cells, its ability to mediate these processes by itself is unknown. Therefore, the ability of recombinant OmpA to confer adhesiveness and invasiveness to inert particles was assessed. His-OmpA was coupled to fluorescent microspheres that were 1.0 μm in diameter, a size similar to that of the diameter of an *A. phagocytophilum* DC organism (0.8±0.2 μm). Successful conjugation of His-OmpA to the beads was confirmed by immunofluorescence using OmpA antiserum (FIG. 15A). RF/6A cells were incubated with recombinant OmpA-coated or non-coated control beads and screened with OmpA antibody to determine the numbers of beads bound per cell. To assess bead uptake, the cells were incubated for an additional 1 to 8 h and trypsin was used to remove non-internalized beads prior to screening. Immunofluorescence microscopy revealed that significantly more OmpA coated beads bound to and were internalized by RF/6A cells versus control beads (FIGS. 15, B and D). Scanning electron microscopy corroborated these results, as OmpA coated bead were observed bound to and inducing the formation of filopodia-like structures on the surfaces of RF/6A cells or covered by plasma membrane (FIG. 15C). Thus, OmpA alone was sufficient to mediate bead binding to and uptake by non-phagocytic RF/6A endothelial cells.

Binding and Uptake of OmpA-Coated Beads by Myeloid Cells is Dependent on sLe$^x$ Next the ability of His-OmpA coated beads to bind and enter HL-60 cells was assessed and, if so, whether these processes involve the OmpA myeloid cell receptor, sLe$^x$ Scanning electron microscopy revealed that OmpA beads bound to and induced their own uptake into HL-60 cells (FIG. 16A). Relative to the results obtained using RF/6A cells (FIG. 15D), OmpA coated bead binding to HL-60 cells was reduced (FIG. 16B). However, of the OmpA beads that did bind, approximately half of them were internalized (FIG. 16C). Approximately three-fold fewer control beads than OmpA coated beads bound to and were taken in (FIGS. 16, B and C). OmpA bead uptake, but not adherence was pronouncedly inhibited when the assay was performed at 4° C. versus 37° C. Beads coated with OmpAG61A, OmpAK64A, OmpAGK6164AA, and OmpAKK6465AA were significantly compromised in their abilities to bind to and be internalized by HL-60 cells (FIGS. 16, B and C). OmpA bead cellular adherence and entry were significantly inhibited and neutralized, respectively, for host cells that had been pretreated with α2,3/6-sialidase or α1,3/4-fucosidase (FIGS. 16, D and E). Moreover, the sLe$^x$-specific antibody, CSLEX1 significantly reduced binding and blocked internalization of OmpA beads into HL-60 cells (FIGS. 16, F and G). KPL-1, an antibody that is specific for and blocks A. phagocytophilum binding to the PSGL-1 N-terminus, did not affect OmpA bead adherence or uptake (FIGS. 16, H and I). These data indicate that OmpA coated beads bind and enter myeloid cells in a sLe$^x$-dependent manner and require OmpA residues G61 and K64 to optimally do so.

Delineation of the Asp14 Binding Domain

Figure 17A:
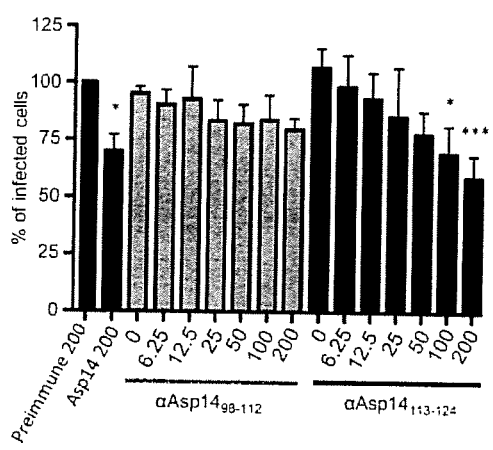
Figure 17B:
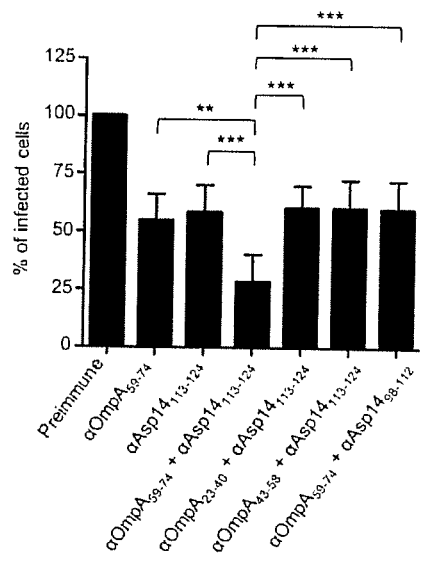
Figure 17C:
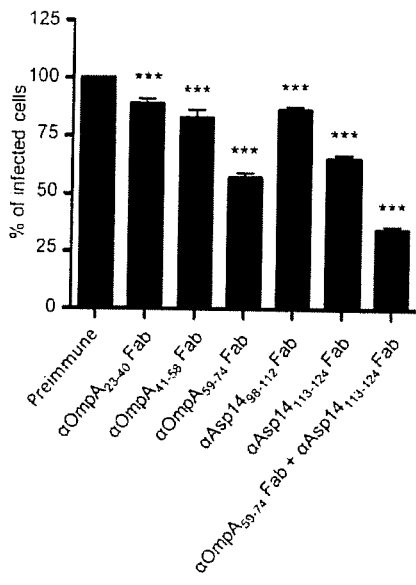
Figure 17D:
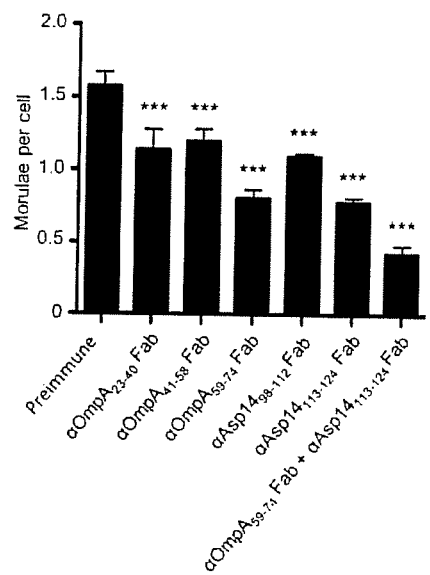

Of the three invasins that cooperatively function to facilitate A. phagocytophilum infection of mammalian host cells, only the binding domain of Asp14 had yet to be defined. Asp14 is a 124-amino acid (13.8 kDa) protein, and its binding domain lies within residues 101 to 124. To further narrow down this region, antisera were raised against residues 98 to 112 and 113 to 124. Both antisera recognized GST-Asp14, but not GST-Asp141-88 or GST alone. Also, antiserum targeting Asp1498-112 but not Asp14113-124 detected GST-Asp141-112 and each antiserum was specific for the peptide against which it had been raised. Next, the abilities of anti-Asp1498-112 and anti-Asp14113-124 to inhibit A. phagocytophilum infection of HL-60 cells were assessed. Incubating DC bacteria with Asp14113-124 antibody reduced the percentages of infected cells in a dose dependent manner, whereas Asp1498-112 antibody had no effect (FIG. 17A). When used together, antisera against Asp14113-124 and OmpA59-74 reduced A. phagocytophilum by approximately four-fold (FIG. 17B). The observed blocking effect was significantly greater than that achieved with either antiserum alone or when either was paired with antisera that targeted irrelevant regions of OmpA or Asp14. To ensure that the blocking effects achieved by the OmpA59-74 and Asp14113-124 antisera were specific, fragment antigen binding (Fab fragment) portions of OmpA23-40, OmpA41-48, OmpA59-74, Asp1498-112, Asp14113-124, or OmpA59-74 and Asp14113-124 antibodies were prepared and assessed for the ability to inhibit A. phagocytophilum infection of HL-60 cells. Consistent with results obtained using intact antibodies, OmpA59-74 Fab, Asp14113-124 Fab, and the combination thereof achieved the greatest reductions in the percentage of infected cells and morulae per cell (FIGS. 17, C and D).

An Antisera Combination Targeting the OmpA, Asp14, and AipA Binding Domains Pronouncedly Inhibits A. phagocytophilum Infection of Host Cells It was shown in Example 1 that a combination of antisera that had been raised against the entireties of OmpA, AipA, and Asp14 strongly inhibited A. phagocytophilum infection of mammalian host cells. To refine this blocking approach, DC organisms were treated with a cocktail of antibodies specific for OmpA59-74, Asp14113-124, and AipA9-21 prior to incubating the bacteria with HL-60 cells. This antibody combination significantly attenuated infection, reducing the percentage of infected cells and number of morulae per cell by approximately five-fold (FIGS. 18, A and B). The reduction in infection achieved using the combination antisera was due to effective blocking of bacterial adhesion to HL-60 cell surfaces, as combination antisera specific for OmpA59-74, Asp14113-124, and AipA9-21 reduced the numbers of bound A. phagocytophilum organisms per cell by more than four-fold relative to the same amount of preimmune serum (FIG. 18C). The observed reductions in bacterial adhesion and infection achieved by targeting all three binding domains were greater than those achieved using (1) antibodies that targeted only one or two of the binding domains and (2) combinations of antibodies against one or two of the binding domains together with antibodies against irrelevant portions of OmpA, Asp14, or AipA. Thus, targeting the OmpA, Asp14, and AipA binding domains together produced a synergistic blocking effect that protects host cells from A. phagocytophilum infection.

Discussion

This study identified the OmpA and Asp14 binding domains and defined the OmpA residues that are critical for adhesion and invasion. The OmpA binding domain lies within amino acids 59 to 74 and it, like the rest of the protein, is highly conserved among A. phagocytophilum strains known to cause disease in humans and animals. Antibody against OmpA59-74 inhibited bacterial binding to PSGL-1 CHO cells and infection of HL-60 cells. OmpA59-74 is predicted to be a solvent exposed alpha helix and part of a cationic surface patch that binds sLe$^x$, an interaction that is similar to those between staphylococcal superantigen-like (SSL) protein family members and sLe$^x$. SSL4, SSL5, and SSL11 each use basic residues within cationic surface pockets to interact with α2,3-sialic acid of sLe$^x$ (Chung et al., 2007; Hermans et al., 2012; Baker et al., 2007). Likewise, other pathogens' sialic acid binding proteins, including uropathogenic Escherichia coli sialic acid-specific S fimbrial adhesin (Morschhauser et al., 1990), pertussis toxin of Bordetella pertussis (Stein et al., 1994), influenza viral neuraminidase (Varghese et al., 1992), canine adenovirus 2 capsid protein (Rademacher et al., 2012), and rhesus rotovirus VP4 (Dormitzer et al., 2002) all use basic residues localized within cationic surface pockets to target sialic acid. The Asp14 binding domain is within amino acids 113 to 124. Antibody specific for Asp14113-124 abrogated bacterial binding and infection of host cells. As Asp14 bears no semblance to any known crystal structure, it could not be modeled. However, from the data presented herein it can be inferred that Asp14 amino acids 113 to 124 are exposed on the surfaces of A. phagocytophilum and the invasin itself.

OmpA K64 is essential for and G61 contributes to the ability of OmpA to bind to mammalian host cells. These experimental findings support the top two OmpA-sLe$^x$ docking models, both of which predicted the involvement of K64 and G61 in interacting with α2,3-sialic acid and α1,3-fucose of sLe$^x$. The actual interactions between OmpA and sLe$^x$ are likely a hybrid of those predicted by the two docking models because, while both predicted the involvement of K64 and G61, one also predicted the involvement of K60, which was found to be negligible for OmpA to act as a competitive agonist. OmpA K64 and G61 may play functionally conserved roles among members of the family Anaplasmataceae and the genus *Anaplasma*. K64 is present in all *Anaplasma* and *Ehrlichia* spp. OmpA proteins, while G61 is conserved among *Anaplasma* but not *Ehrlichia* spp. OmpA proteins. *A. marginale* agglutinates bovine red blood cells in a sialidase-sensitive manner, indicating that it interacts with sialylated glycans on erythrocyte surfaces. *E. chaffeensis* OmpA contributes to infection of monocytic cells (Cheng et al., 2011). Compared to the conservation exhibited among *Anaplasma* spp. OmpA proteins, *A. phagocytophilum* and *E. chaffeensis* OmpA proteins are more divergent in sequence, especially in the binding domain, which may contribute to these pathogens' tropisms for different leukocytes. Still, because of its conservation, the *E. chaffeensis* OmpA residue that corresponds to *A. phagocytophilum* OmpA K64 may be involved in binding to a sLe$^x$-related glycan on monocytic cells.

Together with α2,3-sialic acid, α1,3-fucose is critical for *A. phagocytophilum* binding and infection. OmpA binds α1,3-fucose, as can be inferred from the observations that recombinant OmpA bound poorly to RF/6A endothelial cells from which α1,3/4-fucose residues had been removed or that had been incubated with the α1,3/6-fucose-specific lectin, AAL. The ability of OmpA to bind α2,3-sialic acid and α1,3-fucose is consistent with the close proximity of the two sugar residues to each other in sLe$^x$ and related glycans and also with OmpA-sLe$^x$ molecular docking predictions. Yet, RF/6A cells, which support *A. phagocytophilum* binding and infection, express very little to no sLe$^x$. Rather, they express 6-sulfo-sLe$^x$, which presents α2,3-sialic acid and α1,3-fucose in the same orientation and proximity to each other as sLe$^x$. Recombinant OmpA binding to RF/6A cells was significantly reduced in the presence of 6-sulfo-sLe$^x$ antibody, but not sLe$^x$ antibodies, thereby supporting that 6-sulfo-sLe$^x$ is an *A. phagocytophilum* receptor on these cells. Thus, *A. phagocytophilum* OmpA interacts with glycans that present α2,3-sialic acid and α1,3-fucose in a similar manner as sLe$^x$.

OmpA by itself functions as both an adhesin and an invasin, as demonstrated by the ability of His-OmpA to confer adhesive and internalization capabilities to inert beads. Approximately half of the His-OmpA beads that bound to host cells were internalized, a degree of uptake that was similar to that reported for *C. burnetii* OmpA coated beads (Martinez et al., 2014). Twenty-fold more OmpA coated beads bound to RF/6A cells than to HL-60 cells. Similarly, recombinant OmpA binding to RF/6A cells but not to HL-60 cells could be detected by immunofluorescence microscopy and flow cytometry. Nonetheless, the ability of recombinant OmpA to competitively antagonize *A. phagocytophilum* binding and infection of HL-60 cells demonstrates its ability to bind to the host cells, but it apparently does so at too low an avidity to remain bound during the wash steps associated with sample preparation for the detection methods used. The observed differences in OmpA binding to HL-60 versus RF/6A cells could be due to differences in the levels of sLe$^x$ and 6-sulfo-sLe$^x$ on HL-60 and RF/6A cell surfaces or perhaps due to the presence of an additional, undefined OmpA receptor on RF/6A cells. Yet another possibility is that the bacterium binds with a greater avidity to 6-sulfo-sLe$^x$ than to sLe$^x$.

Because of the essential and cooperative roles that OmpA, Asp14, and AipA play in the *A. phagocytophilum* lifecycle, blocking their ability to function prevents both infection and bacterial survival. Moreover, directing the immune response to their binding domains enhances protective efficacy. In this study, an antibody cocktail specific for the OmpA, Asp14, and AipA binding domains blocked *A. phagocytophilum* infection of host cells. The relevance of this work extends to other obligate intracellular pathogens that use multiple invasins, including *A. marginale, E. chaffeensis*, spotted fever rickettsiae, *Chlamydia* spp., *Mycobacterium* spp., and *Orientia tsutsugamushi*, as their survival hinges on their abilities to enter host cells.

REFERENCES

Aguero-Rosenfeld M E, Donnarumma L, Zentmaier L, Jacob J, Frey M, et al. (2002) Seroprevalence of antibodies that react with *Anaplasma* phagocytophila, the agent of human granulocytic ehrlichiosis, in different populations in Westchester County, N.Y. J Clin Microbiol 40: 2612-2615.

Alhumaidan, H., Westley, B., Esteva, C., Berardi, V., Young, C. and Sweeney, J. (2013). Transfusion-transmitted anaplasmosis from leukoreduced red blood cells. *Transfusion* 53, 181-186.

Al-Khedery B, Lundgren A M, Stuen S, Granquist E G, Munderloh U G, et al. (2012) Structure of the type IV secretion system in different strains of *Anaplasma phagocytophilum*. BMC Genomics 13: 678.

Annen, K., Friedman, K., Eshoa, C., Horowitz, M., Gottschall, J. and Straus, T. (2012). Two cases of transfusion-transmitted *Anaplasma phagocytophilum. American journal of clinical pathology* 137, 562-565.

Anton B P, Raleigh 858 EA (2004) Transposon-mediated linker insertion scanning mutagenesis of the *Escherichia coli* McrA endonuclease. J Bacteriol 186: 5699-5707.

Baker H M, Basu I, Chung M C, Caradoc-Davies T, Fraser J D, et al. (2007) Crystal structures of the staphylococcal toxin SSL5 in complex with sialyl Lewis X reveal a conserved binding site that shares common features with viral and bacterial sialic acid binding proteins. J Mol Biol 374: 1298-1308.

Bakken J S, Goellner P, Van Etten M, Boyle D Z, Swonger O L, et al. (1998) Seroprevalence of human granulocytic ehrlichiosis among permanent residents of northwestern Wisconsin. Clin Infect Dis 27: 1491-1496.

Barbosa, A. S., Abreu, P. A., Neves, F. O., Atzingen, M. V., Watanabe, M. M., Vieira, M. L., et al. (2006). A newly identified leptospiral adhesin mediates attachment to laminin. *Infection and immunity* 74, 6356-6364.

Bastidas R J, Elwell C A, Engel J N, Valdivia R H (2013) Chlamydial intracellular survival strategies. Cold Spring Harb Perspect Med 3: a010256.

Brennan, M. J. and Shahin, R. D. (1996). Pertussis antigens that abrogate bacterial adherence and elicit immunity. *American journal of respiratory and critical care medicine* 154, S 145-149.

Cardwell, M. M. and Martinez, J. J. (2009). The Sca2 autotransporter protein from *Rickettsia conorii* is sufficient to mediate adherence to and invasion of cultured mammalian cells. *Infection and immunity* 77, 5272-5280.

Carlyon, J. A. (2012) Establishing intracellular infection: modulation of host cell functions (Anaplasmataceae). In Intracellular Pathogens II Rickettsiales, G. H. Palmer, A. Azad (eds.). Washington, D.C., ASM Press.

Carlyon, J. A., Akkoyunlu, M., Xia, L., Yago, T., Wang, T., Cummings, R. D., et al. (2003). Murine neutrophils require alpha1,3-fucosylation but not PSGL-1 for productive infection with *Anaplasma phagocytophilum*. *Blood* 102, 3387-3395.

Carlyon J A, Chan W T, Galan J, Roos D, Fikrig E (2002) Repression of rac2 mRNA expression by *Anaplasma phagocytophilum* is essential to the inhibition of superoxide production and bacterial proliferation. J Immunol 169: 7009-7018.

Centers for Disease Control and Prevention (2013). Notice to readers: final 2012 reports of nationally notifiable infectious diseases. *MMWR. Morbidity and mortality weekly report* 62, 669-682.

Chan, Y. G., Cardwell, M. M., Hermanas, T. M., Uchiyama, T. and Martinez, J. J. (2009). Rickettsial outer-membrane protein B (rOmpB) mediates bacterial invasion through Ku70 in an actin, c-Cbl, clathrin and caveolin 2-dependent manner. *Cellular microbiology* 11, 629-644.

Chan, Y. G., Riley, S. P. and Martinez, J. J. (2010). Adherence to and invasion of host cells by spotted Fever group *rickettsia* species. *Frontiers in microbiology* 1, 139.

Chandrasekaran E V, Chawda R, Rhodes J M, Locke R D, Piskorz C F, et al. (2003) The binding characteristics and utilization of *Aleuria aurantia, Lens culinaris* and few other lectins in the elucidation of fucosyltransferase activities resembling cloned FT VI and apparently unique to colon cancer cells. Carbohydr Res 338: 887-901.

Chang, A., Kaur, R., Michel, L. V., Casey, J. R. and Pichichero, M. (2011). *Haemophilus influenzae* vaccine candidate outer membrane protein P6 is not conserved in all strains. *Human vaccines* 7, 102-105.

Chang, B., Kura, F., Amemura-Maekawa, J., Koizumi, N. and Watanabe, H. (2005). Identification of a novel adhesion molecule involved in the virulence of *Legionella pneumophila*. Infection and immunity 73, 4272-4280.

Cheng Z, Miura K, Popov V L, Kumagai Y, Rikihisa Y (2011) Insights into the CtrA regulon in development of stress resistance in obligatory intracellular pathogen *Ehrlichia chaffeensis*. Mol Microbiol 82: 1217-1234

Chung M C, Wines B D, Baker H, Langley R J, Baker E N, et al. (2007) The crystal structure of staphylococcal superantigen-like protein 11 in complex with sialyl Lewis X reveals the mechanism for cell binding and immune inhibition. Mol Microbiol 66: 1342-1355.

Cirillo, S. L., Benrudez, L. E., El-Etr, S. H., Duhamel, G. E. and Cirillo, J. D. (2001). *Legionella pneumophila* entry gene rtxA is involved in virulence. *Infection and immunity* 69, 508-517.

Dicko, A., Odusanya, O. O., Diallo, A. I., Santara, G., Barry, A., Dolo, A., et al. (2011). Primary vaccination with the 10-valent pneumococcal non-typeable *Haemophilus influenzae* protein D conjugate vaccine (PHiD-CV) in infants in *Mali* and Nigeria: a randomized controlled trial. *BMC public health* 11, 882.

Dormitzer P R, Sun Z Y, Wagner 814 G, Harrison S C (2002) The rhesus rotavirus VP4 sialic acid binding domain has a galectin fold with a novel carbohydrate binding site. EMBO J 21: 885-897.

Duncan, C., Prashar, A., So, J., Tang, P., Low, D. E., Terebiznik, M. and Guyard, C. (2011). Lcl of *Legionella pneumophila* is an immunogenic GAG binding adhesin that promotes interactions with lung epithelial cells and plays a crucial role in biofilm formation. *Infection and immunity* 79, 2168-2181.

Emini, E. A., Hughes, J. V., Perlow, D. S. and Boger, J. (1985). Induction of hepatitis A virus-neutralizing antibody by a virus-specific synthetic peptide. *J Virol* 55, 836-839.

Fukuda M, Spooncer E, Oates J E, Dell A, Klock J C (1984) Structure of sialylated fucosyl lactosaminoglycan isolated from human granulocytes. J Biol Chem 259: 10925-10935.

Garduno, R. A., Garduno, E. and Hoffman, P. S. (1998). Surface-associated hsp60 chaperonin of *Legionella pneumophila* mediates invasion in a HeLa cell model. *Infection and immunity* 66, 4602-4610.

Ge, Y. and Rikihisa, Y. (2007). Identification of novel surface proteins of *Anaplasma phagocytophilum* by affinity purification and proteomics. *Journal of bacteriology* 189, 7819-7828.

Giufre, M., Carattoli, A., Cardines, R., Mastrantonio, P. and Cerquetti, M. (2008). Variation in expression of HMW1 and HMW2 adhesins in invasive nontypeable *Haemophilus influenzae* isolates. *BMC microbiology* 8, 83.

Goodman, J. L., Nelson, C. M., Klein, M. B., Hayes, S. F. and Weston, B. W. (1999). Leukocyte infection by the granulocytic ehrlichiosis agent is linked to expression of a selectin ligand. *The Journal of clinical investigation* 103, 407-412.

Goodman J L, Nelson C, Vitale B, Madigan J E, Dumler J S, et al. (1996) Direct cultivation of the causative agent of human granulocytic ehrlichiosis. N Engl J Med 334: 209-215.

Grande K K, Gustin J K, Kessler E, Ohman D E (2007) Identification of critical residues in the propeptide of LasA protease of *Pseudomonas aeruginosa* involved in the formation of a stable mature protease. J Bacteriol 189: 3960-3968.

Gribble D H (1969) Equine ehrlichiosis. J Am Vet Med Assoc 155: 462-469.

Grimm, D., Tilly, K., Byram, R., Stewart, P. E., Krum, J. G., Bueschel, D. M., et al. (2004). Outer-surface protein C of the Lyme disease spirochete: a protein induced in ticks for infection of mammals. *Proceedings of the National Academy of Sciences of the United States of America* 101, 3142-3147.

Hao Q, Geng Z, Hou X X, Tian Z, Yang X J, et al. (2013) Seroepidemiological investigation of lyme disease and human granulocytic anaplasmosis among people living in forest areas of eight provinces in China. Biomed Environ Sci 26:185-189.

Hermans S J, Baker H M, Sequeira R P, Langley R J, Baker E N, et al. (2012) Structural and functional properties of staphylococcal superantigen-like protein 4. Infect Immun 80: 4004-4013.

Herron, M. J., Nelson, C. M., Larson, J., Snapp, K. R., Kansas, G. S. and Goodman, J. L. (2000). Intracellular parasitism by the human granulocytic ehrlichiosis bacterium through the P-selectin ligand, PSGL-1. *Science* 288, 1653-1656.

Hinnebusch, B. J., Perry, R. D. and Schwan, T. G. (1996). Role of the *Yersinia pestis* hemin storage (hms) locus in the transmission of plague by fleas. *Science* 273, 367-370.

Hofmann, K. and Stoffel, W. (1993). TMbase—A database of membrane spanning proteins segments. Biol. Chem. Hoppe-Seyler 374, 166.

Hopkins, R. S., Jajosky, R. A., Hall, P. A., Adams, D. A., Connor, F. J., Sharp, P., Anderson, W. J., Fagan, R. F., Aponte, J. J., Nitschke, D. A., Worsham, C. A., Adekoya, N. and Chang, M. H. (2005) Summary of notifiable diseases-United States, 2003. MAIVR Morbity and mortality weekly report 52, 1-85.

Huang, B., Hubber, A., McDonough, J. A., Roy, C. R., Scidmore, M. A. and Carlyon, J. A. (2010a). The *Anaplasma phagocytophilum*-occupied vacuole selectively recruits Rab-GTPases that are predominantly associated with recycling endosomes. *Cellular microbiology* 12, 1292-1307.

Huang, B., Troese, M. J., Howe, D., Ye, S., Sims, J. T., Heinzen, R. A., et al. (2010b). *Anaplasma phagocytophilum* APH_0032 is expressed late during infection and localizes to the pathogen-occupied vacuolar membrane. Microbialpathogenesis 49, 273-284.

Huang, B., Ojogun, N., Ragland, S. A. and Carlyon, J. A. (2012) Monoubiquitinated proteins decorate the *Anaplasma phagocytophilum*-occupied vacuolar membrane. *FEMS Immunology and Medical Microbiology* 64, 32-41.

Jalalvand, F., Su, Y. C., Morgelin, M., Brant, M., Hallgren, O., Westergren-Thorsson, G., et al. (2013). *Haemophilus influenzae* protein F mediates binding to laminin and human pulmonary epithelial cells. *The Journal of infectious diseases* 207, 803-813.

Jereb, M., Pecaver, B., Tomazic, J., Muzlovic, I., Avsic-Zupanc, T., Premru-Srsen, T., et al. (2012). Severe human granulocytic anaplasmosis transmitted by blood transfusion. *Emerging infectious diseases* 18, 1354-1357.

Johnson R C, Kodner C, Jarefeld J, Eck D K, Xu Y (2011) Agents of human anaplasmosis and Lyme disease at Camp Ripley, Minn. Vector Borne Zoonotic Dis 11: 1529-1534.

Jurcisek, J. A., Bookwalter, J. E., Baker, B. D., Fernandez, S., Novotny, L. A., Munson, R. S., Jr. and Bakaletz, L. O. (2007). The PiA protein of non-typeable *Haemophilus influenzae* plays a role in biofilm formation, adherence to epithelial cells and colonization of the mammalian upper respiratory tract. Molecular microbiology 65, 1288-1299.

Kahlon, A., Ojogun, N., Ragland, S. A., Seidman, D., Troese, M. J., Ottens, A. K., et al. (2013). *Anaplasma phagocytophilum* Asp14 is an invasin that interacts with mammalian host cells via its C terminus to facilitate infection. *Infection and immunity* 81, 65-79.

Karakantza M, Gibson F M, Cavenagh J D, Ball S E, Gordon M Y, et al. (1994) SLe(x) expression of normal CD34 positive bone marrow haemopoietic progenitor cells. Br J Haematol 86: 883-886.

Kelley L A, Sternberg M J (2009) Protein structure prediction on the Web: a case study using the Phyre server. Nat Protoc 4: 363-371.

Kolbert C P, Bruinsma E S, Abdulkarim A S, Hofineister E K, Tompkins R B, et al. (1997) Characterization of an immunoreactive protein from the agent of human granulocytic ehrlichiosis. J Clin Microbiol 35: 1172-1178.

Krogh, A., Larsson, B., von Heijne, G. and Sonnhammer, E. L. (2001). Predicting transmembrane protein topology with a hidden Markov model: application to complete genomes. *Journal of molecular biology* 305, 567-580.

Kyte, J. and Doolittle, R. F. (1982). A simple method for displaying the hydropathic character of a protein. *Journal of molecular biology* 157, 105-132.

Li F, Wilkins P P, Crawley S, Weinstein J, Cummings R D, et al. (1996) Post translational modifications of recombinant P-selectin glycoprotein ligand-1 required for binding to P- and E-selectin. The Journal of biological chemistry 271: 3255-3264.

Livak, K. J. and Schmittgen, T. D. (2001). Analysis of relative gene expression data using real-time quantitative PCR and the 2(-Delta Delta C(T)) Method. Methods 25, 402-408.

Madigan J E, Gribble D (1987) Equine ehrlichiosis in northern California: 49 cases (1968-1981). J Am Vet Med Assoc 190: 445-448.

Mansueto P, Vitale G, Cascio A, Seidita A, Pepe I, et al. (2012) New insight into immunity and immunopathology of Rickettsial diseases. Clin Dev Immunol 2012: 967852.

Martinez E, Cantet F, Fava L, Norville I, Bonazzi M (2014) Identification of OmpA, a *Coxiella burnetii* Protein Involved in Host Cell Invasion, by Multi-Phenotypic High-Content Screening. PLoS Pathog 10: e1004013

Martinez, J. J. and Cossart, P. (2004). Early signaling events involved in the entry of *Rickettsia* conorii into mammalian cells. *Journal of cell science* 117, 5097-5106.

Massung R F, Levin M L, Munderloh U G, Silverman D J, Lynch M J, et al. (2007) Isolation and propagation of the Ap-Variant 1 strain of *Anaplasma phagocytophilum* in a tick cell line. J Clin Microbiol 45: 2138-2143.

Mastronunzio, J. E., Kurscheid, S. and Fikrig, E. (2012). Postgenomic analyses reveal development of infectious *Anaplasma phagocytophilum* during transmission from ticks to mice. *Journal of bacteriology* 194, 2238-2247.

Miller D P, McDowell J V, Bell J K, Marconi R T (2011) Crystallization of the factor H-binding protein, FhbB, from the periopathogen *Treponema denticola*. Acta Crystallogr Sect F Struct Biol Cryst Commun 67: 678-681.

Minnick M F, Raghavan R (2012) Developmental biology of *Coxiella burnetii*. Adv Exp Med Biol 984: 231-248.

Molleken, K., Becker, E. and Hegemann, J. H. (2013). The *Chlamydia pneumoniae* invasin protein Pmp21 recruits the EGF receptor for host cell entry. *PLoS pathogens* 9, e1003325.

Molleken, K., Schmidt, E. and Hegemann, J. H. (2010). Members of the Pmp protein family of *Chlamydia pneumoniae* mediate adhesion to human cells via short repetitive peptide motifs. *Molecular microbiology* 78, 1004-1017.

Morschhauser J, Hoschutzky H, Jann K, Hacker J (1990) Functional analysis of the sialic acid-binding adhesin SfaS of pathogenic *Escherichia coli* by site-specific mutagenesis. Infect Immun 58: 2133-2138.

Nelson, C. M., Herron, M. J., Felsheim, R. F., Schloeder, B. R., Grindle, S. M., Chavez, A. O., et al. (2008). Whole genome transcription profiling of *Anaplasma phagocytophilum* in human and tick host cells by tiling array analysis. *BMC Genomics* 9, 364.

Ojogun N, Barnstein B, Huang B, Oskeritzian C A, Homeister J W, et al. (2011) *Anaplasma phagocytophilum* infects mast cells via alpha1,3-fucosylated but not sialylated glycans and inhibits IgE-mediated cytokine production and histamine release. Infect Immun 79: 2717-2726.

Ojogun, N., Kahlon, A., Ragland, S. A., Troese, M. J., Mastronunzio, J. E., Walker, N.J., et al. (2012). *Anaplasma phagocytophilum* outer membrane protein A interacts with sialylated glycoproteins to promote infection of mammalian host cells. *Infection and immunity* 80, 3748-3760.

Okoye M E, Sexton G L, Huang E, McCaffery J M, Desai P (2006) Functional analysis of the triplex proteins (VP19C and VP23) of herpes simplex virus type 1. J Virol 80: 929-940.

Park, J., Kim, K. J., Grab, D. J. and Dumler, J. S. (2003). *Anaplasma phagocytophilum* major surface protein-2 (Msp2) fonns multimeric complexes in the bacterial membrane. *FEMS microbiology letters* 227, 243-247.

Perry, R. D. and Fetherston, J. D. (1997). *Yersinia pestis*—etiologic agent of plague. *Clin Microbiol Rev* 10, 35-66.

Pinne, M., Choy, H. A. and Haake, D. A. (2010). The OmpL37 surface-exposed protein is expressed by pathogenic *Leptospira* during infection and binds skin and vascular elastin. *PLoS neglected tropical diseases* 4, e815.

Rademacher C, Bru T, McBride R, Robison E, Nycholat C M, et al. (2012) A Siglec like sialic-acid-binding motif revealed in an adenovirus capsid protein. Glycobiology 22: 1086-1091.

Reneer, D. V., Kearns, S. A., Yago, T., Sims, J., Cummings, R. D., McEver, R. P. and Carlyon, J. A. (2006). Characterization of a sialic acid- and P-selectin glycoprotein ligand-1-independent adhesin activity in the granulocytotropic bacterium *Anaplasma phagocytophilum*. *Cellular microbiology* 8, 1972-1984.

Reneer, D. V., Troese, M. J., Huang, B., Kearns, S. A. and Carlyon, J. A. (2008). *Anaplasma phagocytophilum* PSGL-1-independent infection does not require Syk and leads to less efficient AnkA delivery. *Cellular microbiology* 10, 1827-1838.

Rikihisa Y, Zhi N, Wormser G P, Wen B, Horowitz H W, et al. (1997) Ultrastructural and antigenic characterization of a granulocytic ehrlichiosis agent directly isolated and stably cultivated from a patient in New York state. J Infect Dis 175: 210-213.

Riley, S. P., Goh, K. C., Hermanas, T. M., Cardwell, M. M., Chan, Y. G. and Martinez, J. J. (2010). The *Rickettsia conorii* autotransporter protein Sca1 promotes adherence to nonphagocytic mammalian cells. *Infection and immunity* 78, 1895-1904.

Sarkar, M., Reneer, D. V. and Carlyon, J. A. (2007). Sialyl-Lewis x-independent infection of human myeloid cells by *Anaplasma phagocytophilum* strains HZ and HGE1. *Infection and immunity* 75, 5720-5725.

Seidman D, Ojogun N, Walker N J, Mastronunzio J, Kahlon A, et al. (2014) *Anaplasma phagocytophilum* surface protein AipA mediates invasion of mammalian host cells. Cell Microbiol 16: 1133-1145.

Singh, B., Al-Jubair, T., Morgelin, M., Thunnissen, M. M. and Riesbeck, K. (2013). The unique structure of *Haemophilus influenzae* protein E reveals multiple binding sites for host factors. *Infection and immunity* 81, 801-814.

Sperandio M (2006) Selectins and glycosyltransferases in leukocyte rolling in vivo. FEBS J 273: 4377-4389.

Stein P E, Boodhoo A, Armstrong G D, Heerze L D, Cockle S A, et al. (1994) Structure of a pertussis toxin-sugar complex as a model for receptor binding. Nat Struct Biol 1: 591-596.

Stone, B. J. and Abu Kwaik, Y. (1998). Expression of multiple pili by *Legionella pneumophila*: identification and characterization of a type IV pilin gene and its role in adherence to mammalian and protozoan cells. *Infection and immunity* 66, 1768-1775.

Stuen S, Granquist E G, Silaghi C (2013) *Anaplasma phagocytophilum*—a widespread multi-host pathogen with highly adaptive strategies. Front Cell Infect Microbiol 3: 31.

Suarez C E, Noh S (2011) Emerging perspectives in the research of bovine babesiosis and anaplasmosis. Vet Parasitol 180: 109-125.

Symington F W, Hedges D L, Hakomori S (1985) Glycolipid antigens of human polymorphonuclear neutrophils and the inducible HL-60 myeloid leukemia line. J Immunol 134: 2498-2506.

Tilly, K., Krum, J. G., Bestor, A., Jewett, M. W., Grimm, D., Bueschel, D., et al. (2006). *Borrelia burgdorferi* OspC protein required exclusively in a crucial early stage of mammalian infection. *Infection and immunity* 74, 3554-3564.

Troese, M. J. and Carlyon, J. A. (2009). *Anaplasma phagocytophilum* dense-cored organisms mediate cellular adherence through recognition of human P-selectin glycoprotein ligand 1. *Infection and immunity* 77, 4018-4027.

Troese, M. J., Kahlon, A., Ragland, S. A., Ottens, A. K., Ojogun, N., Nelson, K. T., et al. (2011). Proteomic analysis of *Anaplasma phagocytophilum* during infection of human myeloid cells identifies a protein that is pronouncedly upregulated on the infectious dense-cored cell. *Infection and immunity* 79, 4696-4707.

Truchan, H. K., Seidman, D. and Carlyon, J. A. (2013). Breaking in and grabbing a meal: *Anaplasma phagocytophilum* cellular invasion, nutrient acquisition, and promising tools for their study. *Microbes and infection/Institut Pasteur*.

Vandersmissen, L., De Buck, E., Saels, V., Coil, D. A. and Anne, J. (2010). A *Legionella pneumophila* collagen-like protein encoded by a gene with a variable number of tandem repeats is involved in the adherence and invasion of host cells. FEMS Microbiol Lett 306, 168-176.

Varghese J N, McKimm-Breschkin J L, Caldwell J B, Kortt A A, Colman P M (1992) The structure of the complex between influenza virus neuraminidase and sialic acid, the viral receptor. Proteins 14: 327-332.

Verma, A., Brissette, C. A., Bowman, A. A., Shah, S. T., Zipfel, P. F. and Stevenson, B. (2010). Leptospiral endostatin-like protein A is a bacterial cell surface receptor for human plasminogen. *Infection and immunity* 78, 2053-2059.

Wang, Y., Berg, E. A., Feng, X., Shen, L., Smith, T., Costello, C. E. and Zhang, Y. X. (2006). Identification of surface-exposed components of MOMP of *Chlamydia trachomatis* serovar F. *Protein science: a publication of the Protein Society* 15, 122-134.

Xia, L., Ramachandran, V., McDaniel, J. M., Nguyen, K. N., Cummings, R. D. and McEver, R. P. (2003). N-terminal residues in murine P-selectin glycoprotein ligand-1 required for binding to murine P-selectin. *Blood* 101, 552-559.

Yago, T., Leppanen, A., Carlyon, J. A., Akkoyunlu, M., Karmakar, S., Fikrig, E., et al. (2003). Structurally distinct requirements for binding of P-selectin glycoprotein ligand-1 and sialyl Lewis x to *Anaplasma phagocytophilum* and P-selectin. *The Journal of biological chemistry* 278, 37987-37997.

Yamashita K, Kochibe N, Ohkura T, Ueda I, Kobata A (1985) Fractionation of L fucose-containing oligosaccharides on immobilized *Aleuria aurantia* lectin. J Biol Chem 260: 4688-4693.

Zhang J Z, Popov V L, Gao S, Walker D H, Yu X J (2007) The developmental cycle of *Ehrlichia chaffeensis* in vertebrate cells. Cell Microbiol 9: 610-618.

Zhang, L., Zhang, C., Ojcius, D. M., Sun, D., Zhao, J., Lin, X., et al. (2012). The mammalian cell entry (Mce) protein of pathogenic Leptospira species is responsible for RGD motif-dependent infection of cells and animals. *Molecular microbiology* 83, 1006-1023.

Zhang S, Hai R, Li W, Li G, Lin G, et al. (2009) Seroprevalence of human granulocytotropic anaplasmosis in central and southeastern China. Am J Trop Med Hyg 81: 293-295.

Zhang X C, Zhang L X, Li W H, Wang S W, Sun Y L, et al. (2012) Ehrlichiosis and zoonotic anaplasmosis in suburban areas of Beijing, China. Vector Borne Zoonotic Dis 12: 932-937.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A chimeric protein comprising a polypeptide that is or includes one or more copies of SEQ ID NO:14 and one or more polypeptide sequences that differ from SEQ ID NO:14.

2. The chimeric protein of claim 1, wherein said one or more polypeptide sequences is or includes one or more copies of at least one of SEQ ID NO:03 and SEQ ID NO:06.

3. The chimeric protein of claim 1, wherein the one or more polypeptide sequences is or includes one or more of: an amino acid spacer, an amino acid linker, a signal sequence, a stop transfer sequence, a transmembrane domain, a protein purification ligand, a heterologous protein, SEQ ID NO:01, SEQ ID NO:02, SEQ ID NO:03, SEQ ID NO:04, SEQ ID NO:05, SEQ ID NO:06, SEQ ID NO:07, SEQ ID NO:08, SEQ ID NO:09, SEQ ID NO:13 and SEQ ID NO:15.

\* \* \* \* \*

SEQUENCE LISTING

<160> NUMBER OF SEQ ID NOS: 91

<210> SEQ ID NO 1
<211> LENGTH: 124
<212> TYPE: PRT
<213> ORGANISM: Anaplasma phagocytophilum

<400> SEQUENCE: 1

Met Ile Pro Leu Ala Pro Trp Lys Ser Ile Ser Val Val Tyr Met Ser
1               5                   10                  15

Gly Ser Asp Glu Tyr Lys Glu Ile Ile Lys Gln Cys Ile Gly Ser Val
            20                  25                  30

Lys Glu Val Phe Gly Glu Gly Arg Phe Asp Asp Val Val Ala Ser Ile
        35                  40                  45

Met Lys Met Gln Glu Lys Val Leu Ala Ser Ser Met Gln Gln Asp Asp
    50                  55                  60

Thr Gly Thr Val Gly Gln Ile Glu Ser Gly Gly Ser Gly Ala Arg
65                  70                  75                  80

Leu Ser Asp Glu Gln Val Gln Gln Leu Met Asn Ser Ile Arg Glu Glu
                85                  90                  95

Phe Lys Asp Asp Leu Arg Ala Ile Lys Arg Arg Ile Leu Lys Leu Glu
            100                 105                 110

Arg Ala Val Tyr Gly Ala Asn Thr Pro Lys Glu Ser
        115                 120

<210> SEQ ID NO 2
<211> LENGTH: 24
<212> TYPE: PRT
<213> ORGANISM: Anaplasma phagocytophilum

<400> SEQUENCE: 2

Leu Arg Ala Ile Lys Arg Arg Ile Leu Lys Leu Glu Arg Ala Val Tyr
1               5                   10                  15

Gly Ala Asn Thr Pro Lys Glu Ser
            20

<210> SEQ ID NO 3
<211> LENGTH: 12
<212> TYPE: PRT
<213> ORGANISM: Anaplasma phagocytophilum

<400> SEQUENCE: 3

Arg Ala Val Tyr Gly Ala Asn Thr Pro Lys Glu Ser
1               5                   10

<210> SEQ ID NO 4
<211> LENGTH: 205
<212> TYPE: PRT
<213> ORGANISM: Anaplasma phagocytophilum

<400> SEQUENCE: 4

Met Leu Arg Arg Ser Ser Phe Phe Cys Leu Leu Ala Leu Leu Ser Val
1               5                   10                  15

Thr Ser Cys Gly Thr Leu Leu Pro Asp Ser Asn Val Gly Val Gly Arg
            20                  25                  30

His Asp Leu Gly Ser His Arg Ser Val Ala Phe Ala Lys Lys Val Glu
        35                  40                  45

Lys Val Tyr Phe Asp Ile Gly Leu Tyr Asp Leu Lys Gly Pro Gly Lys
    50                  55                  60

```
Lys Val Ile Leu Glu Leu Val Glu Gln Leu Arg Gln Asp Asp Ser Met
65                  70                  75                  80

Tyr Leu Val Val Ile Gly His Ala Asp Ala Thr Gly Thr Glu Glu Tyr
                85                  90                  95

Ser Leu Ala Leu Gly Glu Lys Arg Ala Asn Ala Val Lys Gln Phe Ile
            100                 105                 110

Ile Gly Cys Asp Lys Ser Leu Ala Pro Arg Val Thr Thr Gln Ser Arg
        115                 120                 125

Gly Lys Ala Glu Pro Glu Val Leu Val Tyr Ser Thr Asp Ala Gln Glu
    130                 135                 140

Val Glu Lys Ala Asn Ala Gln Asn Arg Arg Ala Val Ile Val Val Glu
145                 150                 155                 160

Phe Ala His Ile Pro Arg Ser Gly Val Ala Asp Met His Ala Pro Val
                165                 170                 175

Ala Ser Ser Ile Thr Ser Glu Asn Ser Asn Ala Ser Ala Glu Gly Glu
            180                 185                 190

Asp Met Glu Ala Ser Glu Phe Ser Ser Ala Ile Ala Asn
        195                 200                 205

<210> SEQ ID NO 5
<211> LENGTH: 57
<212> TYPE: PRT
<213> ORGANISM: Anaplasma phagocytophilum

<400> SEQUENCE: 5

Cys Gly Thr Leu Leu Pro Asp Ser Asn Val Gly Val Gly Arg His Asp
1               5                   10                  15

Leu Gly Ser His Arg Ser Val Ala Phe Ala Lys Lys Val Glu Lys Val
            20                  25                  30

Tyr Phe Asp Ile Gly Lys Tyr Asp Leu Lys Gly Pro Gly Lys Lys Val
        35                  40                  45

Ile Leu Glu Leu Val Glu Gln Leu Arg
    50                  55

<210> SEQ ID NO 6
<211> LENGTH: 16
<212> TYPE: PRT
<213> ORGANISM: Anaplasma phagocytophilum

<400> SEQUENCE: 6

Leu Lys Gly Pro Gly Lys Lys Val Ile Leu Glu Leu Val Glu Gln Leu
1               5                   10                  15

<210> SEQ ID NO 7
<211> LENGTH: 9
<212> TYPE: PRT
<213> ORGANISM: Anaplasma phagocytophilum

<400> SEQUENCE: 7

Glu Lys Val Tyr Phe Asp Ile Gly Lys
1               5

<210> SEQ ID NO 8
<211> LENGTH: 16
<212> TYPE: PRT
<213> ORGANISM: Anaplasma phagocytophilum

<400> SEQUENCE: 8

Gly His Ala Asp Ala Thr Gly Thr Glu Glu Tyr Ser Leu Ala Leu Gly
1               5                   10                  15
```

```
<210> SEQ ID NO 9
<211> LENGTH: 21
<212> TYPE: PRT
<213> ORGANISM: Anaplasma phagocytophilum

<400> SEQUENCE: 9

Leu Val Tyr Ser Thr Asp Ala Gln Glu Val Glu Lys Ala Asn Ala Gln
1               5                   10                  15

Asn Arg Arg Ala Val
            20

<210> SEQ ID NO 10
<211> LENGTH: 149
<212> TYPE: PRT
<213> ORGANISM: Anaplasma phagocytophilum

<400> SEQUENCE: 10

Pro Asp Ser Asn Val Gly Val Gly Arg His Asp Leu Gly Ser His Arg
1               5                   10                  15

Ser Val Ala Phe Ala Lys Lys Val Glu Lys Val Tyr Phe Asp Ile Gly
                20                  25                  30

Lys Tyr Asp Leu Lys Gly Pro Gly Lys Lys Val Ile Leu Glu Leu Val
            35                  40                  45

Glu Gln Leu Arg Gln Asp Asp Ser Met Tyr Leu Val Val Ile Gly His
    50                  55                  60

Ala Asp Ala Thr Gly Thr Glu Glu Tyr Ser Leu Ala Leu Gly Glu Lys
65                  70                  75                  80

Arg Ala Asn Ala Val Lys Gln Phe Ile Ile Gly Cys Asp Lys Ser Leu
                85                  90                  95

Ala Pro Arg Val Thr Thr Gln Ser Arg Gly Lys Ala Glu Pro Glu Val
            100                 105                 110

Leu Val Tyr Ser Thr Asp Ala Gln Glu Val Glu Lys Ala Asn Ala Gln
        115                 120                 125

Asn Arg Arg Ala Val Ile Val Val Glu Phe Ala His Ile Pro Arg Ser
    130                 135                 140

Gly Val Ala Asp Met
145

<210> SEQ ID NO 11
<211> LENGTH: 12
<212> TYPE: PRT
<213> ORGANISM: Anaplasma phagocytophilum

<400> SEQUENCE: 11

Leu Arg Ala Ile Lys Arg Arg Ile Leu Lys Leu Glu
1               5                   10

<210> SEQ ID NO 12
<211> LENGTH: 42
<212> TYPE: PRT
<213> ORGANISM: Anaplasma phagocytophilum

<400> SEQUENCE: 12

Asp Glu Tyr Lys Glu Ile Ile Lys Gln Cys Ile Gly Ser Val Lys Glu
1               5                   10                  15

Val Phe Gly Glu Gly Arg Phe Asp Asp Val Val Ala Ser Ile Met Lys
                20                  25                  30

Met Gln Glu Lys Val Leu Ala Ser Ser Met
```

```
                   35                  40

<210> SEQ ID NO 13
<211> LENGTH: 355
<212> TYPE: PRT
<213> ORGANISM: Anaplasma phagocytophilum

<400> SEQUENCE: 13

Met Ser Phe Thr Met Ser Lys Leu Ser Leu Asp Pro Thr Gln Gly Ser
1               5                   10                  15

His Thr Ala Glu Asn Ile Ala Cys Ser Ile Phe Asp Met Val Leu Gly
            20                  25                  30

Val Lys Ser Thr Ala Lys Leu Leu Ala Gly Thr Trp Ala Gly Thr Ser
        35                  40                  45

Ser Thr Ile Trp Lys Thr Val Thr Gly Ala Ala Ser Ser Thr Lys Glu
    50                  55                  60

Ala Ser Ser Lys Ser Tyr Gly Thr Leu Arg Ser Ser Leu Gly Ser Ser
65                  70                  75                  80

Ala Ser Arg Arg Met Leu Gly Thr Cys Ala Thr Ala Leu Cys Leu
            85                  90                  95

Thr Ala Pro Leu Leu Gly Ala Ala Ala Gly Ala Ala Ile Thr Cys
            100                 105                 110

Ala Leu Ile Thr Ile Cys Met Ala Leu Leu Phe Leu Val Leu Tyr Thr
            115                 120                 125

Val Leu His Ile Ala Ser Gln Met Leu Arg Cys Ala Ser Leu Leu Leu
    130                 135                 140

Ser Met Val Cys Asn Ile Leu His Ser Thr Phe Thr Ala Thr Lys Ser
145                 150                 155                 160

Cys Leu Gly Gly Lys Ser Pro Ala Arg Thr Thr Glu Glu Arg Val Ala
                165                 170                 175

Gly Asp Leu Asp His Lys Gly Val Asp Ser Asp Arg Lys His Asp Ala
            180                 185                 190

Glu Lys Thr Glu Glu Lys Lys His Gly Leu Gly Ser Leu Cys Lys Ser
        195                 200                 205

Leu Ala Ile Asn Leu Val Ser Leu Met Gly Thr Ala Leu Val Thr Thr
    210                 215                 220

Pro Ile Ile Leu Leu Ala Val Val Leu Leu Val Leu Pro Val Tyr
225                 230                 235                 240

Leu Leu Cys Ala Thr Val His His Ile Tyr Gln Gly Asn Tyr Glu Asp
                245                 250                 255

Arg Asn Asn Asp Lys Gly Ser Ser Arg Gly Gly Thr Thr Tyr Tyr
            260                 265                 270

Pro Met Thr Met Ser Ala Ser Ala Ser Glu Glu Ser Leu Ser Ser Ile
        275                 280                 285

Ile Ser Glu Gly Gly Leu Ser Lys Thr Ser Leu Pro Ser Tyr Ser Ala
    290                 295                 300

Ala Thr Ala Thr Gly Thr Gly Asn Ala Thr Gly Glu Val Phe Ser His
305                 310                 315                 320

Ser His Ser Ser Gly Lys Ser Ser Lys Pro Glu Ser Arg Pro Glu
                325                 330                 335

Ser Asn Leu Gln Asn Val Val Ala Glu Thr Met Ser Gln Gln Gln Arg
            340                 345                 350

Ser Val Ser
        355
```

<210> SEQ ID NO 14
<211> LENGTH: 13
<212> TYPE: PRT
<213> ORGANISM: Anaplasma phagocytophilum

<400> SEQUENCE: 14

Ser Leu Asp Pro Thr Gln Gly Ser His Thr Ala Glu Asn
1               5                   10

<210> SEQ ID NO 15
<211> LENGTH: 87
<212> TYPE: PRT
<213> ORGANISM: Anaplasma phagocytophilum

<400> SEQUENCE: 15

Met Ser Phe Thr Met Ser Lys Leu Ser Leu Asp Pro Thr Gln Gly Ser
1               5                   10                  15

His Thr Ala Glu Asn Ile Ala Cys Ser Ile Phe Asp Met Val Leu Gly
            20                  25                  30

Val Lys Ser Thr Ala Lys Leu Leu Ala Gly Thr Trp Ala Gly Thr Ser
        35                  40                  45

Ser Thr Ile Trp Lys Thr Val Thr Gly Ala Ala Ser Ser Thr Lys Glu
    50                  55                  60

Ala Ser Ser Lys Ser Tyr Gly Thr Leu Arg Ser Ser Leu Gly Ser Ser
65                  70                  75                  80

Ala Ser Arg Arg Met Leu Gly
                85

<210> SEQ ID NO 16
<211> LENGTH: 130
<212> TYPE: PRT
<213> ORGANISM: Anaplasma marginale

<400> SEQUENCE: 16

Met Ser Gly Glu Asp Glu Tyr Lys Glu Ile Ile Arg Gln Cys Ile Gly
1               5                   10                  15

Ser Val Lys Glu Val Phe Gly Glu Gly Arg Phe Asp Asp Val Val Ala
            20                  25                  30

Ser Ile Met Lys Met Gln Glu Lys Val Leu Ala Ser Ser Met Lys Asp
        35                  40                  45

Gly Asp Pro Val Gly Gln Ile Ala Ala Asp Gly Val Gly Asn Glu Leu
    50                  55                  60

Tyr Asp Arg Ile Ala Asp Arg Leu Glu Glu Arg Val Ser Gln Lys Ile
65                  70                  75                  80

Ser Glu Asp Leu Arg Ile Ile Lys Lys Arg Leu Leu Arg Leu Glu Arg
                85                  90                  95

Val Val Leu Gly Gly Gly Ser Val Ser Gly Asp Ala Ala His Gln
            100                 105                 110

Val Ser Gly Asn Gln Pro Ser Gln Gln Asn Ser Ser Ala Ala Ala Glu
        115                 120                 125

Gly Gly
    130

<210> SEQ ID NO 17
<211> LENGTH: 32
<212> TYPE: PRT
<213> ORGANISM: Anaplasma marginale

<400> SEQUENCE: 17

-continued

Leu Gly Gly Gly Ser Val Ser Gly Asp Ala Ala Ala His Gln Val Ser
1               5                   10                  15

Gly Asn Gln Pro Ser Gln Asn Ser Ser Ala Ala Ala Glu Gly Gly
            20                  25                  30

<210> SEQ ID NO 18
<211> LENGTH: 131
<212> TYPE: PRT
<213> ORGANISM: Anaplasma marginale

<400> SEQUENCE: 18

Met Ser Gly Glu Asp Glu Tyr Lys Glu Ile Ile Arg Gln Cys Ile Gly
1               5                   10                  15

Ser Val Lys Glu Val Phe Gly Glu Gly Arg Phe Asp Asp Val Val Ala
            20                  25                  30

Ser Ile Met Lys Met Gln Glu Lys Val Leu Ala Ser Ser Met Lys Asp
        35                  40                  45

Gly Asp Pro Val Gly Gln Ile Ala Ala Asp Val Gly Asn Glu Leu
    50                  55                  60

Tyr Asp Arg Ile Ala Asp Arg Leu Glu Arg Val Ser Gln Lys Ile
65                  70                  75                  80

Ser Glu Asp Leu Arg Ile Ile Lys Lys Arg Leu Leu Arg Leu Glu Arg
                85                  90                  95

Val Val Leu Gly Gly Ser Val Ser Gly Asp Ala Ala Ala His
            100                 105                 110

Gln Val Ser Gly Asn Gln Pro Ser Gln Asn Ser Ala Ala Ala
        115                 120                 125

Glu Gly Gly
    130

<210> SEQ ID NO 19
<211> LENGTH: 33
<212> TYPE: PRT
<213> ORGANISM: Anaplasma marginale

<400> SEQUENCE: 19

Leu Gly Gly Gly Ser Val Ser Gly Asp Ala Ala Ala His Gln Val
1               5                   10                  15

Ser Gly Asn Gln Pro Ser Gln Asn Ser Ser Ala Ala Glu Gly
            20                  25                  30

Gly

<210> SEQ ID NO 20
<211> LENGTH: 46
<212> TYPE: PRT
<213> ORGANISM: Anaplasma marginale

<400> SEQUENCE: 20

Met Ser Gly Glu Asp Glu Tyr Lys Glu Ile Ile Arg Gln Cys Ile Gly
1               5                   10                  15

Ser Val Lys Glu Val Phe Gly Glu Gly Arg Phe Asp Asp Val Val Ala
            20                  25                  30

Ser Ile Met Lys Met Gln Glu Lys Val Leu Ala Ser Ser Met
        35                  40                  45

<210> SEQ ID NO 21
<211> LENGTH: 16
<212> TYPE: PRT

```
<213> ORGANISM: Anaplasma marginale

<400> SEQUENCE: 21

Asp Leu Arg Ile Ile Lys Lys Arg Leu Leu Arg Leu Glu Arg Val Val
1               5                   10                  15

<210> SEQ ID NO 22
<211> LENGTH: 104
<212> TYPE: PRT
<213> ORGANISM: Ehrlichia chaffeensis

<400> SEQUENCE: 22

Met Ala Glu Asp Asp Tyr Lys Gly Val Ile Lys Gln Tyr Ile Asp Thr
1               5                   10                  15

Val Lys Glu Ile Val Gly Asp Ser Lys Thr Phe Asp Gln Met Phe Glu
                20                  25                  30

Ser Val Val Arg Ile Gln Glu Arg Val Met Ala Ala Asn Ala Gln Asn
            35                  40                  45

Asn Glu Asp Gly Val Ile Asp Asn Gly Asp Gln Val Lys Arg Ile Gly
        50                  55                  60

Ser Ser Thr Ser Glu Ser Ile Ser Asn Thr Glu Tyr Lys Glu Leu Met
65                  70                  75                  80

Glu Glu Leu Lys Val Ile Lys Lys Arg Ile Leu Arg Leu Glu Arg Lys
                85                  90                  95

Ile Leu Lys Pro Lys Glu Glu Val
            100

<210> SEQ ID NO 23
<211> LENGTH: 42
<212> TYPE: PRT
<213> ORGANISM: Ehrlichia chaffeensis

<400> SEQUENCE: 23

Met Ala Glu Asp Asp Tyr Lys Gly Val Ile Lys Gln Tyr Ile Asp Thr
1               5                   10                  15

Val Lys Glu Ile Val Gly Asp Ser Lys Thr Phe Asp Gln Met Phe Glu
                20                  25                  30

Ser Val Val Arg Ile Gln Glu Arg Val Met
            35                  40

<210> SEQ ID NO 24
<211> LENGTH: 13
<212> TYPE: PRT
<213> ORGANISM: Ehrlichia chaffeensis

<400> SEQUENCE: 24

Glu Leu Lys Val Ile Lys Lys Arg Ile Leu Arg Leu Glu
1               5                   10

<210> SEQ ID NO 25
<211> LENGTH: 10
<212> TYPE: PRT
<213> ORGANISM: Ehrlichia chaffeensis

<400> SEQUENCE: 25

Arg Lys Ile Leu Lys Pro Lys Glu Glu Val
1               5                   10

<210> SEQ ID NO 26
<211> LENGTH: 98
<212> TYPE: PRT
```

<213> ORGANISM: Ehrlichia canis

<400> SEQUENCE: 26

Met Ala Asp Asp Glu Tyr Lys Gly Val Ile Gln Gln Tyr Ile Asn Thr
1               5                   10                  15

Val Lys Glu Ile Val Ser Asp Ser Lys Thr Phe Asp Gln Met Phe Glu
            20                  25                  30

Ser Val Val Lys Ile Gln Glu Arg Val Met Glu Ala Asn Ala Gln Asn
        35                  40                  45

Asp Asp Gly Ser Gln Val Lys Arg Ile Gly Ser Ser Thr Ser Asp Ser
    50                  55                  60

Ile Ser Asp Ser Gln Tyr Lys Glu Leu Ile Glu Leu Lys Val Ile
65                  70                  75                  80

Lys Lys Arg Leu Leu Arg Leu Glu His Lys Val Leu Lys Pro Lys Glu
                85                  90                  95

Gly Ala

<210> SEQ ID NO 27
<211> LENGTH: 42
<212> TYPE: PRT
<213> ORGANISM: Ehrlichia canis

<400> SEQUENCE: 27

Met Ala Asp Asp Glu Tyr Lys Gly Val Ile Gln Gln Tyr Ile Asn Thr
1               5                   10                  15

Val Lys Glu Ile Val Ser Asp Ser Lys Thr Phe Asp Gln Met Phe Glu
            20                  25                  30

Ser Val Val Lys Ile Gln Glu Arg Val Met
        35                  40

<210> SEQ ID NO 28
<211> LENGTH: 13
<212> TYPE: PRT
<213> ORGANISM: Ehrlichia canis

<400> SEQUENCE: 28

Glu Leu Lys Val Ile Lys Lys Arg Leu Leu Arg Leu Glu
1               5                   10

<210> SEQ ID NO 29
<211> LENGTH: 10
<212> TYPE: PRT
<213> ORGANISM: Ehrlichia canis

<400> SEQUENCE: 29

His Lys Val Leu Lys Pro Lys Glu Gly Ala
1               5                   10

<210> SEQ ID NO 30
<211> LENGTH: 105
<212> TYPE: PRT
<213> ORGANISM: Ehrlichia ruminantium

<400> SEQUENCE: 30

Met Ala Asp Glu Asp Tyr Lys Gly Val Ile Lys Gln Tyr Ile Asp Thr
1               5                   10                  15

Val Lys Glu Ile Val Gly Asp Ser Lys Thr Phe Asp Gln Met Phe Glu
            20                  25                  30

Ser Val Val Lys Ile Gln Glu Arg Val Met Ala Ala Ser Ala Gln Asn
        35                  40                  45

```
Glu Ala Asn Gly Ala Leu Val Glu Gly Asp Ser Lys Met Lys Arg Ile
            50                  55                  60

Arg Ser Ala Asp Asp Ser Ile Ala Tyr Thr Gln Ser Gln Glu Leu Leu
 65                  70                  75                  80

Glu Glu Leu Lys Val Leu Lys Lys Arg Ile Ala Arg Leu Glu Arg His
                    85                  90                  95

Val Phe Lys Ser Asn Lys Thr Glu Ala
                100                 105

<210> SEQ ID NO 31
<211> LENGTH: 42
<212> TYPE: PRT
<213> ORGANISM: Ehrlichia ruminantium

<400> SEQUENCE: 31

Met Ala Asp Glu Asp Tyr Lys Gly Val Ile Lys Gln Tyr Ile Asp Thr
 1               5                  10                  15

Val Lys Glu Ile Val Gly Asp Ser Lys Thr Phe Asp Gln Met Phe Glu
                20                  25                  30

Ser Val Val Lys Ile Gln Glu Arg Val Met
            35                  40

<210> SEQ ID NO 32
<211> LENGTH: 13
<212> TYPE: PRT
<213> ORGANISM: Ehrlichia ruminantium

<400> SEQUENCE: 32

Glu Leu Lys Val Leu Lys Lys Arg Ile Ala Arg Leu Glu
 1               5                  10

<210> SEQ ID NO 33
<211> LENGTH: 11
<212> TYPE: PRT
<213> ORGANISM: Ehrlichia ruminantium

<400> SEQUENCE: 33

Arg His Val Phe Lys Ser Asn Lys Thr Glu Ala
 1               5                  10

<210> SEQ ID NO 34
<211> LENGTH: 236
<212> TYPE: PRT
<213> ORGANISM: Anaplasma marginale

<400> SEQUENCE: 34

Met Leu His Arg Trp Leu Ala Leu Cys Phe Leu Ala Ser Phe Ala Val
 1               5                  10                  15

Thr Gly Cys Gly Leu Phe Ser Lys Glu Lys Val Gly Met Asp Ile Val
                20                  25                  30

Gly Val Pro Phe Ser Ala Gly Arg Val Glu Lys Val Tyr Phe Asp Phe
            35                  40                  45

Asn Lys Tyr Glu Ile Lys Gly Ser Gly Lys Val Leu Leu Gly Leu
         50                  55                  60

Val Glu Arg Met Lys Ala Asp Lys Arg Ser Thr Leu Leu Ile Ile Gly
 65                  70                  75                  80

His Thr Asp Ser Arg Gly Thr Glu Glu Tyr Asn Leu Ala Leu Gly Glu
                    85                  90                  95

Arg Arg Ala Asn Ala Val Lys Glu Phe Ile Leu Gly Cys Asp Arg Ser
```

```
                100                 105                 110
Leu Ser Pro Arg Ile Ser Thr Gln Ser Arg Gly Lys Ala Glu Pro Glu
            115                 120                 125

Val Leu Val Tyr Ser Ser Asp Phe Lys Glu Ala Glu Lys Ala His Ala
        130                 135                 140

Gln Asn Arg Arg Val Val Leu Ile Val Glu Cys Gln His Ser Val Ser
145                 150                 155                 160

Pro Lys Lys Lys Met Ala Ile Lys Trp Pro Phe Ser Phe Gly Arg Ser
                165                 170                 175

Ala Ala Lys Gln Asp Asp Val Gly Ser Ser Glu Val Ser Asp Glu Asn
            180                 185                 190

Pro Val Asp Asp Ser Ser Glu Gly Ile Ala Ser Glu Ala Ala Pro
        195                 200                 205

Glu Glu Gly Val Val Ser Glu Glu Ala Ala Glu Ala Pro Glu Val
    210                 215                 220

Ala Gln Asp Ser Ser Ala Gly Val Val Ala Pro Glu
225                 230                 235

<210> SEQ ID NO 35
<211> LENGTH: 59
<212> TYPE: PRT
<213> ORGANISM: Anaplasma marginale

<400> SEQUENCE: 35

Leu Phe Ser Lys Glu Lys Val Gly Met Asp Ile Val Gly Val Pro Phe
1               5                   10                  15

Ser Ala Gly Arg Val Glu Lys Val Tyr Phe Asp Phe Asn Lys Tyr Glu
                20                  25                  30

Ile Lys Gly Ser Gly Lys Lys Val Leu Leu Gly Leu Val Glu Arg Met
            35                  40                  45

Lys Ala Asp Lys Arg Ser Thr Leu Leu Ile Ile
        50                  55

<210> SEQ ID NO 36
<211> LENGTH: 212
<212> TYPE: PRT
<213> ORGANISM: Anaplasma marginale

<400> SEQUENCE: 36

Met Leu His Arg Trp Le

```
                130                 135                 140
Gln Asn Arg Arg Val Val Leu Ile Met Glu Cys Gln His Ala Ala Ser
145                 150                 155                 160

Pro Lys Lys Ala Arg Val Ser Arg Trp Pro Phe Ser Phe Gly Arg Ser
                165                 170                 175

Ser Ala Thr Gln Gln Asp Asn Gly Gly Thr Val Ala Ala Gly Ser
            180                 185                 190

Pro Gly Glu Asp Ala Pro Ala Glu Val Val Glu Pro Glu Glu Thr Gln
        195                 200                 205

Glu Ala Gly Glu
    210

<210> SEQ ID NO 37
<211> LENGTH: 59
<212> TYPE: PRT
<213> ORGANISM: Anaplasma marginale

<400> SEQUENCE: 37

Leu Phe Asn Lys Glu Lys Val Asn Ile Asp Ile Gly Gly Val Pro Leu
1               5                   10                  15

Ser Ala Gly Arg Val Glu Lys Val Tyr Phe Asp Phe Asn Lys Tyr Glu
            20                  25                  30

Ile Lys Gly Ser Gly Lys Lys Val Leu Leu Gly Leu Val Glu Arg Met
        35                  40                  45

Lys Ala Asp Lys Met Ser Thr Leu Leu Ile Val
    50                  55

<210> SEQ ID NO 38
<211> LENGTH: 34
<212> TYPE: PRT
<213> ORGANISM: Anaplasma marginale

<400> SEQUENCE: 38

Ala Gly Arg Val Glu Lys Val Tyr Phe Asp Phe Asn L

```
<210> SEQ ID NO 41
<211> LENGTH: 23
<212> TYPE: PRT
<213> ORGANISM: Anaplasma marginale

<400> SEQUENCE: 41
```

Leu Val Tyr Ser Ser Asp Phe Lys Glu Ala Glu Lys Ala His Ala Gln
1               5                   10                  15

Asn Arg Arg Val Val Leu Ile
            20

```
<210> SEQ ID NO 42
<211> LENGTH: 175
<212> TYPE: PRT
<213> ORGANISM: Ehrlichia chaffeensis

<400> SEQUENCE: 42
```

Met Lys His Lys Leu Val Phe Ile Lys Phe Met Leu Leu Cys Leu Ile
1               5                   10                  15

Leu Ser Ser Cys Lys Thr Thr Asp His Val Pro Leu Val Asn Val Asp
            20                  25                  30

His Val Phe Ser Asn Thr Lys Thr Ile Glu Lys Ile Tyr Phe Gly Phe
        35                  40                  45

Gly Lys Ala Thr Ile Glu Asp Ser Asp Lys Thr Ile Leu Glu Lys Val
    50                  55                  60

Met Gln Lys Ala Glu Glu Tyr Pro Asp Thr Asn Ile Ile Ile Val Gly
65                  70                  75                  80

His Thr Asp Thr Arg Gly Thr Asp Glu Tyr Asn Leu Glu Leu Gly Lys
                85                  90                  95

Gln Arg Ala Asn Ala Val Lys Asp Phe Ile Leu Glu Arg Asn Lys Ser
            100                 105                 110

Leu Glu Asp Arg Ile Ile Ile Glu Ser Lys Gly Lys Ser Glu Pro Ala
        115                 120                 125

Val Leu Val Tyr Ser Asn Asn Pro Glu Glu Ala Glu Tyr Ala His Thr
    130                 135                 140

Lys Asn Arg Arg Val Val Ile Thr Leu Thr Asp Asn Leu Ile Tyr Lys
145                 150                 155                 160

Ala Lys Ser Ser Asp Lys Asp Pro Ser Ser Asn Lys Thr Glu Gln
                165                 170                 175

```
<210> SEQ ID NO 43
<211> LENGTH: 50
<212> TYPE: PRT
<213> ORGANISM: Ehrlichia chaffeensis

<400> SEQUENCE: 43
```

Asn Val Asp His Val Phe Ser Asn Thr Lys Thr Ile Glu Lys Ile Tyr
1               5                   10                  15

Phe Gly Phe Gly Lys Ala Thr Ile Glu Asp Ser Asp Lys Thr Ile Leu
            20                  25                  30

Glu Lys Val Met Gln Lys Ala Glu Glu Tyr Pro Asp Thr Asn Ile Ile
        35                  40                  45

Ile Val
    50

```
<210> SEQ ID NO 44
<211> LENGTH: 27
<212> TYPE: PRT
<213> ORGANISM: Ehrlichia chaffeensis
```

<400> SEQUENCE: 44

Ile Glu Asp Ser Asp Lys Thr Ile Leu Glu Lys Val Met Gln Lys Ala
1               5                   10                  15

Glu Glu Tyr Pro Asp Thr Asn Ile Ile Ile Val
            20                  25

<210> SEQ ID NO 45
<211> LENGTH: 17
<212> TYPE: PRT
<213> ORGANISM: Ehrlichia chaffeensis

<400> SEQUENCE: 45

Gly His Thr Asp Thr Arg Gly Thr Asp Glu Tyr Asn Leu Glu Leu Gly
1               5                   10                  15

Glu

<210> SEQ ID NO 46
<211> LENGTH: 33
<212> TYPE: PRT
<213> ORGANISM: Ehrlichia chaffeensis

<400> SEQUENCE: 46

Gln Arg Ala Asn Ala Val Lys Asp Phe Ile Leu Glu Arg Asn Lys Ser
1               5                   10                  15

Leu Glu Asp Arg Ile Ile Ile Glu Ser Lys Gly Lys Ser Glu Pro Ala
            20                  25                  30

Val

<210> SEQ ID NO 47
<211> LENGTH: 22
<212> TYPE: PRT
<213> ORGANISM: Ehrlichia chaffeensis

<400> SEQUENCE: 47

Leu Val Tyr Ser Asn Asn Pro Glu Glu Ala Glu Tyr Ala His Thr Lys
1               5                   10                  15

Asn Arg Arg Val Val Ile
            20

<210> SEQ ID NO 48
<211> LENGTH: 162
<212> TYPE: PRT
<213> ORGANISM: Ehrlichia canis

<400> SEQUENCE: 48

Met Lys His Lys Leu Val Phe Ile Lys Phe Ile Leu Leu Cys Leu Ile
1               5                   10                  15

Leu Ser Ser Cys Lys Thr Thr Asp His Val Pro Leu Val Asn Thr Asp
            20                  25                  30

His Val Phe Ser Asn Met Lys Thr Ile Glu Lys Ile Tyr Phe Asp Phe
        35                  40                  45

Gly Lys Ala Thr Ile Gly Asp Ser Asp Lys Ala Ile Leu Glu Lys Val
    50                  55                  60

Ile Gln Lys Ala Gln Lys Asp Thr Asn Thr Asn Ile Val Ile Val Gly
65                  70                  75                  80

His Thr Asp Thr Arg Gly Thr Asp Glu Tyr Asn Leu Glu Leu Gly Glu
                85                  90                  95

Gln Arg Ala Asn Ala Val Lys Asp Phe Ile Ile Glu His Asp Lys Ser

```
                    100                 105                 110
Leu Glu Asn Arg Ile Thr Val Gln Ser Lys Gly Lys Ser Glu Pro Ala
            115                 120                 125

Val Leu Val Tyr Ser Ser Asn Pro Glu Glu Ala Glu His Ala His Ala
        130                 135                 140

Lys Asn Arg Arg Val Val Ile Thr Leu Thr Asp Asn Gly Asn Lys Thr
145                 150                 155                 160

Ser Gln

<210> SEQ ID NO 49
<211> LENGTH: 58
<212> TYPE: PRT
<213> ORGANISM: Ehrlichia canis

<400> SEQUENCE: 49

Thr Thr Asp His Val Pro Leu Val Asn Thr Asp His Val Phe Ser Asn
1               5                   10                  15

Met Lys Thr Ile Glu Lys Ile Tyr Phe Asp Phe Gly Lys Ala Thr Ile
            20                  25                  30

Gly Asp Ser Asp Lys Ala Ile Leu Glu Lys Val Ile Gln Lys Ala Gln
        35                  40                  45

Lys Asp Thr Asn Thr Asn Ile Val Ile Val
    50                  55

<210> SEQ ID NO 50
<211> LENGTH: 26
<212> TYPE: PRT
<213> ORGANISM: Ehrlichia canis

<400> SEQUENCE: 50

Gly Asp Ser Asp Lys Ala Ile Leu Glu Lys Val Ile Gln Lys Ala Gln
1               5                   10                  15

Lys Asp Thr Asn Thr Asn Ile Val Ile Val
            20                  25

<210> SEQ ID NO 51
<211> LENGTH: 17
<212> TYPE: PRT
<213> ORGANISM: Ehrlichia canis

<400> SEQUENCE: 51

Gly His Thr Asp Thr Arg Gly Thr Asp Glu Tyr Asn Leu Glu Leu Gly
1               5                   10                  15

Glu

<210> SEQ ID NO 52
<211> LENGTH: 33
<212> TYPE: PRT
<213> ORGANISM: Ehrlichia canis

<400> SEQUENCE: 52

Gln Arg Ala Asn Ala Val Lys Asp Phe Ile Ile Glu His Asp Lys Ser
1               5                   10                  15

Leu Glu Asn Arg Ile Thr Val Gln Ser Lys Gly Lys Ser Glu Pro Ala
            20                  25                  30

Val

<210> SEQ ID NO 53
<211> LENGTH: 22
```

```
<212> TYPE: PRT
<213> ORGANISM: Ehrlichia canis

<400> SEQUENCE: 53

Leu Val Tyr Ser Ser Asn Pro Glu Glu Ala Glu His Ala His Ala Lys
1               5                   10                  15

Asn Arg Arg Val Val Ile
            20

<210> SEQ ID NO 54
<211> LENGTH: 217
<212> TYPE: PRT
<213> ORGANISM: Ehrlichia runantium

<400> SEQUENCE: 54

Met Arg Tyr Gln Leu Ile Val Ala Asn Leu Ile Leu Leu Cys Leu Thr
1               5                   10                  15

Leu Asn Gly Cys His Phe Asn Ser Lys His Val Pro Leu Val Asn Val
            20                  25                  30

His Asn Leu Phe Ser Asn Ile Lys Ala Ile Asp Lys Val Tyr Phe Asp
        35                  40                  45

Leu Asp Lys Thr Val Ile Lys Asp Ser Asp Lys Val Leu Leu Glu Lys
    50                  55                  60

Leu Val Gln Lys Ala Gln Glu Asp Pro Thr Thr Asp Ile Ile Ile Val
65                  70                  75                  80

Gly His Thr Asp Thr Arg Gly Thr Asp Glu Tyr Asn Leu Ala Leu Gly
                85                  90                  95

Glu Gln Arg Ala Asn Ala Val Arg Asp Phe Ile Ile Ser Cys Asp Lys
            100                 105                 110

Ser Leu Glu Lys Arg Ile Thr Val Arg Ser Lys Gly Lys Ser Glu Pro
        115                 120                 125

Ala Ile Leu Val Tyr Ser Asn Asn Pro Lys Glu Ala Glu Asp Ala His
    130                 135                 140

Ala Lys Asn Arg Arg Val Val Ile Thr Leu Val Asn Asn Ser Thr Ser
145                 150                 155                 160

Thr Asp Asn Lys Val Pro Thr Thr Thr Pro Phe Asn Glu Glu Ala
                165                 170                 175

His Asn Thr Ile Ser Lys Asp Gln Glu Asn Asn Thr Gln Gln Gln Ala
            180                 185                 190

Lys Ser Asp Asn Ile Asn Asn Ile Asn Thr Gln Gln Lys Leu Glu Gln
        195                 200                 205

Asp Asn Asn Asn Thr Pro Glu Val Asn
    210                 215

<210> SEQ ID NO 55
<211> LENGTH: 58
<212> TYPE: PRT
<213> ORGANISM: Ehrlichia ruminantium

<400> SEQUENCE: 55

Asn Ser Lys His Val Pro Leu Val Asn Val His Asn Leu Phe Ser Asn
1               5                   10                  15

Ile Lys Ala Ile Asp Lys Val Tyr Phe Asp Leu Asp Lys Thr Val Ile
            20                  25                  30

Lys Asp Ser Asp Lys Val Leu Leu Glu Lys Leu Val Gln Lys Ala Gln
        35                  40                  45

Glu Asp Pro Thr Thr Asp Ile Ile Ile Val
    50                  55
```

<210> SEQ ID NO 56
<211> LENGTH: 25
<212> TYPE: PRT
<213> ORGANISM: Ehrlichia ruminantium

<400> SEQUENCE: 56

Asp Ser Asp Lys Val Leu Leu Glu Lys Leu Val Gln Lys Ala Gln Glu
1               5                   10                  15

Asp Pro Thr Thr Asp Ile Ile Ile Val
            20                  25

<210> SEQ ID NO 57
<211> LENGTH: 17
<212> TYPE: PRT
<213> ORGANISM: Erhlichia ruminantium

<400> SEQUENCE: 57

Gly His Thr Asp Thr Arg Gly Thr Asp Glu Tyr Asn Leu Ala Leu Gly
1               5                   10                  15

Glu

<210> SEQ ID NO 58
<211> LENGTH: 33
<212> TYPE: PRT
<213> ORGANISM: Ehrlichia ruminantium

<400> SEQUENCE: 58

Gln Arg Ala Asn Ala Val Arg Asp Phe Ile Ile Ser Cys Asp Lys Ser
1               5                   10                  15

Leu Glu Lys Arg Ile Thr Val Arg Ser Lys Gly Lys Ser Glu Pro Ala
            20                  25                  30

Ile

<210> SEQ ID NO 59
<211> LENGTH: 22
<212> TYPE: PRT
<213> ORGANISM: Ehrlichia ruminantium

<400> SEQUENCE: 59

Leu Val Tyr Ser Asn Asn Pro Lys Glu Ala Gly Asp Ala His Ala Lys
1               5                   10                  15

Asn Arg Arg Val Val Ile
            20

<210> SEQ ID NO 60
<211> LENGTH: 338
<212> TYPE: PRT
<213> ORGANISM: Anaplasma phagocytophilum

<400> SEQUENCE: 60

Met Arg Thr Phe Cys Trp Phe Val His Arg Phe Tyr Leu Arg Asn Tyr
1               5                   10                  15

Cys Phe Leu Asn Lys Asn Cys Ser Gln Cys Ser Asn Thr Thr Tyr Thr
            20                  25                  30

Ser Thr Thr Val Ile Ile Tyr Ala Thr Ile Ser Ser Lys Ser Ile Val
        35                  40                  45

Ile Ser Phe Ser Asp Ala Arg Cys Val Glu Asp Phe Lys Gly Lys Phe
    50                  55                  60

```
Thr Thr Leu Asp Ala Gly Ile Ala Ser Arg Ala Ile Phe Ser Met Ser
 65                  70                  75                  80

Val Ala Ile Lys Tyr Ser Asp Lys Asn Leu Val Glu Leu Ile Pro Glu
                 85                  90                  95

Gly Glu Phe Thr Tyr Cys Asp Val Asn Thr Met Val Gly His Met Leu
            100                 105                 110

Arg His Gly Phe Thr Phe Lys Gln Glu Val Leu Ser Ser Ile Leu Glu
        115                 120                 125

Gln Ala Ser Ala Leu Ala Thr Glu Asn Phe Val Val Leu Lys Ala Gly
    130                 135                 140

Glu Arg Ser Ser Tyr Ile Val Gly Val Tyr Gln Asp Thr Val Thr Val
145                 150                 155                 160

Ser Pro Leu Thr Ser Glu Tyr Leu Asp Leu Glu Ser Gly Pro Ser Gln
                165                 170                 175

Arg Leu Val Lys Leu Leu Arg Thr Glu Ser Ala Ile Ser Ser Val Asn
            180                 185                 190

Val Asp Ala Gln Asn Arg Ser Ile Thr Ile Leu Val Arg Gly Asn Val
        195                 200                 205

Cys Asp Ala Leu Gly Thr Leu Cys Asn Val Met Ile Thr Ile Gly Ala
    210                 215                 220

Ile Glu Ala Lys Glu Lys Gly Ala Val Leu Val Lys Leu Val Arg Leu
225                 230                 235                 240

Ala Phe Leu Asp Leu Met Gly Asn Glu Ile Arg Ser Val Arg Asn Ile
                245                 250                 255

Ala Ser Cys Ser Val Ala His Pro Leu Ser Lys Tyr Lys Gly Val Ala
            260                 265                 270

Arg Thr Ile Glu Asn Ile Leu Thr Cys Leu Ser Asn Lys Thr Leu Asp
        275                 280                 285

Ala Val Val Leu Gly Gln Leu Glu Asp Ala Leu Glu Gly Lys Gly Glu
    290                 295                 300

Phe Ser Ala Leu Pro Ser Val Leu Thr Lys Gly Phe Lys Leu Asn
305                 310                 315                 320

Arg Asp Phe Asn Gly Gln Leu Glu Asn Ile Ile Gly Ser Glu Lys Arg
                325                 330                 335

Val Gln

<210> SEQ ID NO 61
<211> LENGTH: 147
<212> TYPE: PRT
<213> ORGANISM: Anaplasma phagocytophilum

<400> SEQUENCE: 61

Met Gln Gln Ser Ile Ser Thr Asp Thr Leu Gly Ser Ser Glu Val Arg
  1               5                  10                  15

Gln Pro Lys Pro Arg Lys Ile Ala Thr Gly Ala Arg Ala Ser Arg Ala
                 20                  25                  30

Thr Thr Ala Ala Arg Lys Ser Val Ser Thr Thr Asn Lys Asn Val
             35                  40                  45

Ala Val Asp Val Arg Ser Arg Ser Ser Lys Ser His Asn Asp Asp Lys
         50                  55                  60

Val Ala Ile Asp Ser His Ala Glu Ala Arg Gln Leu Pro Glu Glu Asp
 65                  70                  75                  80

Arg Lys Glu Ser Leu Ser Pro Asp Val Ser Thr Val Lys Ser Glu His
                 85                  90                  95
```

```
Ala Ser Arg Ser Ser Glu Asp Ile Gln Ser Pro Val Asp Asn Ser Gly
            100                 105                 110

Pro Glu Val Ser Gly Gly Leu Lys Thr Arg Tyr Ser Ala Trp Ile Ala
        115                 120                 125

Leu Leu Cys Lys Gln Tyr Gly Arg Phe Thr Ala Phe Phe Ser Lys Lys
130                 135                 140

Arg Glu Ser
145

<210> SEQ ID NO 62
<211> LENGTH: 645
<212> TYPE: PRT
<213> ORGANISM: Anaplasma phagocytophilum

<400> SEQUENCE: 62

Met Ala Ala Glu Arg Ile Ile Gly Ile Asp Leu Gly Thr Thr Asn Ser
1               5                   10                  15

Cys Val Ala Val Met Glu Ala Gly Thr Ala Lys Val Ile Glu Asn Ser
            20                  25                  30

Glu Gly Ser Arg Thr Thr Pro Ser Val Val Ala Phe Thr Asp Asn Glu
        35                  40                  45

Arg Leu Val Gly Glu Leu Ala Lys Arg Gln Ala Asn Ile Asn Ala Gln
    50                  55                  60

Asn Thr Ile Tyr Ala Ser Lys Arg Ile Gly Arg Arg Tyr Asp Asp
65                  70                  75                  80

Met Arg Asp Leu Lys Cys Pro Tyr Glu Val Phe Pro Ala Lys Asn Gly
                85                  90                  95

Asp Ala Trp Ile Arg Ala Lys Gly Glu Gly Tyr Ser Pro Val Gln Ile
            100                 105                 110

Gly Ala Phe Val Leu Glu Lys Ile Lys Glu Thr Ala Glu Arg Tyr Phe
        115                 120                 125

Gly Ala Pro Val Lys Lys Ala Val Ile Thr Val Pro Ala Tyr Phe Asn
    130                 135                 140

Asp Ala Gln Arg Gln Ala Thr Lys Asp Ala Gly Thr Ile Ala Gly Leu
145                 150                 155                 160

Asp Val Val Arg Ile Ile Asn Glu Pro Thr Ala Ala Ala Leu Ala Tyr
                165                 170                 175

Gly Leu Asp Lys Gly Asp Lys Gln Arg Thr Ile Val Val Tyr Asp Leu
            180                 185                 190

Gly Gly Gly Thr Phe Asp Val Ser Val Leu Glu Ile Ala Asp Gly Val
        195                 200                 205

Phe Glu Val Lys Ala Thr Asn Gly Asp Thr Lys Leu Gly Gly Glu Asp
    210                 215                 220

Phe Asp Asn Ala Ile Met Glu His Met Met Glu Ser Phe Gln Lys Glu
225                 230                 235                 240

Thr Gly Ile Asn Leu Arg Asn Asp Pro Met Ala Val Gln Arg Val Lys
                245                 250                 255

Glu Ala Ala Glu Lys Ala Lys Ile Glu Leu Ser Thr Arg Leu Glu Thr
            260                 265                 270

Asp Ile Thr Leu Pro Phe Ile Ser Ser Asp Ser Thr Gly Ala Lys His
        275                 280                 285

Leu Ser Leu Lys Leu Ser Arg Ala Lys Phe Glu Gly Leu Val Asp Glu
    290                 295                 300

Leu Ile Glu Arg Thr Ile Glu Pro Cys Lys Lys Ala Leu Ser Asp Ala
305                 310                 315                 320
```

Gly Ile Lys Asp Asn Ser Lys Val Asp Glu Val Val Leu Val Gly Gly
            325                 330                 335

Met Thr Arg Val Pro Lys Val Ile Gln Arg Val Lys Asp Phe Phe Gly
            340                 345                 350

Lys Glu Pro Cys Gln Gly Val Asn Pro Asp Glu Val Val Ala Val Gly
            355                 360                 365

Ala Ala Ile Gln Gly Gly Ile Leu Thr Gly Asp Val Arg Asp Val Leu
        370                 375                 380

Leu Leu Asp Val Ala Pro Leu Ser Leu Gly Ile Glu Thr Leu Gly Gly
385                 390                 395                 400

Val Phe Thr Pro Leu Ile Glu Arg Asn Thr Thr Ile Pro Thr Lys Lys
            405                 410                 415

Ser Gln Val Phe Ser Thr Ala Glu Asp Gly Gln Thr Ala Val Thr Ile
            420                 425                 430

Lys Val Tyr Gln Gly Glu Arg Lys Met Ala Ile Asp Asn Lys Leu Leu
            435                 440                 445

Gly Gln Phe Ser Leu Glu Gly Ile Pro His Ala Pro Arg Gly Val Pro
        450                 455                 460

Gln Ile Glu Val Thr Phe Asp Ile Asp Ala Asn Gly Ile Val His Val
465                 470                 475                 480

Ser Ala Lys Asp Lys Ala Ser Gly Lys Glu Gln Thr Ile Lys Ile Gln
            485                 490                 495

Ser Ser Gly Gly Leu Ser Asp Glu Glu Ile Lys Lys Met Val Lys Asp
            500                 505                 510

Ala Gln Asp Arg Ala Glu Asp Asp Glu Lys Arg Lys His Val Glu
            515                 520                 525

Leu Lys Asn Ser Ser Gly Leu Ile His Ser Val Glu Lys Ser Leu
530                 535                 540

Lys Asp Tyr Gly Asp Lys Val Ala Gly Ala Asp Lys Ser Asn Ile Glu
545                 550                 555                 560

Ser Ala Ile Lys Asp Leu Arg Glu Cys Leu Asn Asp Ser Asn Cys Ser
            565                 570                 575

Thr Asp Thr Leu Gln Gln Lys Tyr Asp Ala Leu Met Asn Leu Ser Met
            580                 585                 590

Lys Leu Gly Glu Ala Ala Tyr Ala Ala Asn Lys Asn Asp Gly Ala Gly
            595                 600                 605

Ser Ala Asp Gln Ser Gly Ser Ser Ser Gly Gly Ser Asp Gly Asn Pro
        610                 615                 620

Glu Glu Arg Val Val Asp Ser Glu Tyr Gln Gly Ile Asn Lys Asp Glu
625                 630                 635                 640

Asp Lys Lys Asn Thr
            645

<210> SEQ ID NO 63
<211> LENGTH: 453
<212> TYPE: PRT
<213> ORGANISM: Anaplasma phagocytophilum

<400> SEQUENCE: 63

Met Lys Ala Thr Leu Ile Thr Cys Tyr Thr Gln Val Cys Val Cys Tyr
1               5                   10                  15

Gly Tyr Val Met His Ser Ser Met Ile Tyr Asn Ser Lys Thr Tyr Arg
            20                  25                  30

Val Tyr Ser Arg Val Ala Gly Glu Ile Lys Asp Asp Arg Leu Thr His

```
            35                  40                  45
Arg Ala Val Ala Val Tyr Cys Ser Trp Leu Leu Glu Arg Ser Ile Asn
 50                  55                  60
Glu Leu Arg Ala Val Leu Glu Thr Ser Gly Pro Asp Gly Tyr Val Phe
 65                  70                  75                  80
Val Gln Leu Ala Leu Asp Arg Met Glu Glu Val Tyr Asn Asp Ile Tyr
                 85                  90                  95
Gln Ala Arg Ala Gly Thr His Asp Asp Ile Val Lys Ala Leu Ser Ala
                100                 105                 110
Asn Cys Asp Gln Tyr Leu Phe Gln Cys Arg Ser Ala Leu Phe His Leu
                115                 120                 125
Ser Arg Phe Arg Asp Gly Ser Leu Pro Leu Glu Gly Pro Val Gly Asp
            130                 135                 140
Asp Val Ser Ser Phe Cys Thr Ala Ser Ser Asn Ile Ala Ser Val Ile
145                 150                 155                 160
Thr Leu Leu Gln Thr Asn Arg Ser Leu Pro Asp Arg Val Ser Ser Asp
                165                 170                 175
Thr Arg Asn Arg Leu Cys Met Leu Ile Asp Ser Leu Ser Asp Ser Val
                180                 185                 190
Thr Ala Met Pro Asp Ser Ala Phe Met His Leu Ala Gln Gly Ser Ala
            195                 200                 205
Gly Phe Ala Ser Val Tyr Asp Ala Arg Cys Ala Phe Leu Phe Ala Val
210                 215                 220
Glu Glu Leu Arg Ala Leu Ala Tyr Thr Val His Thr Asp Thr Asp Thr
225                 230                 235                 240
Ala Ala Arg Val Cys Leu Gly Asp Ser Phe Glu Ala Leu Leu Glu Asn
                245                 250                 255
Ile Arg Glu Ala Ile Arg Arg Val Ser Asp Ala Pro Gly Val Thr Ala
                260                 265                 270
Arg Ala Ser Cys Ser Cys Thr Leu Ala Asn Lys Ala Leu Ala Arg Ile
            275                 280                 285
Gln Ala Met Phe Glu Asn Tyr Val Asn Gly Thr His Ala Arg Asp Ser
290                 295                 300
Asp Leu Ser Asp Glu Met Tyr Met Ser Thr Thr Ile Val Ser Ala Tyr
305                 310                 315                 320
Ala Ala Ala Arg Ser Leu Cys Tyr Ser Cys Ile Ser Ala Ala Ser Glu
                325                 330                 335
Leu Pro Cys Val Pro Ser Ile Ile Glu Cys Ser Ser Ala Leu Tyr Asp
                340                 345                 350
Leu Tyr Ser His Leu Ser Ala Arg Ala Phe Ile Asp Leu Ala Asp Pro
            355                 360                 365
His Asp Val Asn Asn Ile Leu Pro Ala Leu Asn Lys Ala Arg Glu Ala
            370                 375                 380
Leu Gly Lys Val Asp Arg Ser Thr Leu Pro Ser Asn Arg Asp Thr Glu
385                 390                 395                 400
Ile Tyr Asp Arg Leu Arg Lys Ala Ile Glu Gln Ala Ser Gly Arg Cys
                405                 410                 415
Ile Met Arg Gln Leu Glu Pro Asp Tyr Leu Asp Leu Ala Pro Ser Thr
                420                 425                 430
Gly Gln Asn Asp Leu Ser Ile Glu Gly Leu Gly Ala Ala Gly Ala Ser
            435                 440                 445
His Asp Leu His His
            450
```

<210> SEQ ID NO 64
<211> LENGTH: 442
<212> TYPE: PRT
<213> ORGANISM: Anaplasma phagocytophilum

<400> SEQUENCE: 64

```
Met Cys Val Cys Tyr Gly Ala Val Met His Ser Phe Ile Asp Pro Ile
1               5                   10                  15

Ser Lys Thr Tyr Arg Val Tyr Ser Asn Val Glu Glu Ser Leu Arg Ser
            20                  25                  30

Gly Glu Phe Thr Glu Arg Ala Val Ala Val Arg Thr Ser Trp Leu Leu
        35                  40                  45

Glu Gln Ala Leu Glu Arg Leu His Arg Val Val Glu Ala Ser Glu Glu
    50                  55                  60

Gly Ile Pro Ser Ser Leu Val Lys Met Ala Leu Gln Asn Val Arg Asp
65                  70                  75                  80

Ile Tyr Ser Asn Ile Tyr Arg Ala Arg Glu Gly Thr Ala Asn Asn Ile
                85                  90                  95

Lys Lys Ala Leu Val Asp Asn Gly Arg Glu His Ile Ser Lys Leu Arg
            100                 105                 110

Thr Val Leu Leu Tyr Leu Ala Leu Ala Arg Ser Lys Ser Leu Pro Asn
        115                 120                 125

Glu Gly Pro Ala Gly Ala Ser Val Thr Glu Ile Ser Ala Ala Ser Tyr
    130                 135                 140

Asn Ala Ala Ser Ala Leu Ser Ile Leu Gln Ser Asn Leu Gly Leu Pro
145                 150                 155                 160

Asp Glu Ala Ser Val Asn Thr Arg Asp Arg Leu Cys Val Leu Leu Asp
                165                 170                 175

Ser Leu Ser Gly Thr Ile Glu Leu Ile Pro Gly Arg Ala Leu Leu Arg
            180                 185                 190

Ser Val Arg Gly Ser Thr Gly Phe Ile Ser Pro Ser Glu Val Arg Asn
        195                 200                 205

Ala Leu Leu Leu Ala Val Glu Glu Ala His Ala Leu Val Tyr Thr Thr
    210                 215                 220

His Asp Ser Ala Asp Lys Asp Ala Arg Gly Cys Val Gln Gly Ala Leu
225                 230                 235                 240

Glu Leu Val Leu Tyr Ser Ile Lys Arg Val Ile Cys Gly Ile Arg Gly
                245                 250                 255

Lys Asn Ile Ser Ser Arg Ala Ser Trp Ser Cys Ala Leu Ala Ser Gln
            260                 265                 270

Met Met Tyr Thr Ile Gln Glu Val Phe Asp Gly Tyr Val Ser Asn Thr
        275                 280                 285

His Thr Arg Asp Ser Asp Val Ser Asp Lys Glu Phe Leu Ser Asn Asn
    290                 295                 300

Val Ile Arg Ala Phe Thr Ser Ala Arg His Leu Leu Ala Ser Cys Val
305                 310                 315                 320

Ser Val Pro Pro Glu Glu Arg Pro Ser Ser Glu Tyr Val Ile Arg
                325                 330                 335

Cys Ser Gly Met Leu Arg Glu Val Tyr Ser His Leu Gly Thr Cys Glu
            340                 345                 350

Ser Ile Asp Leu Ala Asn Pro His Gly Ala Asn Asn Ile Leu Pro Ala
        355                 360                 365

Leu Asn Lys Ala Arg Glu Ala Leu Asp Glu Val Asp Pro Ser Asp Leu
```

```
                  370                 375                 380
Pro Ser His Arg Asp Ala Glu Thr Tyr Ser Arg Ile Arg Glu Ala Ile
385                 390                 395                 400

Met Gln Ala Ser Arg Arg Cys Ile Met Gln Gln Cys Ser Glu Pro Asp
                405                 410                 415

Leu Leu Asp Ser Ala Leu Gly Ala Gly Trp Asp Ala Leu Ser Ile Glu
                420                 425                 430

Gly Leu Gly Ala Gly Cys Trp Arg Phe Ser
                435                 440

<210> SEQ ID NO 65
<211> LENGTH: 1047
<212> TYPE: PRT
<213> ORGANISM: Anaplasma phagocytophilum

<400> SEQUENCE: 65

Met Ala Lys Arg Phe Leu Asn Asp Thr Glu Lys Lys Leu Leu Ser Leu
1               5                   10                  15

Leu Lys Ser Val Met Gln His Tyr Lys Pro Arg Thr Gly Phe Val Arg
                20                  25                  30

Ala Leu Leu Ser Ala Leu Arg Ser Ile Ser Val Gly Asn Pro Arg Gln
            35                  40                  45

Thr Ala His Asp Leu Ser Val Leu Val Thr Gln Asp Phe Leu Val Glu
50                  55                  60

Val Ile Gly Ser Phe Ser Thr Gln Ala Ile Ala Pro Ser Phe Leu Asn
65                  70                  75                  80

Ile Met Ala Leu Val Asp Glu Glu Ala Leu Asn His Tyr Asp Arg Pro
                85                  90                  95

Gly Arg Ala Pro Met Phe Ala Asp Met Leu Arg Tyr Ala Gln Glu Gln
            100                 105                 110

Ile Arg Arg Gly Asn Leu Leu Gln His Arg Trp Asn Glu Glu Thr Phe
        115                 120                 125

Ala Ser Phe Ala Asp Ser Tyr Leu Arg Arg Arg His Glu Arg Val Ser
    130                 135                 140

Ala Glu His Leu Arg Gln Ala Met Gln Ile Leu His Ala Pro Ala Ser
145                 150                 155                 160

Tyr Arg Val Leu Ser Thr Asn Trp Phe Leu Leu Arg Leu Ile Ala Ala
                165                 170                 175

Gly Tyr Val Arg Asn Ala Val Asp Val Val Asp Ala Glu Ser Ala Gly
            180                 185                 190

Leu Thr Ser Pro Arg Ser Ser Glu Arg Thr Ala Ile Glu Ser Leu
        195                 200                 205

Leu Lys Asp Tyr Asp Glu Glu Gly Leu Ser Glu Met Leu Glu Thr Glu
    210                 215                 220

Lys Gly Val Met Thr Ser Leu Phe Gly Thr Val Leu Leu Ser Thr Tyr
225                 230                 235                 240

Val Asn Glu Leu Arg Ala Glu Val Ala Gln Glu Phe Ala Glu His His
                245                 250                 255

Arg Phe Leu Ser Arg Val Leu Ser Thr Cys Ser Ala Leu Leu Ser Pro
            260                 265                 270

Leu Gly Thr Val Ala Val Val Ala Tyr Cys Ala Ser Met Phe Ser Ser
        275                 280                 285

Ile Ile Gln Gln Ala Thr Asn Pro Ser Ser Asp Lys Glu Lys Tyr Cys
    290                 295                 300
```

```
Ala Leu Ile Asp Tyr Ile Asn Glu Thr Ile Ala Ser Phe Gly Ser Gly
305                 310                 315                 320

Asn Gly Asn Ala Thr Ile Thr Glu Ala Leu Ile Arg Gly Ser Asn Leu
            325                 330                 335

Thr Ala Leu Phe Gly Asn His Ser Cys Ser Glu Ser Asn Glu Ala Leu
            340                 345                 350

His Asp Ile Leu Ser Asn Arg Arg Asn Glu Ser Leu Ser Ile Thr Asn
            355                 360                 365

Met Ser Ala Met Pro Ala Ser Ile Ser Val Leu Thr Thr Met Tyr Leu
370                 375                 380

Ala Leu Pro Ile Ile Ala Phe Gly Gly Tyr Ala Ala Gln Trp Val Ser
385                 390                 395                 400

Arg Arg Met Ser Ser Arg Gly Arg Gly Phe Ser Ser Pro Glu Met
            405                 410                 415

Phe Ser Met Leu Ser Ala Val Val Cys Ala Lys Leu Gly Leu Asn Thr
            420                 425                 430

Phe Leu Thr Leu Thr Ala His Val Ser His Lys Ala Phe Ser Thr Ala
            435                 440                 445

Leu Asn Trp Ser Val Thr Arg Leu Phe Leu Pro Leu Ser Leu Ile Glu
450                 455                 460

Gln Pro Lys Lys Ile Gly Leu Phe Val Asn Ser Ala Met Ser Ala Ala
465                 470                 475                 480

Trp Ser Ser Arg Arg Leu Arg Phe Glu Pro Ser Ser Arg Ala Cys Ala
            485                 490                 495

Ile Ala Ala Ala Leu Ser Ile Pro Phe Glu Tyr Ala Gly His Val Val
            500                 505                 510

Ala Lys Leu His Val Ile Asn Thr Gly Trp Thr Gln Val Pro Pro Ser
            515                 520                 525

Cys Arg Gln Ile Leu Asn Phe Thr Val Lys His Ala Arg Val Ala Ala
530                 535                 540

Phe Phe Gly Thr Ile Ile Ala Ala Arg Arg His Ile Arg Asn Met Pro
545                 550                 555                 560

Tyr Ser Arg Arg Leu Glu Arg Ile Ile Trp Ala Asp Gly Val Lys Ala
            565                 570                 575

Thr Thr Ala Pro Ala Ala Leu Leu Leu Asp Val Ala Ala Gly Asn
            580                 585                 590

Val Phe Leu Ser Thr Val Val Leu Thr Val Asp Ser Leu Val Ser Leu
            595                 600                 605

Ile Pro Asp Met Ile Cys Ser Ala Asn Val Asp Met Leu Asn Asn Ala
610                 615                 620

Gly Asn Gln Leu Ala Ala Leu Glu Gln Trp Leu Val Glu Asn Leu Asp
625                 630                 635                 640

Glu Glu Ala Leu Leu Lys Ile Ala Met Leu Thr Ser Leu Gln Arg Leu
            645                 650                 655

Pro Gly Ser Thr His Gly Glu Leu Glu Lys Ile Leu Glu Glu Phe Tyr
            660                 665                 670

Asn Lys Asp Gln Ile Thr Asp His Gly Val Asp Leu Thr Val Asp Asp
            675                 680                 685

Asp Phe Thr Glu Gly Ile Thr Glu Arg Gln Leu Leu Glu Trp Gln Ser
            690                 695                 700

Asp Asp Ala Ser Arg Arg Arg Thr Arg Gly Gly Asp Cys Ala Asp Ala
705                 710                 715                 720

Ser Ser Glu Gly Glu Leu Ile Gly Ala Thr Ser Arg Asp Tyr Tyr Asp
```

```
                725                 730                 735

Pro Pro Glu Arg Arg Gly Pro Thr Leu Tyr Glu Glu Leu Val Arg
            740                 745                 750

Gly Ile Leu Glu Arg His Gly Thr Arg Phe Ser Asp Ala Leu Ala Gly
        755                 760                 765

Glu Glu Glu Asp Ala Asp Glu Ala Leu Leu Phe Ser Asp Leu Arg Leu
    770                 775                 780

Gln Leu Asp Asp Ala Ala Val Pro His Glu Glu Gln Ser Glu Arg Gly
785                 790                 795                 800

Arg Ser Ser Arg Arg Gly Arg Phe Cys Gly Asp Glu Asp Phe Asp Val
                805                 810                 815

Lys Cys Gln Gly Gln Gly Asp Gly Arg Arg Ser Arg Arg Ser Asp Arg
            820                 825                 830

Arg Gly Tyr Ser Glu Glu Pro Ala Leu Gly Asp Met Arg His Ser Ser
        835                 840                 845

Arg Gly Ala Ala Ser Glu Ser Asp Ala Arg Arg Ser Arg Arg Ser Asp
    850                 855                 860

Arg Glu Glu Pro Ala Thr Ser Pro Arg Arg His Pro Ala Gly Glu Val
865                 870                 875                 880

Pro Gln Arg Gln Asp Glu Ala Ser Pro Ser Gly Leu Arg Asn His Pro
                885                 890                 895

Ser Gly Ala Ile Pro Lys Val Arg Ser Ala Ser Ala Met His Thr
            900                 905                 910

Lys Lys Asp Lys Ser Lys Lys Ser Ala Arg Ser Ser Glu Ser Thr Arg
        915                 920                 925

Arg Gly Val Asp Leu Gly Phe Leu Gly Ser Pro Lys Asp Leu Glu Arg
    930                 935                 940

Cys Val Leu Glu Gly Glu Arg Ala Arg Ala Arg Ser Pro Arg Cys Gly
945                 950                 955                 960

Val Gly Thr Pro Pro Cys His Leu Asp Arg Val Val Tyr Glu Thr Glu
                965                 970                 975

Gly Ala Gln Asp Val Asp Asn Asp Val Phe Asp Val Ser Arg Tyr Val
            980                 985                 990

Thr Pro Arg Asn Gln Ala Gly Glu Arg Val Arg Val Gly Thr Ser Ser
        995                1000                1005

Ser Ser Arg Ala Pro Gln Gly Ala Thr Gly Leu Ala Pro Gly Thr
    1010                1015                1020

Ser Leu Thr Ser Leu Asp Asp Asp Ala Leu Asp Ile Leu Asp Ala
    1025                1030                1035

Ile Gln Gly Gln Arg Gly Arg Arg
    1040                1045

<210> SEQ ID NO 66
<211> LENGTH: 1528
<212> TYPE: PRT
<213> ORGANISM: Anaplasma phagocytophilum

<400> SEQUENCE: 66

Met Thr Leu Leu Leu Lys Gln Asn Pro Pro Lys Ala Ser Val Ala Leu
1               5                   10                  15

Leu Gly Ser Ala Ile Asp Phe Phe Leu Cys Arg Asp Arg Asn Ser His
            20                  25                  30

Pro Ala Arg Arg Arg Met Val Ile Leu Leu Ala Glu Gly Phe Thr Leu
        35                  40                  45
```

```
Arg Glu Gly Ser Ala Val Pro Pro Ala Leu Ile His Glu Asn Leu Thr
     50              55                  60

Ser Pro Asp Leu Leu Ala Arg Ala Leu His Lys Thr Ala Ser Asn Ser
 65              70                  75                      80

Thr Ala Phe Gln Gln Val Pro Phe Gln Leu Trp His Ala Leu Ala Leu
                 85                  90                  95

Ala Tyr Asn Ser Leu Pro Gly Lys Asn Gln Glu Asp Leu Thr Asn
             100             105             110

Phe Val Leu Gly Cys Leu Asp Gly Val Ser Glu Asp Met Thr Ile Val
             115             120             125

Arg Glu Glu Asp Ser Thr Thr Phe Glu Val Gln Ser Tyr Thr Thr Phe
         130             135             140

Ser Arg Val His Ser Leu Leu Ala Ser Ala Pro Ser Ser Tyr Lys Asn
145             150             155                         160

Gly Ala Leu Thr Val His Glu Ser Cys Ile Phe Ser Ile Gln Asp Lys
                 165             170             175

Ser Gly Val Pro Ile Ala Lys Val Lys Met Trp Val Glu Tyr Asp Ile
             180             185             190

Ala Pro Ser Thr Lys Ala Glu Gly Val Tyr Arg Thr Ala Val Lys Lys
         195             200             205

Val Lys Leu Val Leu Thr Glu Arg Asp Cys Arg Asp Val Arg Gln Gly
210             215             220

Glu Pro Gly Ser Val Cys Ser Trp His Asn Ile Pro Lys Ala Leu Ala
225             230             235                         240

Lys His Tyr Val Arg Val Pro Glu Arg Pro Thr His Val Leu Tyr Ser
                 245             250             255

Ala Cys Asn Leu Gln Arg His Asn Pro Arg Tyr Met Ala Arg Arg Val
             260             265             270

Phe Tyr Asp Val Ser Gly Ile Asp Glu Cys Ile Leu Arg Ala Tyr Ser
         275             280             285

Val Ile Ser Gly Met Pro Pro Glu Val Leu Glu Leu Ser Phe Cys Asn
         290             295             300

Thr Val Ile Ser Gln Glu Ala Ser Gly Val Phe Arg Val Val Arg
305             310             315             320

Gly Val Val Gly Leu Val Gly Tyr Asp Lys Ser Ser Val Val Gln Gln
                 325             330             335

Gly Ala Val Ser His Gly Arg Asp Ala Val Ser Lys Met Gly Val Cys
             340             345             350

Met Ser Phe Val Ala Ser Gln Ala His Asp Ala Cys Ala Thr Ile Leu
         355             360             365

Arg His Val Ala Val Thr Val Asn Thr Phe Gly Asn Val Leu Thr Leu
     370             375             380

Gly Gly Gly Ile Ser Leu Arg Asp Phe Leu Ala Gly Ser Ala Lys Asp
385             390             395                         400

Thr Asp Phe Ala Gly Ser His Ile Cys Asn Phe Gly Glu Glu Ile Val
                 405             410             415

Ala His Gly Leu Ser Leu Trp Glu Asp Leu Gly Lys Arg His Arg Trp
             420             425             430

Ala Ser His Ser Val Pro Val Arg Gly Asp Cys Gly Ile Phe Ile Gln
             435             440             445

His Ser Asp Glu Ile Arg Glu Ile Leu Arg Ser Gln Pro Lys His Ala
     450             455             460

Ala Asn Ile Val Glu Lys Thr Gly Val Asn Thr Glu Asn Leu Arg Val
```

-continued

```
            465                 470                 475                 480
        Leu Leu Ser Ser Ile Leu Ser Asn Ser Ser Gly Ser Ser Leu Pro Val
                        485                 490                 495
        Glu Leu Ala Ala His Tyr Val Ala His Glu Gly Val Val Ala Asp Asn
                        500                 505                 510
        Gly Asp Ser Ala Arg Arg Leu Pro Val Asn Gln His Val Leu Glu Glu
                        515                 520                 525
        His Leu Val Tyr Arg Val Thr Ser Val Ser Gly Ile His Ile His Ala
                        530                 535                 540
        Cys Val Asp Tyr Val Val Glu Asp Ile Asp Thr Pro Gly Ser Val Lys
        545                 550                 555                 560
        Asp Leu Gly Leu Cys Ile Arg Asp Val Arg Ile Gly Thr Arg Val Ala
                        565                 570                 575
        Ser Ser Ala Glu Glu Val Cys Ser Ala Ile Gln Glu Lys Glu Gly Arg
                        580                 585                 590
        Ile Asp Arg Asn Asp Phe Ala Trp Phe Asn Val Asp Gln Ser Leu Val
                        595                 600                 605
        Glu Thr Ser Arg Ala Glu Phe Arg Ala Ala Ile Gly Thr Leu Pro Ile
                        610                 615                 620
        Leu Pro Ser Thr Arg Ser Leu Leu Ser Ser Asp Leu Thr Tyr Phe Ser
        625                 630                 635                 640
        Arg Asp Cys Ser Lys Ile Glu Asn Ala Val Lys Glu Arg Met Leu Pro
                        645                 650                 655
        Ala Leu Thr Leu Tyr Ala Lys Lys Ile Ala Lys Arg Asn Ala Glu Gly
                        660                 665                 670
        Met Leu Arg Val Thr Gly Asp Pro Leu Arg Gly Ser Ala Asp Thr Arg
                        675                 680                 685
        Trp Leu Ala Gln Met Leu Glu Ser Gly Lys Val Leu Val Gln Ser Pro
                        690                 695                 700
        Asn Ile Leu Ser Met Glu Glu Asp Gly Thr Ala Phe Val Ser Pro Asn
        705                 710                 715                 720
        Phe Asn Pro Ala Lys Cys Glu Glu Asp Asp Val Arg Glu Ala Gly Gly
                        725                 730                 735
        Val Arg Ala Arg Leu Ala Ala Thr Leu Gln Asn Met Leu Gly Asp Pro
                        740                 745                 750
        Arg Ile His Val Ala Ile Ser Glu Ala Ile Val Ser Met Ser Asp Val
                        755                 760                 765
        Arg Gly Thr Asp Leu Val Arg Leu Cys Arg Glu Leu Ile Cys Thr Thr
                        770                 775                 780
        Met Leu Ser Lys Lys Cys Ala Val Gln Val Val Asp Thr Gly Leu Arg
        785                 790                 795                 800
        Ile Ile Pro Asp Val Gln Gln Gly Gly Thr Gly Thr Leu Arg Leu Tyr
                        805                 810                 815
        Gln His Val Leu Phe Ala Pro Val Ala Trp Trp Ile Glu Lys Pro Ile
                        820                 825                 830
        Ala Ile His Leu Val Val Arg Ser Asp Leu Val Ile His Arg Asp Leu
                        835                 840                 845
        Thr Gly Ala Leu Ala Phe Asn Ile Glu Ser Val Arg Phe Gly Leu Arg
                        850                 855                 860
        Ala Ser Gln Asn Thr Val Leu Ser Thr Ser Ala Leu Leu Leu Glu Cys
        865                 870                 875                 880
        Lys Pro Ser Leu Leu Gly Leu Cys Cys Thr Val Asp Val Gln Pro Ser
                        885                 890                 895
```

-continued

Glu Glu Glu Gly Val Tyr Ser Ser Arg Ala Leu His Val Met Ala Ala
              900                 905                 910

Ile Gln Arg Tyr Tyr Gly Ser Ala Tyr Ser Phe Leu Leu Val Asp Pro
              915                 920                 925

Leu Glu Asp Thr Arg Ser Thr Asn Asp Ser Leu Leu Leu Val Arg
    930                 935                 940

Thr Gly Ile Gly Glu Phe Leu Asn Val Phe Gly Val Asp Gly Val Val
945                 950                 955                 960

Arg His Pro Leu Leu Cys Phe Thr Asp Ser Ser Gln Asp Val Asp Glu
              965                 970                 975

His Pro Thr Ser Glu Gln Asp Ile Tyr Asn Trp Ile Ser Lys Asn Tyr
              980                 985                 990

Pro Arg His Gly Asp Asp Ile Gly Gly Ile Ile Ser Glu Ala Leu Phe
              995                 1000                1005

Asn Ala Thr Gly Phe Gly Asn Val Cys Lys Phe Leu Arg Phe Ser
    1010                1015                1020

Val Gly Pro Asn Leu Glu Ile Thr Pro Val Glu Arg Gly Gly Tyr
    1025                1030                1035

Arg Asn Pro Gln Asp Val Ser Gly Val Ile Ala Ser Gly Pro Asp
    1040                1045                1050

Gly Leu Phe Thr Ala Arg Pro Tyr Leu Val Lys Leu Arg Lys Gly
    1055                1060                1065

Ser Glu Thr Ser Thr Leu Gly Leu Val Cys Thr Cys Asn Ile Ser
    1070                1075                1080

Val Arg Pro Gly Gly Asn Asn Glu Ile Leu Val Gln Val Arg Gly
    1085                1090                1095

Leu Lys Val Ser Leu Cys Ser Gly Lys Asn Leu Leu Lys Phe Phe
    1100                1105                1110

Leu Ser Thr Ser Thr Asp Gln Gly Ile Tyr His Glu Gln Tyr Ser
    1115                1120                1125

Glu Phe Leu His Ser Leu Glu Pro Cys Ser Asp Leu Ser Glu His
    1130                1135                1140

Cys Leu Gln Ala Arg Val Gln Ser Ala Lys Leu Ala Asn Tyr Val
    1145                1150                1155

Arg Arg Lys Gln His Pro Gly Ile His Thr Gln His Glu His Ala
    1160                1165                1170

Pro Gly Gly Pro Lys Ala Ser Asp Ala Gly Ser His Thr Met Lys
    1175                1180                1185

Arg His Gly Arg Val Leu Pro Thr Pro Met Asp Pro Lys Val Leu
    1190                1195                1200

Gln Asp Leu Arg Ser Ser Asn Leu Leu Ala Ala Ala Phe Gly Gly
    1205                1210                1215

Glu Arg Phe Pro Glu Asn Asp His Ile Leu Arg Thr Met Lys Ala
    1220                1225                1230

Leu Val Asp Val Ala Ser Arg Gly Gln Ile Ile Cys Ala Ser Pro
    1235                1240                1245

Glu Arg Gly His Lys Gly Ala Leu Tyr Thr Asn Val Ala Arg Met
    1250                1255                1260

Ser Glu Asn Arg Leu Trp Val Leu His Asn Ala Cys Phe Met Thr
    1265                1270                1275

Pro Asp Leu Arg Val Leu Met Val Glu Leu His Tyr Lys Val Asp
    1280                1285                1290

```
Arg Lys Lys Ser Pro His Gly Gly Arg Asp Ile Phe Glu Ile Cys
1295                1300                1305

Asp Gly Ser Phe Asn Val Ala Ser Gly Asp Thr Pro Ser Lys Lys
1310                1315                1320

Asp Phe Ser Ile Arg Ile Pro Lys Asn Val Gln Val Ser Glu Asn
1325                1330                1335

Lys Trp Asn Ile Phe Ser Glu Met Leu Lys Pro Pro Val Val Pro
1340                1345                1350

Glu Ser Phe Leu Asp Lys Met Cys Arg Trp Leu Thr Thr Ala Trp
1355                1360                1365

Asn Ser Leu Lys Ser Phe Val Ser Asn Ala Gly Gly Tyr Val Met
1370                1375                1380

Arg Leu Phe Arg Ala Cys Cys Ser Cys Val Arg Pro Gln Asn Val
1385                1390                1395

Ser Glu Asp Asn Val Thr Leu Leu Asp Ser Asn Arg Asp Ser His
1400                1405                1410

Glu Cys Glu Ser Ala Val Ser Glu Val Ser Ala Pro Ala Pro Val
1415                1420                1425

Ile Gly Thr Ser Ser Glu His Val His Ser Asn Asp Val Asp Thr
1430                1435                1440

Ala Gln Ser Ser Thr Lys Ala Lys Gly Thr Asp Gly Lys Lys Pro
1445                1450                1455

Ser Thr Thr Val Pro Lys Lys Pro Pro Arg Pro Ala Arg Gly Ala
1460                1465                1470

Lys Ser Ser Ser Ala His Ser Val Ala Gly Val Thr Gln Gly Gly
1475                1480                1485

Ala Gly Asp Val Thr Arg Glu Val Gly Gly Pro Ser Thr Ser Val
1490                1495                1500

Ala Asp Pro Thr Ala Ala Ser Ser Val Ser Gln Leu Gln Ser Ser
1505                1510                1515

Arg Ala Ser Asn Val Ser Gln Gln Gln His
1520                1525

<210> SEQ ID NO 67
<211> LENGTH: 416
<212> TYPE: PRT
<213> ORGANISM: Anaplasma phagocytophilum

<400> SEQUENCE: 67

Met Val Cys Cys Val Ser Arg Val Val Leu Tyr Ile Ala Ser Val Ile
1               5                   10                  15

Leu Leu Met Leu Ile Met Gly Glu Asp Ala Ser Ala Ala Ile Tyr Lys
                20                  25                  30

Asp Asp Leu Pro Pro Asn Ser Lys Phe Tyr Val Ala Leu Asp Tyr
                35                  40                  45

Ala Pro Ala Leu Ser Arg Val Ser Thr Phe Asp Ile Val Gly Asp Gly
            50                  55                  60

Lys Thr His Ile Ala Leu Pro Tyr Leu Lys Asn Asp Gln Glu Asp Arg
65                  70                  75                  80

Phe Asn Ala Glu Ala Ile Asp Trp Asp Ala Pro Asn Leu Ser Val Gln
                85                  90                  95

Phe Lys Asn Ser Val Leu Met Ser Trp Val Gly Ser Ile Gly Tyr Lys
                100                 105                 110

Met Met Gly Gly Arg Leu Glu Leu Glu Val Gly His Glu Lys Phe Gly
            115                 120                 125
```

```
Ala Arg Val Ser Ser Gly Glu Asn Arg Glu Asn Ser Asp Val Ala
            130                 135                 140

Tyr Val Phe Phe Ser Arg Leu Leu Pro Tyr Tyr Leu Val Ser Ala Gln
145                 150                 155                 160

Tyr Glu Lys Leu Ile Ser Gly Leu Ala Asn Leu Thr Glu Asp Glu Ile
                165                 170                 175

Leu Ala Phe Ala Asn Gly Val Ala Asp Gln Arg Pro Asp Leu Asp Lys
            180                 185                 190

Lys Ile Cys Lys Lys Ala Arg Leu Gly Gly Asp Asp Arg Gly Thr Asp
            195                 200                 205

Ala Gln Ala Ala Cys Arg Asp Ser Ile Lys Gly Ala Asp Val Gly Gly
            210                 215                 220

Phe Gly Ala Phe Met Arg Lys Ala Ile Gly Thr Tyr Leu Met Trp Arg
225                 230                 235                 240

Tyr Asn Gly Gly Ser Asp Arg Tyr Gly Leu Glu Arg Gly Gly Arg Ser
                245                 250                 255

Val Asn Ser Lys Asp Ile Val Ser Asp Ile Lys Glu Leu Pro Lys Glu
            260                 265                 270

Glu Arg Lys Ile Leu Ala Gly Ile Leu Ala Ala Thr Gly Tyr Gly
            275                 280                 285

Val Val Val Glu Ile Pro Ser Val Ala Ala Thr Ser Val Met Val Asn
290                 295                 300

Ala Cys Tyr Asp His Asn Val Ser Leu Thr Arg Lys Arg Ala Ser Ala
305                 310                 315                 320

Tyr Ser Cys Val Gly Leu Gly Ser Thr Phe Val Glu Ile Val Asp Glu
                325                 330                 335

His Arg Ala Ala Lys Leu Ala Tyr Arg Leu Lys Ala Gly Leu Ser Tyr
            340                 345                 350

Asn Phe Ala Ser Gly Val Thr Ala Phe Val Gly Gly Phe Tyr His His
            355                 360                 365

Ile Ile Gly Asp Ser Trp Tyr Asp Arg Val Pro Met Arg Thr Val Phe
370                 375                 380

Leu Asp Glu Lys Thr Gly Glu Arg Pro Val Lys Thr Gly Lys Val Asp
385                 390                 395                 400

Leu Ser Leu Asp Tyr Ile Gly Ala Glu Cys Gly Ile Arg Leu Ile Leu
                405                 410                 415

<210> SEQ ID NO 68
<211> LENGTH: 134
<212> TYPE: PRT
<213> ORGANISM: Anaplasma phagocytophilum

<400> SEQUENCE: 68

Met Lys Gly Lys Ser Asp Ser Glu Ile Arg Thr Ser Ser Ser Ile Arg
1               5                   10                  15

Thr Ser Ser Ser Asp Asp Ser Arg Ser Ser Asp Ser Thr Arg Ile
                20                  25                  30

Arg Ala Ser Lys Thr His Pro Gln Ala Pro Ser Asp Asn Ser Ser Ile
            35                  40                  45

Leu Ser Ser Glu Asp Ile Glu Ser Val Met Arg Cys Leu Glu Glu Glu
            50                  55                  60

Tyr Gly Gln Lys Leu Ser Ser Glu Leu Lys Lys Ser Met Arg Glu Glu
65                  70                  75                  80

Ile Ser Thr Ala Val Pro Glu Leu Thr Arg Ala Leu Ile Pro Leu Leu
```

85                  90                  95
Ala Ser Ala Ser Asp Ser Asp Ser Ser Ser Arg Lys Leu Gln Glu Glu
            100                 105                 110

Trp Val Lys Thr Phe Met Ala Ile Met Leu Pro His Met Gln Lys Ile
        115                 120                 125

Val Ala Ser Thr Gln Gly
    130

<210> SEQ ID NO 69
<211> LENGTH: 32
<212> TYPE: DNA
<213> ORGANISM: Artificial Sequence
<220> FEATURE:
<223> OTHER INFORMATION: Synthetic primer

<400> SEQUENCE: 69
caccttgagt tttacaatgt cgaagttatc gc                                    32

<210> SEQ ID NO 70
<211> LENGTH: 29
<212> TYPE: DNA
<213> ORGANISM: Artificial Sequence
<220> FEATURE:
<223> OTHER INFORMATION: Synthetic primer

<400> SEQUENCE: 70
ctatcctagc atccttctag aagcggaag                                        29

<210> SEQ ID NO 71
<211> LENGTH: 34
<212> TYPE: DNA
<213> ORGANISM: Artificial Sequence
<220> FEATURE:
<223> OTHER INFORMATION: Synthetic primer

<400> SEQUENCE: 71
caccatctat caaggaaatt acgaagatcg caac                                  34

<210> SEQ ID NO 72
<211> LENGTH: 15
<212> TYPE: DNA
<213> ORGANISM: Artificial Sequence
<220> FEATURE:
<223> OTHER INFORMATION: Synthetic primer

<400> SEQUENCE: 72
gagcagcatg cttta                                                       15

<210> SEQ ID NO 73
<211> LENGTH: 25
<212> TYPE: DNA
<213> ORGANISM: Artificial Sequence
<220> FEATURE:
<223> OTHER INFORMATION: Synthetic primer

<400> SEQUENCE: 73
cctcaactaa agaagcgtca tcaaa                                            25

<210> SEQ ID NO 74
<211> LENGTH: 24
<212> TYPE: DNA
<213> ORGANISM: Artificial Sequence
<220> FEATURE:
<223> OTHER INFORMATION: Synthetic primer

<400> SEQUENCE: 74
gtacggtgta caaaacgagg aaca                                          24

<210> SEQ ID NO 75
<211> LENGTH: 5
<212> TYPE: PRT
<213> ORGANISM: Artificial Sequence
<220> FEATURE:
<223> OTHER INFORMATION: Artificial linker

<400> SEQUENCE: 75

Cys Leu Asn His Leu
1               5

<210> SEQ ID NO 76
<211> LENGTH: 15
<212> TYPE: DNA
<213> ORGANISM: Artificial Sequence
<220> FEATURE:
<223> OTHER INFORMATION: Artificial linker

<400> SEQUENCE: 76
tgcctgaacc acctg                                                    15

<210> SEQ ID NO 77
<211> LENGTH: 205
<212> TYPE: PRT
<213> ORGANISM: Anaplasma phagocytophilum

<400> SEQUENCE: 77

Met Leu Arg Arg Ser Ser Phe Phe Cys Leu Leu Ala Leu Leu Ser Val
1               5                   10                  15

Thr Ser Cys Gly Thr Leu Leu Pro Asp Ser Asn Val Gly Val Gly Arg
            20                  25                  30

His Asp Leu Gly Ser His Arg Ser Val Ala Phe Ala Lys Lys Val Glu
        35                  40                  45

Lys Val Tyr Phe Asp Ile Gly Lys Tyr Asp Leu Lys Gly Pro Gly Lys
    50                  55                  60

Lys Val Ile Leu Glu Leu Val Glu Gln Leu Arg Gln Asp Asp Ser Met
65                  70                  75                  80

Tyr Leu Val Val Ile Gly His Ala Asp Ala Thr Gly Thr Glu Glu Tyr
                85                  90                  95

Ser Leu Ala Leu Gly Glu Lys Arg Ala Asn Ala Val Lys Gln Phe Ile
            100                 105                 110

Ile Gly Cys Asp Lys Ser Leu Ala Pro Arg Val Thr Thr Gln Ser Arg
        115                 120                 125

Gly Lys Ala Glu Pro Glu Val Leu Val Tyr Ser Thr Asp Ala Gln Glu
    130                 135                 140

Val Glu Lys Ala Asn Ala Gln Asn Arg Arg Ala Val Ile Val Val Glu
145                 150                 155                 160

Phe Ala His Ile Pro Arg Ser Gly Val Ala Asp Met His Ala Pro Val
                165                 170                 175

Ala Ser Ser Ile Thr Ser Glu Asn Ser Asn Ala Ser Glu Gly Glu
            180                 185                 190

Asp Met Glu Ala Ser Glu Phe Ser Ser Ala Ile Ala Asn
        195                 200                 205

<210> SEQ ID NO 78
<211> LENGTH: 205

<212> TYPE: PRT
<213> ORGANISM: Anaplasma phagocytophilum

<400> SEQUENCE: 78

```
Met Leu Arg Arg Ser Ser Phe Phe Cys Leu Leu Ala Leu Leu Ser Val
1               5                   10                  15

Thr Ser Cys Gly Thr Leu Leu Pro Asp Ser Asn Val Gly Val Gly Arg
            20                  25                  30

His Asp Leu Gly Ser His Arg Ser Val Ala Phe Ala Lys Lys Val Glu
            35                  40                  45

Lys Val Tyr Phe Asp Ile Gly Lys Tyr Asp Leu Lys Gly Pro Gly Lys
        50                  55                  60

Lys Val Ile Leu Glu Leu Val Glu Gln Leu Arg Gln Asp Asp Ser Met
65                  70                  75                  80

Tyr Leu Val Val Ile Gly His Ala Asp Ala Thr Gly Thr Glu Glu Tyr
                85                  90                  95

Ser Leu Ala Leu Gly Glu Lys Arg Ala Asn Ala Val Lys Gln Phe Ile
            100                 105                 110

Ile Gly Cys Asp Lys Ser Leu Ala Pro Arg Val Thr Gln Ser Arg
            115                 120                 125

Gly Lys Ala Glu Pro Glu Val Leu Val Tyr Ser Thr Asp Ala Gln Glu
        130                 135                 140

Val Glu Lys Ala Asn Ala Gln Asn Arg Arg Ala Val Ile Val Val Glu
145                 150                 155                 160

Phe Ala His Ile Pro Arg Ser Gly Val Ala Asp Met His Ala Pro Val
                165                 170                 175

Ala Ser Ser Ile Thr Ser Glu Asn Ser Asn Ala Ser Ala Glu Gly Glu
            180                 185                 190

Asp Met Glu Ala Ser Glu Phe Ser Ser Ala Ile Ala Asn
        195                 200                 205
```

<210> SEQ ID NO 79
<211> LENGTH: 205
<212> TYPE: PRT
<213> ORGANISM: Anaplasma phagocytophilum

<400> SEQUENCE: 79

```
Met Leu Arg Arg Ser Ser Phe Phe Cys Leu Leu Ala Leu Leu Ser Val
1               5                   10                  15

Thr Ser Cys Gly Thr Leu Leu Pro Asp Ser Asn Val Gly Val Gly Arg
            20                  25                  30

His Asp Leu Gly Ser His Arg Ser Val Ala Phe Ala Lys Lys Val Glu
            35                  40                  45

Lys Val Tyr Phe Asp Ile Gly Lys Tyr Asp Leu Lys Gly Pro Gly Lys
        50                  55                  60

Lys Val Ile Leu Glu Leu Val Glu Gln Leu Arg Gln Asp Asp Ser Met
65                  70                  75                  80

Tyr Leu Val Val Ile Gly His Ala Asp Ala Thr Gly Thr Glu Glu Tyr
                85                  90                  95

Ser Leu Ala Leu Gly Glu Lys Arg Ala Asn Ala Val Lys Gln Phe Ile
            100                 105                 110

Ile Gly Cys Asp Lys Ser Leu Ala Pro Arg Val Thr Gln Ser Arg
            115                 120                 125

Gly Lys Ala Glu Pro Glu Val Leu Val Tyr Ser Thr Asp Ala Gln Glu
        130                 135                 140
```

```
Val Glu Lys Ala Asn Ala Gln Asn Arg Arg Ala Val Ile Val Val Glu
145                 150                 155                 160

Phe Ala His Ile Pro Arg Ser Gly Val Ala Asp Met His Ala Pro Val
                165                 170                 175

Ala Ser Ser Ile Thr Ser Glu Asn Ser Asn Ala Ser Ala Glu Gly Glu
            180                 185                 190

Asp Met Glu Ala Ser Glu Phe Ser Ser Ala Ile Ala Asn
        195                 200                 205

<210> SEQ ID NO 80
<211> LENGTH: 205
<212> TYPE: PRT
<213> ORGANISM: Anaplasma phagocytophilum

<400> SEQUENCE: 80

Met Leu Arg Arg Ser Ser Phe Phe Cys Leu Leu Ala Leu Leu Ser Val
1               5                   10                  15

Thr Ser Cys Gly Thr Leu Leu Pro Asp Ser Asn Val Gly Val Gly Arg
            20                  25                  30

His Asp Leu Gly Ser His Arg Ser Val Ala Phe Ala Lys Lys Val Glu
        35                  40                  45

Lys Val Tyr Phe Asp Ile Gly Lys Tyr Asp Leu Lys Gly Pro Gly Lys
    50                  55                  60

Lys Val Ile Leu Glu Leu Val Glu Gln Leu Arg Gln Asp Asp Ser Met
65                  70                  75                  80

Tyr Leu Val Val Ile Gly His Ala Asp Ala Thr Gly Thr Glu Glu Tyr
                85                  90                  95

Ser Leu Ala Leu Gly Glu Lys Arg Ala Asn Ala Val Lys Gln Phe Ile
            100                 105                 110

Ile Gly Cys Asp Lys Ser Leu Ala Pro Arg Val Thr Thr Gln Ser Arg
        115                 120                 125

Gly Lys Ala Glu Pro Glu Val Leu Val Tyr Ser Thr Asp Ala Gln Glu
    130                 135                 140

Val Glu Lys Ala Asn Ala Gln Asn Arg Arg Ala Val Ile Val Val Glu
145                 150                 155                 160

Phe Ala His Ile Pro Arg Ser Gly Val Ala Asp Met His Ala Pro Val
                165                 170                 175

Ala Ser Ser Ile Thr Ser Glu Asn Ser Asn Ala Ser Ala Glu Gly Glu
            180                 185                 190

Asp Met Glu Ala Ser Glu Phe Ser Ser Ala Ile Ala Asn
        195                 200                 205

<210> SEQ ID NO 81
<211> LENGTH: 205
<212> TYPE: PRT
<213> ORGANISM: Anaplasma phagocytophilum

<400> SEQUENCE: 81

Met Leu Arg Arg Ser Ser Phe Phe Cys Leu Leu Ala Leu Leu Ser Val
1               5                   10                  15

Thr Ser Cys Gly Thr Leu Leu Pro Asp Ser Asn Val Gly Val Gly Arg
            20                  25                  30

His Asp Leu Gly Ser His Arg Ser Val Ala Phe Ala Lys Lys Val Glu
        35                  40                  45

Lys Val Tyr Phe Asp Ile Gly Lys Tyr Asp Leu Lys Gly Pro Gly Lys
    50                  55                  60
```

```
Lys Val Ile Leu Glu Leu Val Glu Gln Leu Arg Gln Asp Asp Ser Met
 65                  70                  75                  80

Tyr Leu Val Val Ile Gly His Ala Asp Ala Thr Gly Thr Glu Glu Tyr
                 85                  90                  95

Ser Leu Ala Leu Gly Glu Lys Arg Ala Asn Ala Val Lys Gln Phe Ile
            100                 105                 110

Ile Gly Cys Asp Lys Ser Leu Ala Pro Arg Val Thr Thr Gln Ser Arg
        115                 120                 125

Gly Lys Ala Glu Pro Glu Val Leu Val Tyr Ser Thr Asp Ala Gln Glu
    130                 135                 140

Val Glu Lys Ala Asn Ala Gln Asn Arg Arg Ala Val Ile Val Val Glu
145                 150                 155                 160

Phe Ala His Ile Pro Arg Ser Gly Val Ala Asp Met His Ala Pro Val
                165                 170                 175

Ala Ser Ser Ile Thr Ser Glu Asn Ser Asn Ala Ser Ala Glu Gly Glu
            180                 185                 190

Asp Met Glu Ala Ser Glu Phe Ser Ser Ala Ile Ala Asn
        195                 200                 205

<210> SEQ ID NO 82
<211> LENGTH: 205
<212> TYPE: PRT
<213> ORGANISM: Anaplasma phagocytophilum

<400> SEQUENCE: 82

Met Leu Arg Arg Ser Ser Phe Phe Cys Leu Leu Ala Leu Leu Ser Val
1               5                   10                  15

Thr Ser Cys Gly Thr Leu Leu Pro Asp Ser Asn Val Gly Val Gly Arg
            20                  25                  30

His Asp Leu Gly Ser His Arg Ser Val Ala Phe Ala Lys Lys Val Glu
        35                  40                  45

Lys Val Tyr Phe Asp Ile Gly Lys Tyr Asp Leu Lys Gly Pro Gly Lys
    50                  55                  60

Lys Val Ile Leu Glu Leu Val Glu Gln Leu Arg Gln Asp Asp Ser Met
 65                  70                  75                  80

Tyr Leu Val Val Ile Gly His Ala Asp Ala Thr Gly Thr Glu Glu Tyr
                 85                  90                  95

Ser Leu Ala Leu Gly Glu Lys Arg Ala Asn Ala Val Lys Gln Phe Ile
            100                 105                 110

Ile Gly Cys Asp Lys Ser Leu Ala Pro Arg Val Thr Thr Gln Ser Arg
        115                 120                 125

Gly Lys Ala Glu Pro Glu Val Leu Val Tyr Ser Thr Asp Ala Gln Glu
    130                 135                 140

Val Glu Lys Ala Asn Ala Gln Asn Arg Arg Ala Val Ile Val Val Glu
145                 150                 155                 160

Phe Ala His Ile Pro Arg Ser Gly Val Ala Asp Met His Ala Pro Val
                165                 170                 175

Ala Ser Ser Ile Thr Ser Glu Asn Ser Asn Ala Ser Ala Glu Gly Glu
            180                 185                 190

Asp Met Glu Ala Ser Glu Phe Ser Ser Ala Ile Ala Asn
        195                 200                 205

<210> SEQ ID NO 83
<211> LENGTH: 205
<212> TYPE: PRT
<213> ORGANISM: Anaplasma phagocytophilum
```

<400> SEQUENCE: 83

| Met | Leu | Arg | Arg | Ser | Ser | Phe | Phe | Cys | Leu | Leu | Ala | Leu | Leu | Ser | Val |
| 1 | | | | 5 | | | | | 10 | | | | | 15 | |

| Thr | Ser | Cys | Gly | Thr | Leu | Leu | Pro | Asp | Ser | Asn | Val | Gly | Val | Gly | Arg |
| | | | 20 | | | | | 25 | | | | | 30 | | |

| His | Asp | Leu | Gly | Ser | His | Arg | Ser | Val | Ala | Phe | Ala | Lys | Lys | Val | Glu |
| | | | 35 | | | | 40 | | | | | 45 | | | |

| Lys | Val | Tyr | Phe | Asp | Ile | Gly | Lys | Tyr | Asp | Leu | Lys | Gly | Pro | Gly | Lys |
| | 50 | | | | | 55 | | | | | 60 | | | | |

| Lys | Val | Ile | Leu | Glu | Leu | Val | Glu | Gln | Leu | Arg | Gln | Asp | Asp | Ser | Met |
| 65 | | | | | 70 | | | | | 75 | | | | | 80 |

| Tyr | Leu | Val | Val | Ile | Gly | His | Ala | Asp | Ala | Thr | Gly | Thr | Glu | Glu | Tyr |
| | | | | 85 | | | | | 90 | | | | | 95 | |

| Ser | Leu | Ala | Leu | Gly | Glu | Lys | Arg | Ala | Asn | Ala | Val | Lys | Gln | Phe | Ile |
| | | | 100 | | | | | 105 | | | | | 110 | | |

| Ile | Gly | Cys | Asp | Lys | Ser | Leu | Ala | Pro | Arg | Val | Thr | Thr | Gln | Ser | Arg |
| | | | 115 | | | | | 120 | | | | | 125 | | |

| Gly | Lys | Ala | Glu | Pro | Glu | Val | Leu | Val | Tyr | Ser | Thr | Asp | Ala | Gln | Glu |
| | 130 | | | | | 135 | | | | | 140 | | | | |

| Val | Glu | Lys | Ala | Asn | Ala | Gln | Asn | Arg | Arg | Ala | Val | Ile | Val | Val | Glu |
| 145 | | | | | 150 | | | | | 155 | | | | | 160 |

| Phe | Ala | His | Ile | Pro | Arg | Ser | Gly | Ile | Ala | Asp | Met | His | Ala | Pro | Val |
| | | | | 165 | | | | | 170 | | | | | 175 | |

| Ala | Ser | Ser | Ile | Thr | Ser | Glu | Asn | Ser | Asn | Ala | Ser | Ala | Glu | Gly | Glu |
| | | | 180 | | | | | 185 | | | | | 190 | | |

| Asp | Met | Glu | Ala | Ser | Glu | Phe | Ser | Ser | Ala | Ile | Ala | Asn | | | |
| | | | 195 | | | | | 200 | | | | | 205 | | |

<210> SEQ ID NO 84
<211> LENGTH: 205
<212> TYPE: PRT
<213> ORGANISM: Anaplasma phagocytophilum

<400> SEQUENCE: 84

| Met | Leu | Arg | Arg | Ser | Ser | Phe | Phe | Cys | Leu | Leu | Ala | Leu | Leu | Ser | Val |
| 1 | | | | 5 | | | | | 10 | | | | | 15 | |

| Thr | Ser | Cys | Gly | Thr | Leu | Leu | Pro | Asp | Ser | Asn | Val | Gly | Val | Gly | Arg |
| | | | 20 | | | | | 25 | | | | | 30 | | |

| His | Asp | Leu | Gly | Ser | His | Arg | Ser | Val | Ala | Phe | Ala | Lys | Lys | Val | Glu |
| | | | 35 | | | | 40 | | | | | 45 | | | |

| Lys | Val | Tyr | Phe | Asp | Ile | Gly | Lys | Tyr | Asp | Leu | Lys | Gly | Pro | Gly | Lys |
| | 50 | | | | | 55 | | | | | 60 | | | | |

| Lys | Val | Ile | Leu | Glu | Leu | Val | Glu | Gln | Leu | Arg | Gln | Asp | Asp | Ser | Met |
| 65 | | | | | 70 | | | | | 75 | | | | | 80 |

| Tyr | Leu | Val | Val | Ile | Gly | His | Ala | Asp | Ala | Thr | Gly | Thr | Glu | Glu | Tyr |
| | | | | 85 | | | | | 90 | | | | | 95 | |

| Ser | Leu | Ala | Leu | Gly | Glu | Lys | Arg | Ala | Asn | Ala | Val | Lys | Gln | Phe | Ile |
| | | | 100 | | | | | 105 | | | | | 110 | | |

| Ile | Gly | Cys | Asp | Lys | Ser | Leu | Ala | Pro | Arg | Val | Thr | Thr | Gln | Ser | Arg |
| | | | 115 | | | | | 120 | | | | | 125 | | |

| Gly | Lys | Ala | Glu | Pro | Glu | Val | Leu | Val | Tyr | Ser | Thr | Asp | Ala | Gln | Glu |
| | 130 | | | | | 135 | | | | | 140 | | | | |

| Val | Glu | Lys | Ala | Asn | Ala | Gln | Asn | Arg | Arg | Ala | Val | Ile | Val | Val | Glu |
| 145 | | | | | 150 | | | | | 155 | | | | | 160 |

```
Phe Ala His Ile Pro Arg Ser Gly Ile Ala Asp Met His Ala Pro Val
                165                 170                 175

Ala Ser Ser Ile Thr Ser Glu Asn Ser Asn Ala Ser Ala Glu Gly Glu
            180                 185                 190

Asp Met Glu Ala Ser Glu Phe Ser Ala Ile Ala Asn
        195                 200                 205

<210> SEQ ID NO 85
<211> LENGTH: 205
<212> TYPE: PRT
<213> ORGANISM: Anaplasma phagocytophilum

<400> SEQUENCE: 85

Met Leu Arg Arg Ser Ser Phe Phe Cys Leu Leu Ala Leu Leu Ser Val
1               5                   10                  15

Thr Ser Cys Gly Thr Leu Leu Pro Asp Ser Asn Val Gly Val Gly Arg
            20                  25                  30

His Asp Leu Gly Ser His Arg Ser Val Ala Phe Ala Lys Lys Val Glu
        35                  40                  45

Lys Val Tyr Phe Asp Ile Gly Lys Tyr Asp Leu Lys Gly Pro Gly Lys
    50                  55                  60

Lys Val Ile Leu Glu Leu Val Glu Gln Leu Lys Gln Asp Asp Ser Met
65                  70                  75                  80

Tyr Leu Val Val Ile Gly His Ala Asp Ala Thr Gly Thr Glu Glu Tyr
                85                  90                  95

Ser Leu Ala Leu Gly Glu Lys Arg Ala Asn Ala Val Lys Gln Phe Ile
            100                 105                 110

Ile Gly Cys Asp Lys Ser Leu Ala Pro Arg Val Thr Thr Gln Ser Arg
        115                 120                 125

Gly Lys Ala Glu Pro Glu Val Leu Val Tyr Ser Thr Asp Ala Gln Glu
    130                 135                 140

Val Glu Lys Ala Asn Ala Gln Asn Arg Arg Ala Val Ile Val Val Glu
145                 150                 155                 160

Phe Ala His Thr Pro Arg Ser Gly Val Ala Asp Met His Ala Pro Val
                165                 170                 175

Ala Ser Ser Ile Thr Ser Glu Asn Ser Asn Ala Ser Ala Glu Gly Glu
            180                 185                 190

Asp Met Glu Ala Ser Glu Phe Ser Glu Ile Ala Lys
        195                 200                 205

<210> SEQ ID NO 86
<211> LENGTH: 236
<212> TYPE: PRT
<213> ORGANISM: Anaplasma marginale

<400> SEQUENCE: 86

Met Leu His Arg Trp Leu Ala Leu Cys Phe Leu Ala Ser Phe Ala Val
1               5                   10                  15

Thr Gly Cys Gly Leu Phe Ser Lys Glu Lys Val Gly Met Asp Ile Val
            20                  25                  30

Gly Val Pro Phe Ser Ala Gly Arg Val Glu Lys Val Tyr Phe Asp Phe
        35                  40                  45

Asn Lys Tyr Glu Ile Lys Gly Ser Gly Lys Lys Val Leu Leu Gly Leu
    50                  55                  60

Val Glu Arg Met Lys Ala Asp Lys Arg Ser Thr Leu Leu Ile Ile Gly
65                  70                  75                  80
```

```
His Thr Asp Ser Arg Gly Thr Glu Glu Tyr Asn Leu Ala Leu Gly Glu
            85                  90                  95

Arg Arg Ala Asn Ala Val Lys Glu Phe Ile Leu Gly Cys Asp Arg Ser
            100                 105                 110

Leu Ser Pro Arg Ile Ser Thr Gln Ser Arg Gly Lys Ala Glu Pro Glu
            115                 120                 125

Val Leu Val Tyr Ser Ser Asp Phe Lys Glu Ala Glu Lys Ala His Ala
    130                 135                 140

Gln Asn Arg Arg Val Val Leu Ile Val Glu Cys Gln His Ser Val Ser
145                 150                 155                 160

Pro Lys Lys Lys Met Ala Ile Lys Trp Pro Phe Ser Phe Gly Arg Ser
            165                 170                 175

Ala Ala Lys Gln Asp Asp Val Gly Ser Ser Glu Val Ser Asp Glu Asn
            180                 185                 190

Pro Val Asp Asp Ser Ser Glu Gly Ile Ala Ser Glu Glu Ala Ala Pro
            195                 200                 205

Glu Glu Gly Val Val Ser Glu Glu Ala Ala Glu Glu Ala Pro Glu Val
    210                 215                 220

Ala Gln Asp Ser Ser Ala Gly Val Val Ala Pro Glu
225                 230                 235

<210> SEQ ID NO 87
<211> LENGTH: 255
<212> TYPE: PRT
<213> ORGANISM: Anaplasma marginale

<400> SEQUENCE: 87

Met Gly Phe Phe Ser Gly Tyr Arg Ser Trp Ile Phe Ser Val Gly Glu
1               5                   10                  15

Val Phe Thr Met Leu His Arg Trp Leu Ala Leu Cys Phe Leu Ala Ser
            20                  25                  30

Phe Ala Val Thr Gly Cys Gly Leu Phe Ser Lys Glu Lys Val Gly Met
            35                  40                  45

Asp Ile Val Gly Val Pro Phe Ser Ala Gly Arg Val Glu Lys Val Tyr
    50                  55                  60

Phe Asp Phe Asn Lys Tyr Glu Ile Lys Gly Ser Gly Lys Lys Val Leu
65                  70                  75                  80

Leu Gly Leu Val Glu Arg Met Lys Ala Asp Lys Arg Ser Thr Leu Leu
            85                  90                  95

Ile Ile Gly His Thr Asp Ser Arg Gly Thr Glu Glu Tyr Asn Leu Ala
            100                 105                 110

Leu Gly Glu Arg Arg Ala Asn Ala Val Lys Glu Phe Ile Leu Gly Cys
            115                 120                 125

Asp Arg Ser Leu Ser Pro Arg Ile Ser Thr Gln Ser Arg Gly Lys Ala
    130                 135                 140

Glu Pro Glu Val Leu Val Tyr Ser Ser Asp Phe Lys Glu Ala Glu Lys
145                 150                 155                 160

Ala His Ala Gln Asn Arg Arg Val Val Leu Ile Val Glu Cys Gln His
            165                 170                 175

Ser Val Ser Pro Lys Lys Lys Met Ala Ile Lys Trp Pro Phe Ser Phe
            180                 185                 190

Gly Arg Ser Ala Ala Lys Gln Asp Asp Val Gly Ser Ser Glu Val Ser
            195                 200                 205

Asp Glu Asn Pro Val Asp Asp Ser Ser Glu Gly Ile Ala Ser Glu Glu
```

```
                        210                 215                 220
Ala Ala Pro Glu Glu Gly Val Ser Glu Ala Glu Glu Ala
225                 230                 235                 240

Pro Glu Val Ala Gln Asp Ser Ser Ala Gly Val Val Ala Pro Glu
                245                 250                 255

<210> SEQ ID NO 88
<211> LENGTH: 212
<212> TYPE: PRT
<213> ORGANISM: Anaplasma marginale

<400> SEQUENCE: 88

Met Leu His Arg Trp Leu Ala Leu Cys Leu Leu Ala Ser Leu Ala Val
1               5                   10                  15

Thr Gly Cys Glu Leu Phe Asn Lys Glu Lys Val Asn Ile Asp Ile Gly
                20                  25                  30

Gly Val Pro Leu Ser Ala Gly Arg Val Glu Lys Val Tyr Phe Asp Phe
            35                  40                  45

Asn Lys Tyr Glu Ile Lys Gly Ser Gly Lys Lys Val Leu Leu Gly Leu
        50                  55                  60

Val Glu Arg Met Lys Ala Asp Lys Met Ser Thr Leu Leu Ile Val Gly
65                  70                  75                  80

His Thr Asp Ser Arg Gly Thr Glu Glu Tyr Asn Leu Ala Leu Gly Glu
                85                  90                  95

Arg Arg Ala Asn Ala Val Lys Glu Phe Ile Leu Gly Cys Asp Arg Ser
                100                 105                 110

Leu Ser Pro Arg Ile Ser Thr Gln Ser Arg Gly Lys Ala Glu Pro Glu
            115                 120                 125

Ile Leu Val Tyr Ser Ser Asp Phe Lys Glu Ala Glu Lys Ala His Ala
        130                 135                 140

Gln Asn Arg Arg Val Val Leu Ile Met Glu Cys Gln His Ala Ala Ser
145                 150                 155                 160

Pro Lys Lys Ala Arg Val Ser Arg Trp Pro Phe Ser Phe Gly Arg Ser
                165                 170                 175

Ser Ala Thr Gln Gln Asp Asn Gly Gly Thr Val Ala Ala Gly Ser
                180                 185                 190

Pro Gly Glu Asp Ala Pro Ala Glu Val Val Glu Pro Glu Thr Gln
            195                 200                 205

Glu Ala Gly Glu
        210

<210> SEQ ID NO 89
<211> LENGTH: 175
<212> TYPE: PRT
<213> ORGANISM: Ehrlichia spp.

<400> SEQUENCE: 89

Met Lys His Lys Leu Val Phe Ile Lys Phe Met Leu Leu Cys Leu Ile
1               5                   10                  15

Leu Ser Ser Cys Lys Thr Thr Asp His Val Pro Leu Val Asn Val Asp
                20                  25                  30

His Val Phe Ser Asn Thr Lys Thr Ile Glu Lys Ile Tyr Phe Gly Phe
            35                  40                  45

Gly Lys Ala Thr Ile Glu Asp Ser Asp Lys Thr Ile Leu Glu Lys Val
        50                  55                  60

Met Gln Lys Ala Glu Glu Tyr Pro Asp Thr Asn Ile Ile Ile Val Gly
```

```
                65                  70                  75                  80
His Thr Asp Thr Arg Gly Thr Asp Glu Tyr Asn Leu Glu Leu Gly Lys
                    85                  90                  95

Gln Arg Ala Asn Ala Val Lys Asp Phe Ile Leu Glu Arg Asn Lys Ser
                100                 105                 110

Leu Glu Asp Arg Ile Ile Ile Glu Ser Lys Gly Lys Ser Glu Pro Ala
                115                 120                 125

Val Leu Val Tyr Ser Asn Asn Pro Glu Glu Ala Glu Tyr Ala His Thr
            130                 135                 140

Lys Asn Arg Arg Val Val Ile Thr Leu Thr Asp Asn Leu Ile Tyr Lys
145                 150                 155                 160

Ala Lys Ser Ser Asp Lys Asp Pro Ser Ser Asn Lys Thr Glu Gln
                165                 170                 175
```

<210> SEQ ID NO 90
<211> LENGTH: 162
<212> TYPE: PRT
<213> ORGANISM: Ehrlichia spp.

<400> SEQUENCE: 90

```
Met Lys His Lys Leu Val Phe Ile Lys Phe Ile Leu Leu Cys Leu Ile
1               5                   10                  15

Leu Ser Ser Cys Lys Thr Thr Asp His Val Pro Leu Val Asn Thr Asp
                20                  25                  30

His Val Phe Ser Asn Met Lys Thr Ile Glu Lys Ile Tyr Phe Asp Phe
            35                  40                  45

Gly Lys Ala Thr Ile Gly Asp Ser Asp Lys Ala Ile Leu Glu Lys Val
        50                  55                  60

Ile Gln Lys Ala Gln Lys Asp Thr Asn Thr Asn Ile Val Ile Val Gly
65                  70                  75                  80

His Thr Asp Thr Arg Gly Thr Asp Glu Tyr Asn Leu Glu Leu Gly Glu
                    85                  90                  95

Gln Arg Ala Asn Ala Val Lys Asp Phe Ile Ile Glu His Asp Lys Ser
                100                 105                 110

Leu Glu Asn Arg Ile Thr Val Gln Ser Lys Gly Lys Ser Glu Pro Ala
                115                 120                 125

Val Leu Val Tyr Ser Ser Asn Pro Glu Glu Ala Glu His Ala His Ala
            130                 135                 140

Lys Asn Arg Arg Val Val Ile Thr Leu Thr Asp Asn Gly Asn Lys Thr
145                 150                 155                 160

Ser Gln
```

<210> SEQ ID NO 91
<211> LENGTH: 217
<212> TYPE: PRT
<213> ORGANISM: Ehrlichia spp.

<400> SEQUENCE: 91

```
Met Arg Tyr Gln Leu Ile Val Ala Asn Leu Ile Leu Leu Cys Leu Thr
1               5                   10                  15

Leu Asn Gly Cys His Phe Asn Ser Lys His Val Pro Leu Val Asn Val
                20                  25                  30

His Asn Leu Phe Ser Asn Ile Lys Ala Ile Asp Lys Val Tyr Phe Asp
            35                  40                  45

Leu Asp Lys Thr Val Ile Lys Asp Ser Asp Lys Val Leu Leu Glu Lys
        50                  55                  60
```

-continued

```
Leu Val Gln Lys Ala Gln Glu Asp Pro Thr Thr Asp Ile Ile Ile Val
 65              70                  75                      80

Gly His Thr Asp Thr Arg Gly Thr Asp Glu Tyr Asn Leu Ala Leu Gly
                 85                  90                  95

Glu Gln Arg Ala Asn Ala Val Arg Asp Phe Ile Ile Ser Cys Asp Lys
            100                 105                 110

Ser Leu Glu Lys Arg Ile Thr Val Arg Ser Lys Gly Lys Ser Glu Pro
            115                 120                 125

Ala Ile Leu Val Tyr Ser Asn Asn Pro Lys Glu Ala Glu Asp Ala His
130                     135                 140

Ala Lys Asn Arg Arg Val Val Ile Thr Leu Val Asn Asn Ser Thr Ser
145                 150                 155                 160

Thr Asp Asn Lys Val Pro Thr Thr Thr Thr Pro Phe Asn Glu Glu Ala
                165                 170                 175

His Asn Thr Ile Ser Lys Asp Gln Glu Asn Asn Thr Gln Gln Gln Ala
                180                 185                 190

Lys Ser Asp Asn Ile Asn Asn Ile Asn Thr Gln Gln Lys Leu Glu Gln
            195                 200                 205

Asp Asn Asn Asn Thr Pro Glu Val Asn
210                 215
```